(12) United States Patent
Feldman et al.

(10) Patent No.: US 8,165,651 B2
(45) Date of Patent: Apr. 24, 2012

(54) ANALYTE SENSOR, AND ASSOCIATED SYSTEM AND METHOD EMPLOYING A CATALYTIC AGENT

(75) Inventors: Benjamin J. Feldman, Oakland, CA (US); Zenghe Liu, Alameda, CA (US); David C. Cohen, Oakland, CA (US); Adam Heller, Austin, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 1734 days.

(21) Appl. No.: 11/007,617

(22) Filed: Dec. 7, 2004

(65) Prior Publication Data

US 2005/0215871 A1 Sep. 29, 2005

Related U.S. Application Data

(63) Continuation-in-part of application No. 10/819,498, filed on Apr. 6, 2004, which is a continuation-in-part of application No. 10/775,604, filed on Feb. 9, 2004, now abandoned.

(51) Int. Cl.
*A61B 5/05* (2006.01)
*A61B 5/00* (2006.01)

(52) U.S. Cl. .......................... 600/347; 600/345; 600/365

(58) Field of Classification Search .................. 600/345, 600/365, 347
See application file for complete search history.

(56) References Cited

U.S. PATENT DOCUMENTS

| | | |
|---|---|---|
| 3,164,534 A | 1/1965 | Free |
| 4,703,756 A | 11/1987 | Gough et al. |
| 4,820,399 A | 4/1989 | Senda et al. |
| 4,891,104 A | 1/1990 | Liston et al. |
| 4,974,929 A | 12/1990 | Curry |
| 5,200,051 A | 4/1993 | Cozzette et al. |
| 5,202,317 A | 4/1993 | Bruice |
| 5,217,966 A | 6/1993 | Bruice |
| 5,227,405 A | 7/1993 | Fridovich et al. |
| 5,262,305 A | 11/1993 | Heller et al. |
| 5,264,104 A | 11/1993 | Gregg et al. |
| 5,320,725 A | 6/1994 | Gregg et al. |

(Continued)

FOREIGN PATENT DOCUMENTS

DE 150656 9/1981

(Continued)

OTHER PUBLICATIONS

Barynin et al. "Crystal Structure of Manganese Catalase from *Lactobacillus plantarum*" Structure, vol. 9, 725-738, Aug. 2001.*

(Continued)

*Primary Examiner* — Patricia Mallari
*Assistant Examiner* — Christian Jang
(74) *Attorney, Agent, or Firm* — Edward J. Baba; Khin K. Chin; Bozicevic, Field & Francis LLP

(57) ABSTRACT

An analyte sensor for use in connection with a biofluid is described. The analyte sensor may comprise any suitable interface between the biofluid and a derivative of the biofluid and any suitable transducer of information concerning an analyte. At least one catalytic agent is provided in a locale or vicinity of the interface. The catalytic agent, such as a proteinaceous agent or a non-proteinaceous, organic-metal agent, is sufficient to catalyze the degradation of reactive oxygen and/or nitrogen species that may be present in the vicinity of the interface. An analyte-sensing kit and a method of sensing an analyte are also described.

25 Claims, 11 Drawing Sheets

U.S. PATENT DOCUMENTS

| | | |
|---|---|---|
| 5,356,786 A | 10/1994 | Heller et al. |
| 5,431,160 A | 7/1995 | Wilkins |
| 5,466,575 A | 11/1995 | Cozzette et al. |
| 5,468,562 A | 11/1995 | Farivar et al. |
| 5,593,852 A | 1/1997 | Heller et al. |
| 5,610,293 A | 3/1997 | Riley et al. |
| 5,640,954 A | 6/1997 | Pfeiffer et al. |
| 5,651,869 A | 7/1997 | Yoshioka et al. |
| 5,665,222 A | 9/1997 | Heller et al. |
| 5,696,109 A | 12/1997 | Malfroy-Camine et al. |
| 5,771,890 A | 6/1998 | Tamada |
| 5,882,494 A | 3/1999 | Van Antwerp |
| 5,906,921 A | 5/1999 | Ikeda et al. |
| 5,914,026 A * | 6/1999 | Blubaugh et al. ............. 600/347 |
| 5,947,957 A | 9/1999 | Morris |
| 5,964,993 A | 10/1999 | Blubaugh, Jr. et al. |
| 5,972,199 A | 10/1999 | Heller et al. |
| 5,994,339 A | 11/1999 | Crapo et al. |
| 6,011,077 A | 1/2000 | Müller |
| 6,023,629 A | 2/2000 | Tamada |
| 6,049,727 A | 4/2000 | Crothall |
| 6,081,736 A | 6/2000 | Colvin et al. |
| 6,084,093 A | 7/2000 | Riley et al. |
| 6,091,976 A | 7/2000 | Pfeiffer et al. |
| 6,103,033 A | 8/2000 | Say et al. |
| 6,103,714 A | 8/2000 | Fridovich et al. |
| 6,110,155 A | 8/2000 | Baudino |
| 6,119,028 A | 9/2000 | Schulman et al. |
| 6,120,676 A | 9/2000 | Heller et al. |
| 6,122,536 A | 9/2000 | Sun et al. |
| 6,127,356 A | 10/2000 | Crapo et al. |
| 6,134,461 A * | 10/2000 | Say et al. ..................... 600/345 |
| 6,143,164 A | 11/2000 | Heller et al. |
| 6,144,869 A | 11/2000 | Berner et al. |
| 6,175,752 B1 | 1/2001 | Say et al. |
| 6,190,315 B1 | 2/2001 | Kost et al. |
| 6,214,817 B1 | 4/2001 | Riley et al. |
| 6,245,758 B1 | 6/2001 | Stern et al. |
| 6,254,586 B1 | 7/2001 | Mann et al. |
| 6,267,002 B1 | 7/2001 | Ehwald et al. |
| 6,268,161 B1 | 7/2001 | Han et al. |
| 6,298,254 B2 | 10/2001 | Tamada |
| 6,329,161 B1 | 12/2001 | Heller et al. |
| 6,338,790 B1 | 1/2002 | Feldman et al. |
| 6,343,225 B1 | 1/2002 | Clark |
| 6,368,274 B1 | 4/2002 | Van Antwerp et al. |
| 6,372,045 B1 | 4/2002 | McCabe |
| 6,400,974 B1 | 6/2002 | Lesho |
| 6,403,788 B1 | 6/2002 | Meunier et al. |
| 6,434,409 B1 | 8/2002 | Pfeiffer et al. |
| 6,436,255 B2 | 8/2002 | Yamamoto et al. |
| 6,438,414 B1 | 8/2002 | Conn et al. |
| 6,448,239 B1 | 9/2002 | Groves et al. |
| 6,466,810 B1 | 10/2002 | Ward et al. |
| 6,475,181 B1 | 11/2002 | Potter et al. |
| 6,475,196 B1 | 11/2002 | Vachon |
| 6,477,395 B2 | 11/2002 | Schulman et al. |
| 6,477,891 B2 | 11/2002 | Ehwald et al. |
| 6,479,477 B1 | 11/2002 | Crapo et al. |
| 6,491,657 B2 | 12/2002 | Rowe et al. |
| 6,497,729 B1 | 12/2002 | Moussy et al. |
| 6,508,785 B1 | 1/2003 | Eppstein |
| 6,512,939 B1 | 1/2003 | Colvin et al. |
| 6,525,041 B1 | 2/2003 | Neumann et al. |
| 6,530,915 B1 | 3/2003 | Eppstein et al. |
| 6,541,490 B1 | 4/2003 | Campbell et al. |
| 6,544,975 B1 | 4/2003 | Crapo et al. |
| 6,560,471 B1 | 5/2003 | Heller et al. |
| 6,573,257 B2 | 6/2003 | Malfroy-Camine et al. |
| 6,589,948 B1 | 7/2003 | Malfroy-Camine et al. |
| 6,591,126 B2 | 7/2003 | Roeper et al. |
| 6,592,746 B1 * | 7/2003 | Schmid-Schoenbein et al. ..................... 205/778 |
| 6,599,407 B2 | 7/2003 | Taniike et al. |
| 6,602,678 B2 | 8/2003 | Kwon et al. |
| 6,620,123 B1 | 9/2003 | Mitragotri et al. |
| 6,679,841 B2 | 1/2004 | Bojan et al. |
| 6,685,699 B1 | 2/2004 | Eppstein et al. |
| 6,702,857 B2 | 3/2004 | Brauker et al. |
| 6,723,077 B2 | 4/2004 | Pickup et al. |
| 6,740,215 B1 | 5/2004 | Nakaminami et al. |
| 6,741,877 B1 | 5/2004 | Shults et al. |
| 6,746,582 B2 | 6/2004 | Heller et al. |
| 6,770,729 B2 | 8/2004 | Van Antwerp |
| 6,835,387 B2 * | 12/2004 | Herrmann ..................... 424/425 |
| 6,885,196 B2 | 4/2005 | Taniike et al. |
| 2001/0020125 A1 * | 9/2001 | Kurnik et al. ................. 600/347 |
| 2001/0039393 A1 | 11/2001 | Mori et al. |
| 2001/0041830 A1 | 11/2001 | Varalli et al. |
| 2002/0006634 A1 | 1/2002 | Han et al. |
| 2002/0042407 A1 | 4/2002 | Fridovich et al. |
| 2002/0068860 A1 * | 6/2002 | Clark, Jr. ..................... 600/347 |
| 2002/0082490 A1 | 6/2002 | Roeper et al. |
| 2002/0183604 A1 * | 12/2002 | Gowda et al. ................. 600/345 |
| 2003/0031699 A1 | 2/2003 | Van Antwerp |
| 2003/0042137 A1 | 3/2003 | Mao et al. |
| 2003/0055032 A1 | 3/2003 | Groves et al. |
| 2003/0065254 A1 | 4/2003 | Schulman et al. |
| 2003/0069281 A1 | 4/2003 | Fridovich et al. |
| 2003/0077702 A1 | 4/2003 | Shah et al. |
| 2003/0077772 A1 | 4/2003 | Shah et al. |
| 2003/0078560 A1 | 4/2003 | Miller et al. |
| 2003/0099682 A1 | 5/2003 | Moussy et al. |
| 2003/0118577 A1 | 6/2003 | Weill et al. |
| 2003/0190341 A1 | 10/2003 | Shalaby et al. |
| 2003/0199837 A1 | 10/2003 | Vachon |
| 2003/0217966 A1 | 11/2003 | Tapsak et al. |
| 2004/0028612 A1 | 2/2004 | Singaram et al. |
| 2004/0063167 A1 | 4/2004 | Kaastrup et al. |
| 2004/0064133 A1 | 4/2004 | Miller et al. |
| 2004/0074785 A1 | 4/2004 | Holker et al. |
| 2004/0110722 A1 | 6/2004 | Ornberg et al. |
| 2004/0116332 A1 | 6/2004 | Ornberg et al. |
| 2005/0031689 A1 | 2/2005 | Shults et al. |
| 2005/0033132 A1 | 2/2005 | Shults et al. |

FOREIGN PATENT DOCUMENTS

| | | |
|---|---|---|
| EP | 1 153 571 A1 | 11/2001 |
| WO | WO 94/10560 A1 | 5/1994 |
| WO | WO 95/31197 A1 | 11/1995 |
| WO | WO 98/17199 A2 | 4/1998 |
| WO | WO 98/43637 A1 | 10/1998 |
| WO | WO 2008/043637 A1 | 10/1998 |
| WO | WO 99/47471 A1 | 9/1999 |
| WO | WO 00/75144 A1 | 12/2000 |
| WO | WO 00/78293 A1 | 12/2000 |
| WO | WO 01/36660 A2 | 5/2001 |
| WO | WO 03/063925 A1 | 8/2003 |
| WO | WO 03/076893 A2 | 9/2003 |
| WO | WO 2004/007756 A1 | 1/2004 |
| WO | WO 2004/028337 A2 | 4/2004 |

OTHER PUBLICATIONS

Heller et al., "Amperometric Biosensors Based on Three-Dimensional Hydrogel-Forming Epoxy Networks," *Sensor and Actutators B*, 13-14, 1993, pp. 180-183.

Maidan et al., "Elimination of Electrooxidizable Interferants in Glucos Electrodes," *J. Am. Chem: Soc.* 1991, 113, pp. 9003-9004.

Maidan et al., "Elimintation of Electrooxidizable Interferant-Produced Currents in Amperometric Biosensors," *Anal. Chem.*, 1992, 64, pp. 2889-2896.

Batinić-Haberle, "Manganese Porphyrins and Related Compounds as Mimics of Superoxide Dismutase," *Methods Enzymol*, 349, 2002, pp. 223-233.

Chan et al., "Free Fatty Acids, Oxygen Free Radicals, and Membrane Alterations in Brain Ischemia and Injury," *Cerebrovascular. Diseases*, 1985, pp. 161-171.

Chan et al., "Protective Effects of Liposome-Entrapped Superoxide Dismutase on Posttraumatic Brain Edema," *Annals of Neurology*, vol. 21, No. 6, Jun. 1987, pp. 540-547.

Csöregi et al., "Design, Chracterization, and One-Point in Vivo Calibration of a *Subcutaneously* Implanted Glucose Electrode," *Analytical Chemistry*, vol. 66, No. 19, Oct. 1, 1994, pp. 3131-3138.

Csöregi et al., "Design and Optimization of a Selective *Subcutaneously* Implantable Glucose Electrode Based on 'Wired' Glucose Oxidase," *Analytical Chemistry*, vol. 67, No. 7, Apr. 1, 1995, pp. 1240-1244.

Doctrow et al., "Salen-Manganese Complexes: Combined Superoxide Dismutase/Catalase Mimics with Broad Pharmacological Efficacy," *Advances in Pharmacology*, vol. 38, 1997, pp. 247-269.

McGowan et al., "Spurious Reporting of Nocturnal Hypoglycemia by CGMC in Patients with Tightly Controlled Type 1 Diabetes," *Diabetes Care*, vol. 25, No. 9, Sep. 2002, pp. 1499-1503.

Mabley et al., "Part II: Beneficial Effects of the Peroxynitrite Decomposition Catalyst FP15 in Murine Models of Arthritis and Colitis," *Molecular Medicine*, vol. 8, No. 10, Oct. 2002, pp. 581-590.

Metzger et al., "Reproducibility of Glucose Measurements Using the Glucose Sensor," *Diabetes Care*, vol. 25, No. 6, Jul. 2002, pp. 1185-1191.

Pacher et al., "Potent Metalloporphyrin Peroxynitrite Decomposition Catalyst Protects Against the Development of Doxorubicin-Induced Cardiac Dysfunction," *Circulation*, Feb. 18, 2003, vol. 107, No. 6. pp. 896-904.

Riley, "Functional Mimics of Superoxide Dismutase Enzymes as Therapeutic Agents," *Chemical Reviews*, 1999, vol. 99, No. 9, pp. 2573-2587.

Salvemini et al., "Superoxide Dismutase Mimetics," *Pulmonary Pharmacology & Therapeutics*, 2002, vol. 15, pp. 439-447.

Schmidtke et al., "Measurement and Modeling of the Transient Difference Between Blood and *Subcutaneous* Glucose Concentrations in the Rate after Injection of Insulin," *Proc. Natl. Acad. Sci. USA*, vol. 95. 1998. pp. 294-299.

Schmidtke et al., "Accuracy of the One-Point in Vivo Calibration of 'Wired' Glucose Oxidase Electrodes Implanted in Jugular Veins of Rates in Periods of Rapid Rise and Decline of the Glucose Concentration," *Analytical Chemistry*. vol. 70. No. 10. May 15. 1998. pp. 2149-2155.

Schmidtke et al., "Statistics for Critical Clinical Decision Making Based on Readings of Pairs of Implanted Sensors," *Analytical Chemistry*, vol. 68, No. 17, Sep. 1, 1996, pp. 2845-2849.

Szabó et al., Part I: Pathogenetic Role of Peroxynitrite in the Development of Diabetes and Diabetic Vascular Complications: Studies with FP15, A Novel Potent Peroxynitrite Decomposition Catalyst, *Molecular Medicine*. vol. 8. No. 10. Oct. 2002. pp. 571-579.

Thomé-Duret et al., "Use of a *Subcutaneous* Glucose Sensor to Detect Decreases in Glucose Concentration Prior to Observation in Blood," *Analytical Chemistry*, vol. 68, No. 21, Nov. 1, 1996, pp. 3822-3826.

Udipi et al., "Modification of Inflammatory Response to Implanted Biomedical Materials in vivo by Surface Bound Superoxide Dismutase Mimics," *J. Biomed. Mater. Res*. 2000, vol. 51, No. 4, pp. 549-560.

Weiss et al., "Manganese-Based Superoxide Dismutase Mimetics Inhibit Neutrophil Infiltration in vivo," *The Journal of Biological Chemistry*, vol. 271, No. 42, Oct. 18, 1996, pp. 26149-26156.

DirecNet Study Group, "Accuracy of the GlucoWatch G2 Biographer and the Continuous Glucose Monitoring System During Hypoglycemia," *Diabetes Care*, vol. 27, No. 3, Mar. 2004, pp. 722-726.

Tamada et al., The Effect of Preapplication of Corticosteroids on Skin Irritation and Performance of the GlucoWatch G2® Biographer, *Diabetes Technology & Therapeutics*, vol. 6, No. 3, 2004, pp. 357-367.

Monsod et al., "Do Sensor Glucose Levels Accurately Predict Plasma Glucose Concentrations During Hypoglycemia and Hyperinsulinemia?" *Diabetes Care*, vol. 25, No. 5, May 2002, pp. 889-893.

Mauras, M.D., et al., "Lack of Accuracy of Continuous Glucose Sensors in Healthy, Nondiabetic Children: Results of the Diabetes Research in Children Network (DirecNet) Accuracy Study," *The Journal of Pediatrics*. Jun. 2004. pp. 770-775.

Kaufman, M.D., et al., "Nocturnal Hypoglycemia Detected with the Continuous Glucose Monitoring System in Pediatric Patients with Type 1 Diabetes," *Journal of Pediatrics*, Nov. 2002, pp. 625-630.

Feldman, Ph.D., et al., "A Continuous Glucose Sensor Based on Wired Enzyme™ Technology —Results from a 3-Day Trial in Patients with Type 1 Diabetes," *Diabetes Technology & Therapeutics*, vol. 5, No. 5. 2003. pp. 769-779.

Gamache et al., "Simultaneous Measurement of Monoamines, Metabolites and Amino Acids in Brain Tissue and Microdialysis Perfusates," *Journal of Chromatography*, 614 (1993) pp. 213-220.

Niwa et al., "Concentration of Extracellular L-Glutamate Released from Cultured Nerve Cells Measured with a Small-Volume Online Sensor," *Anal.Chem*., 1996, 68, pp. 1865-1870.

Notification of Transmittal of the International Search Report and the Written Opinion of the International Searching Authority, or the Declaration, International Application No. PCT/US2005/002821 for TheraSense, Inc., mailed Jun. 9, 2005.

* cited by examiner

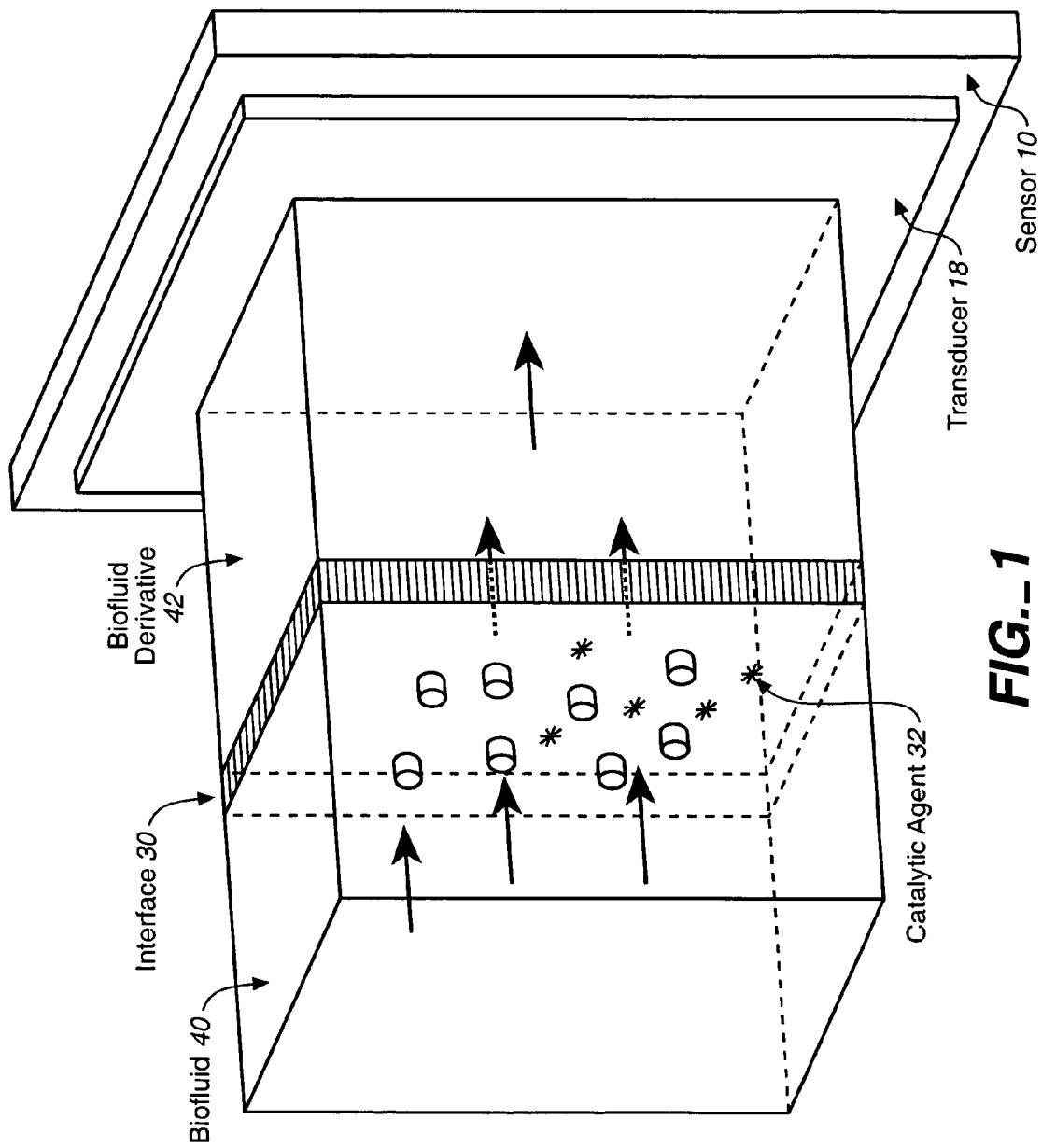
FIG._1

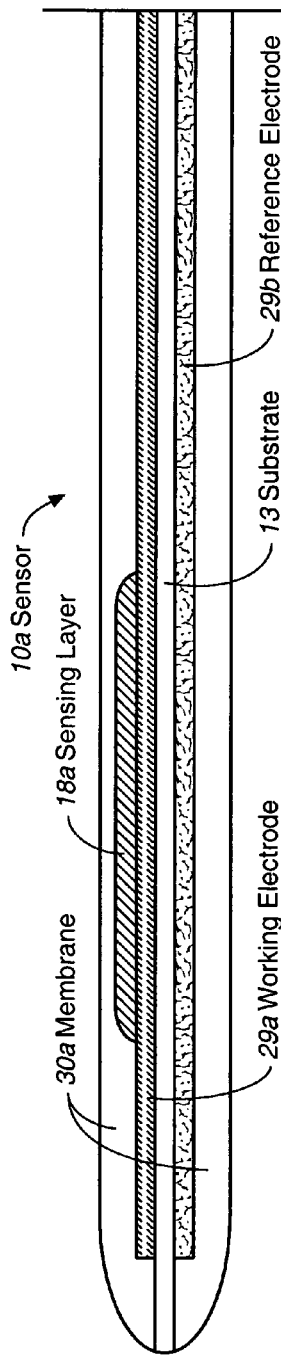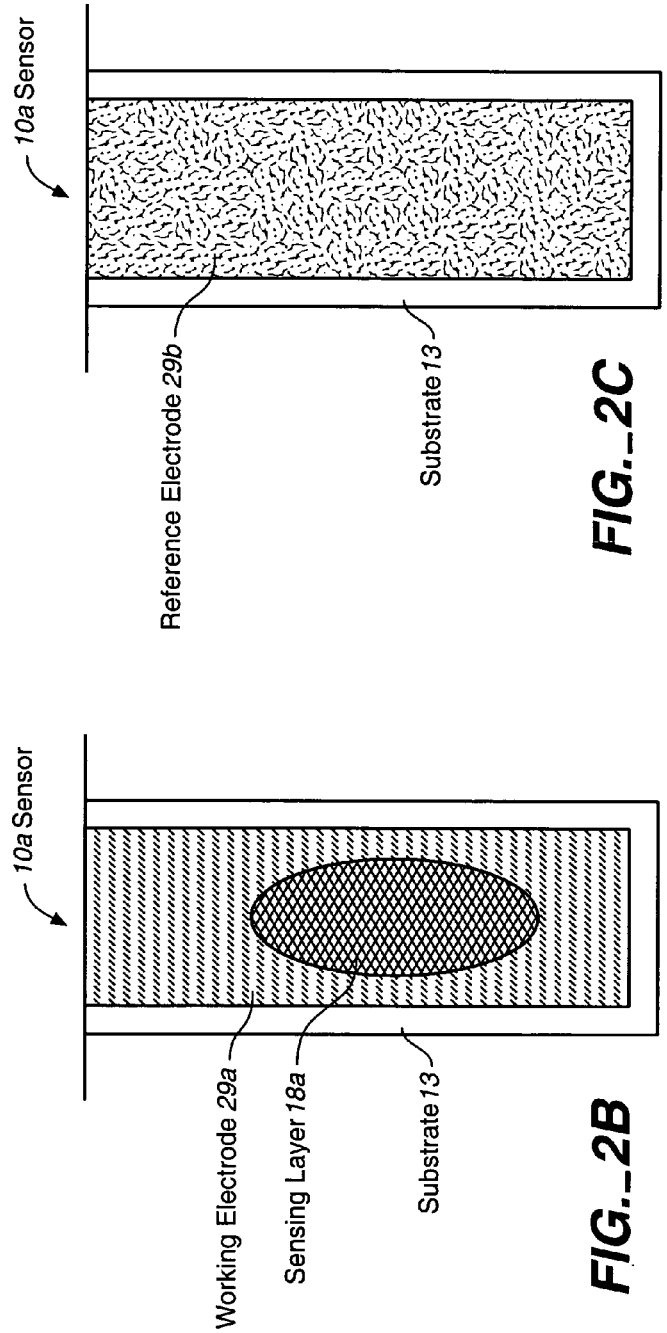

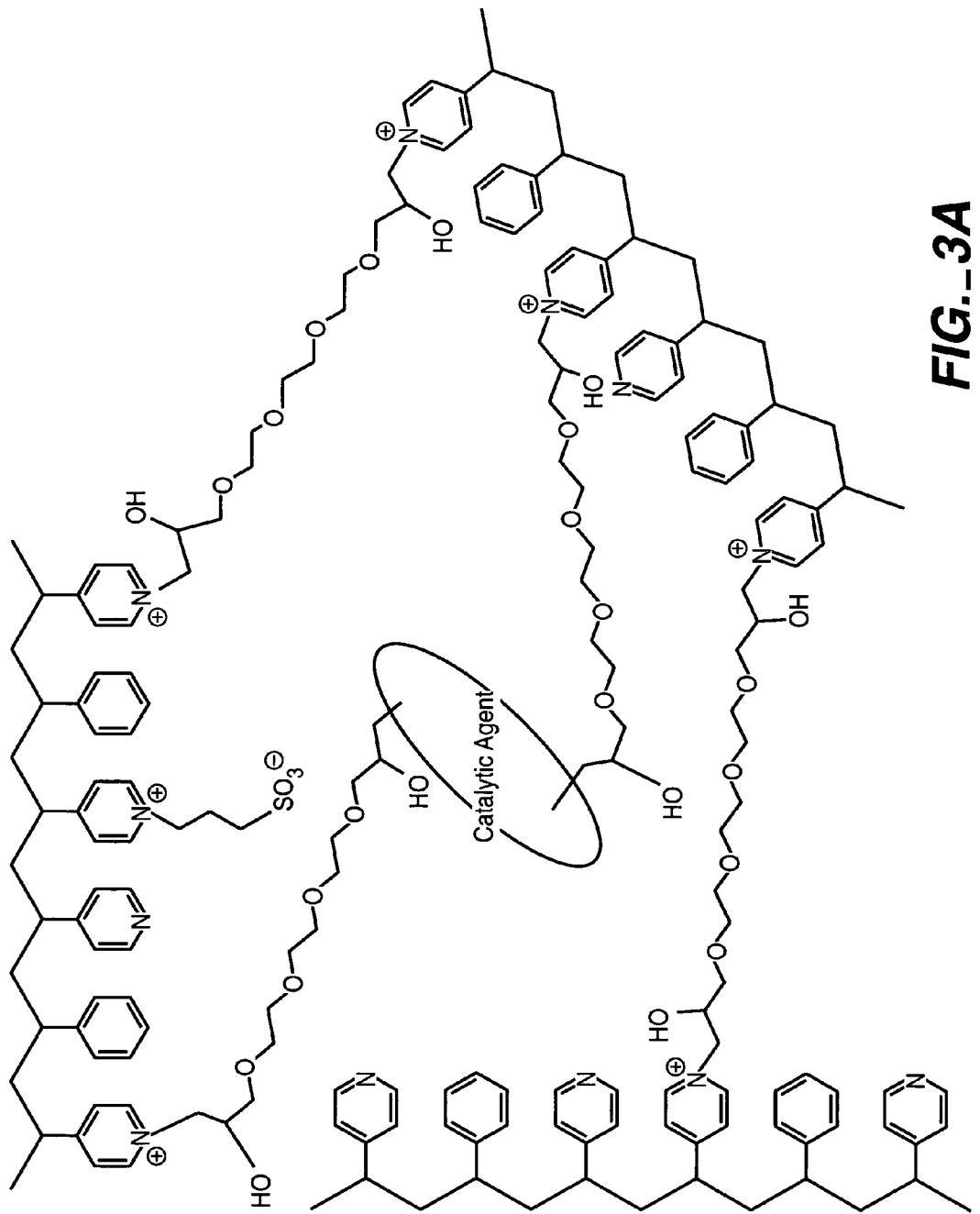
FIG._3A

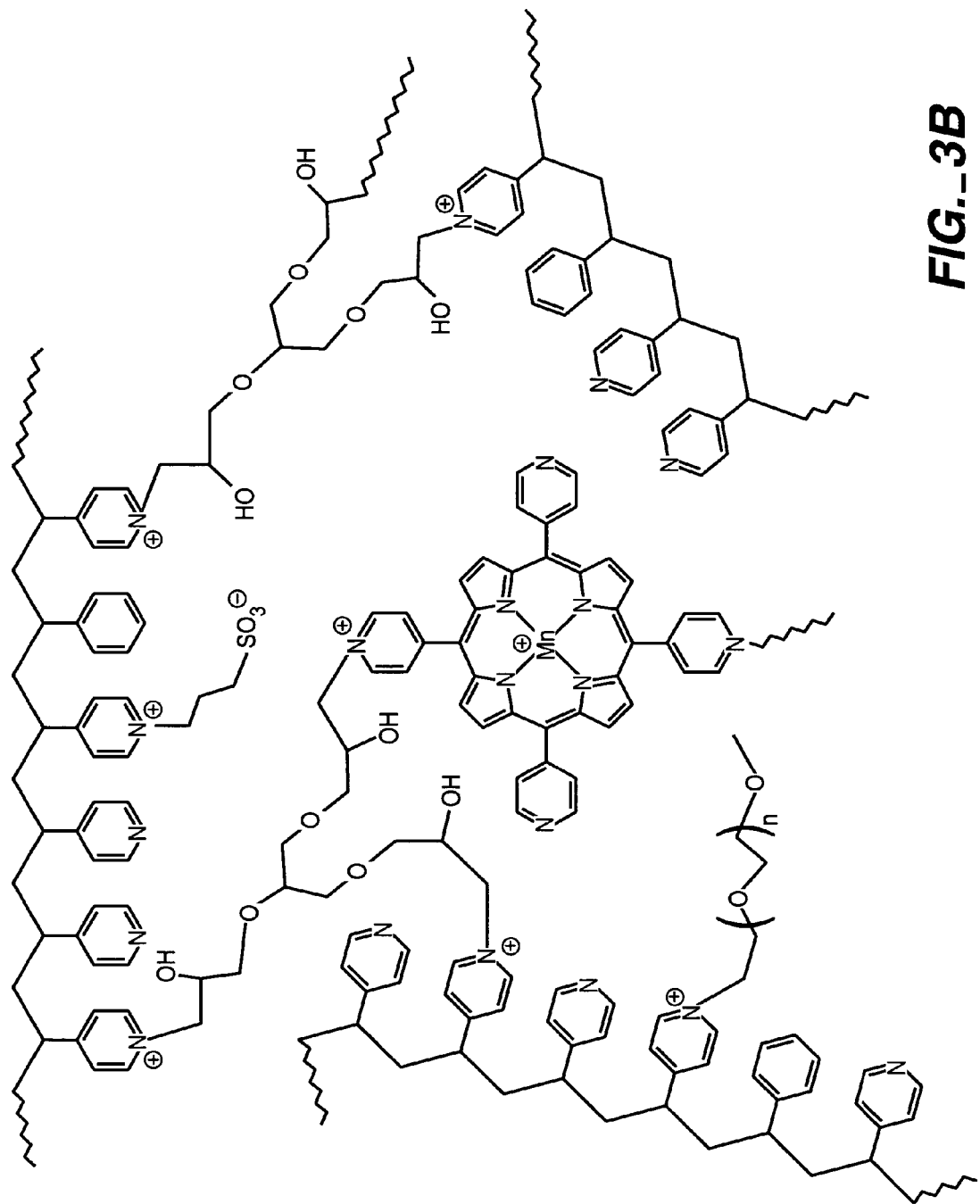
FIG._3B

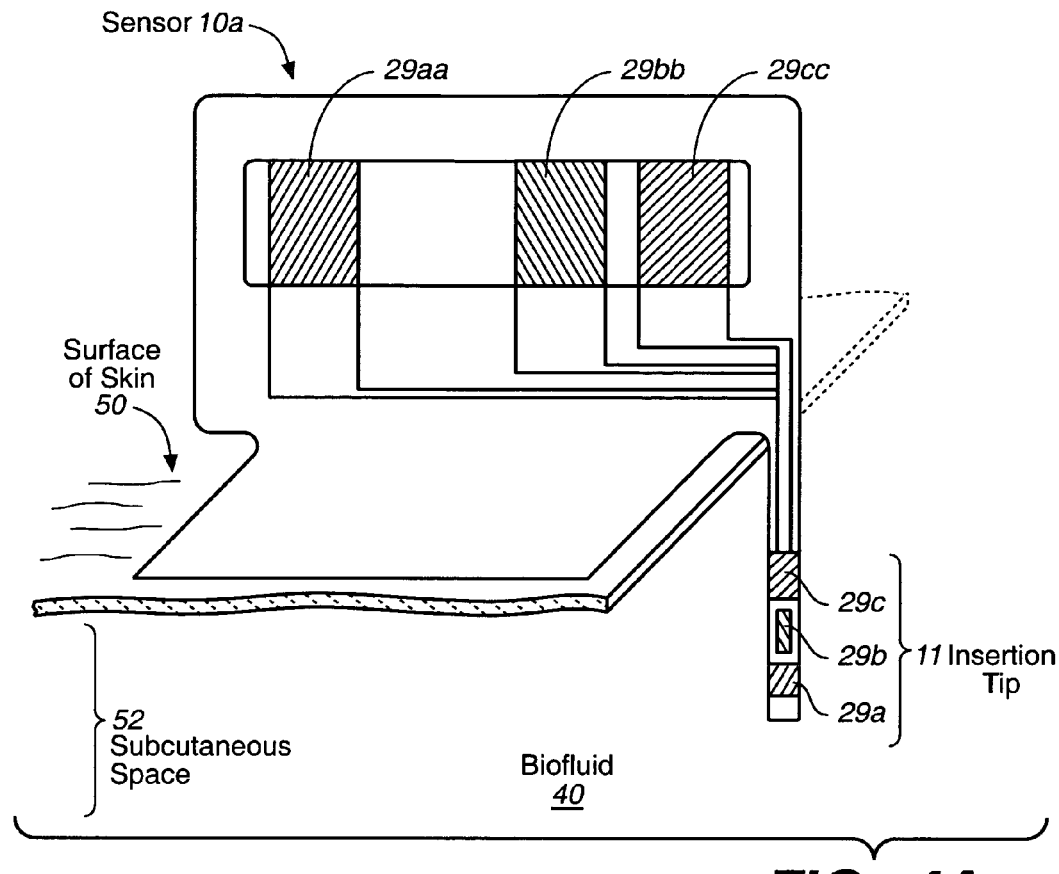
FIG._4A
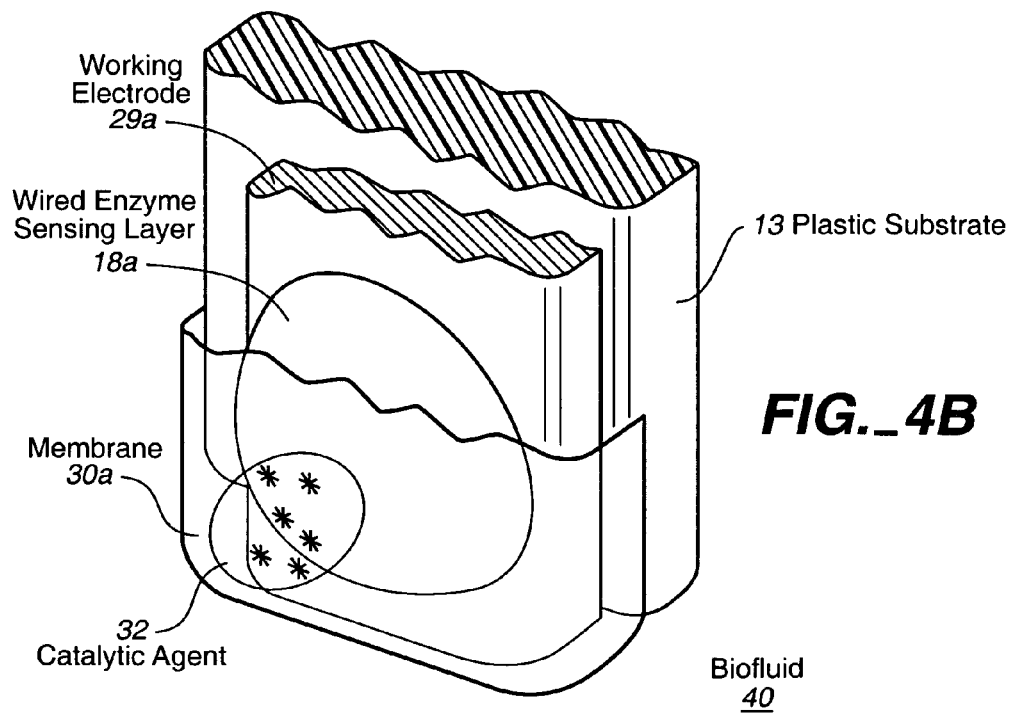
FIG._4B

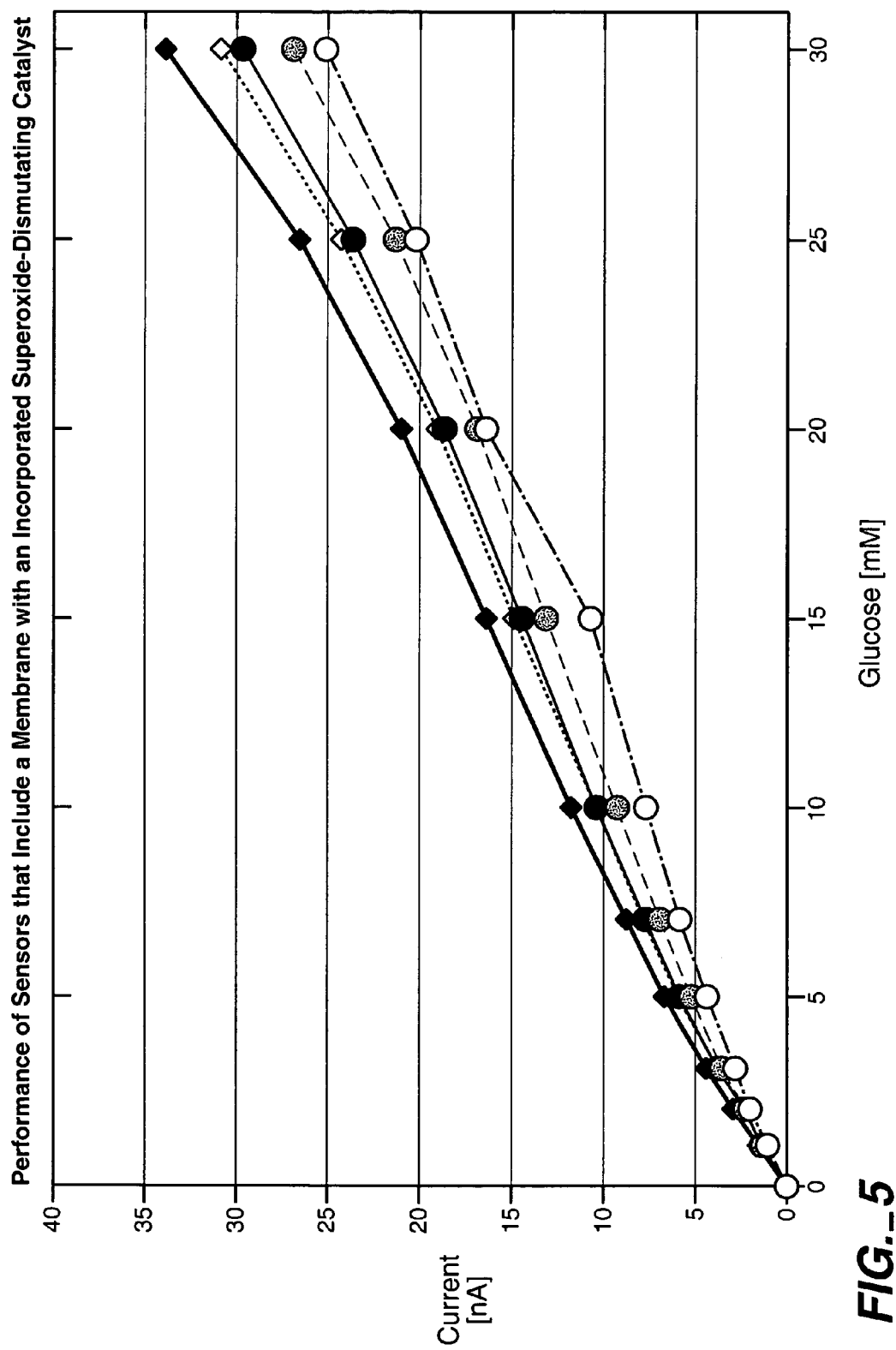

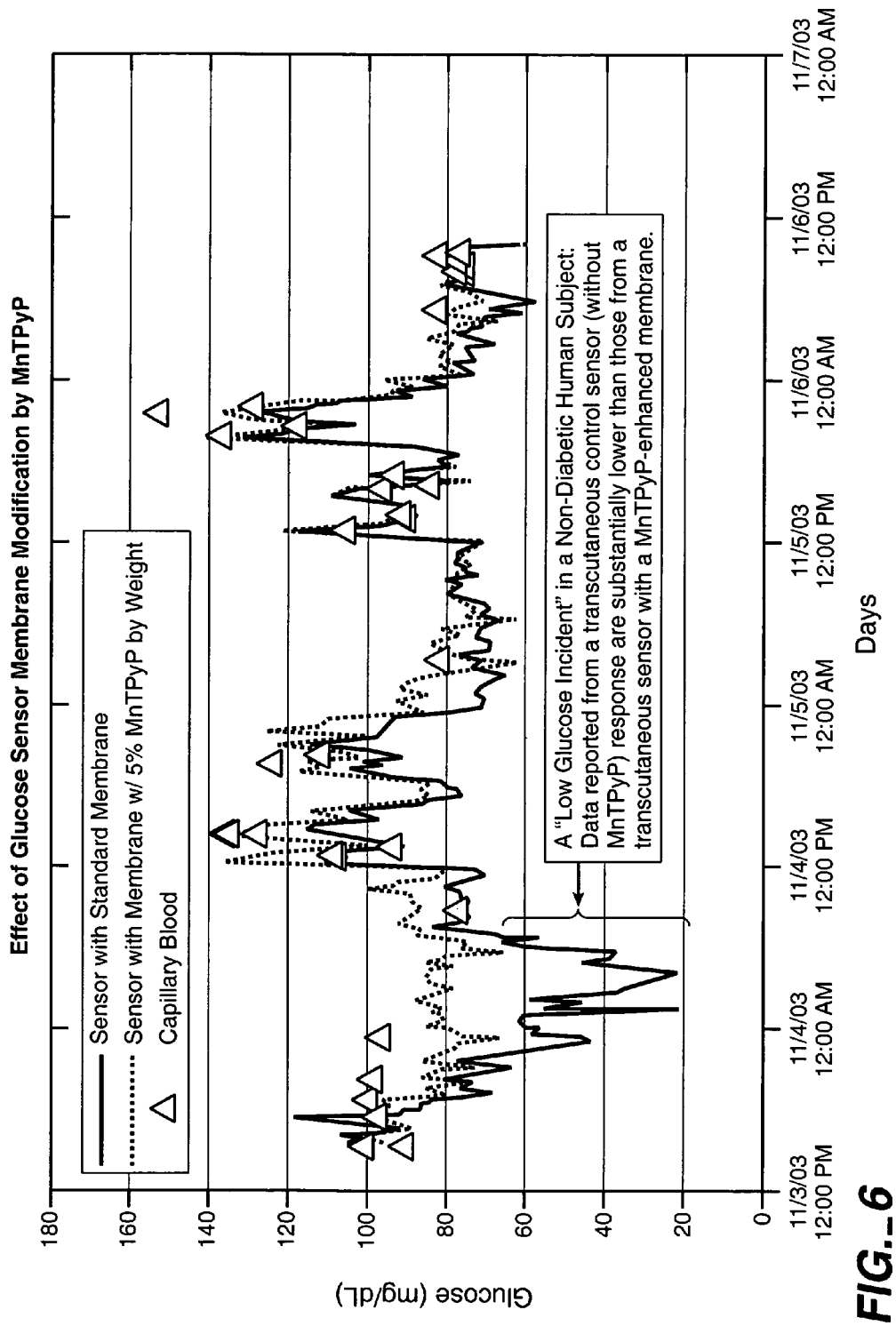
FIG._6

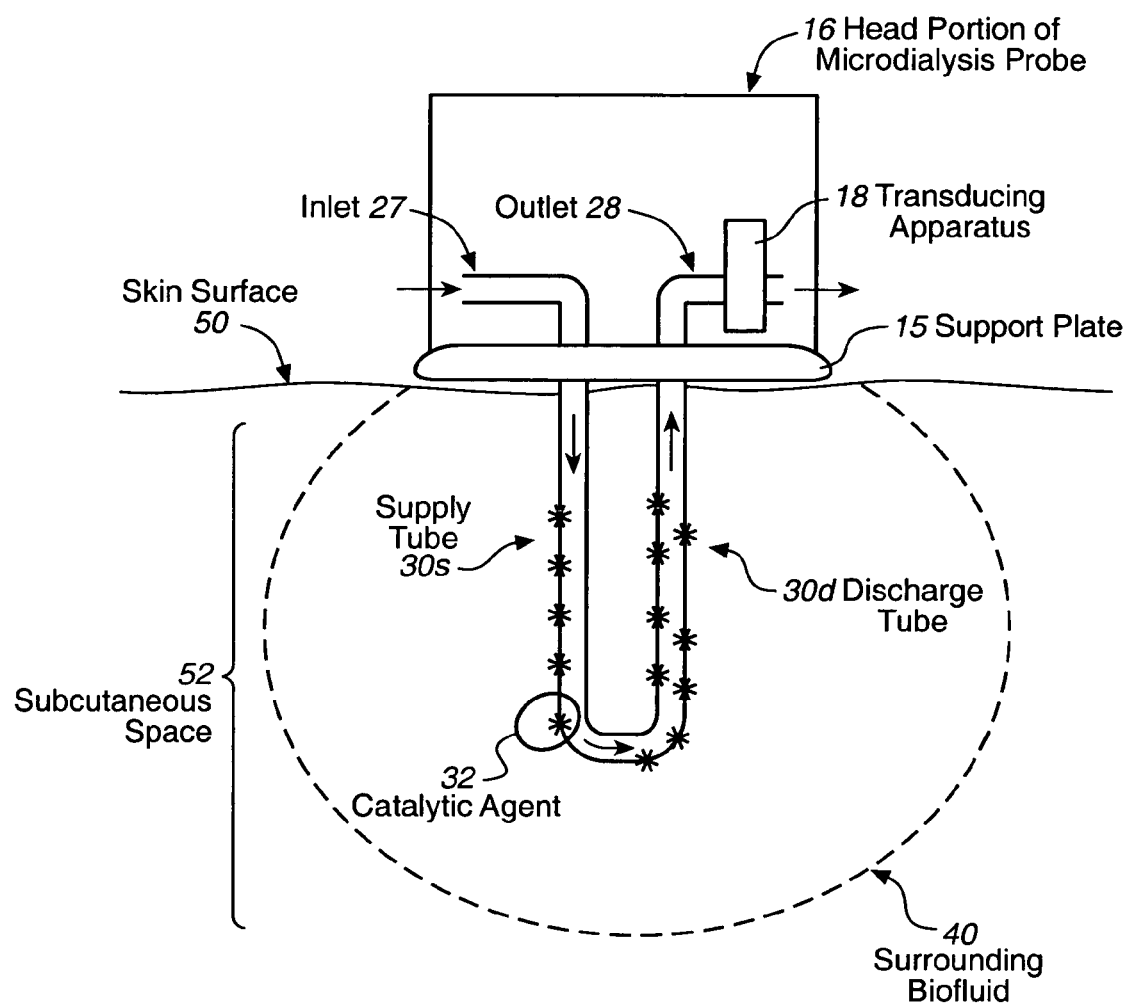
FIG._7

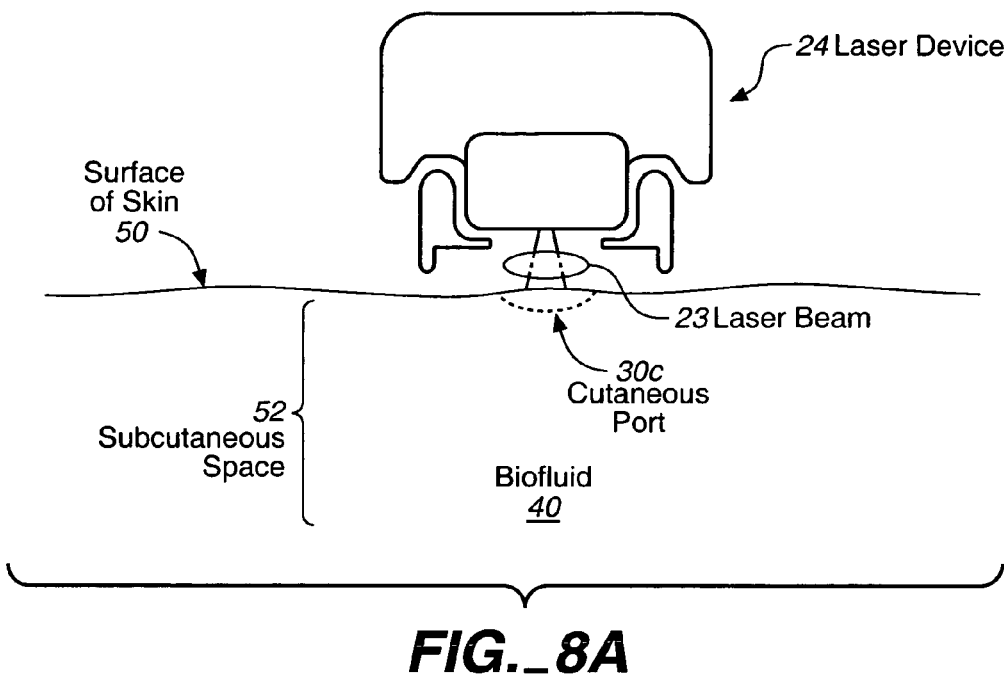
FIG._8A
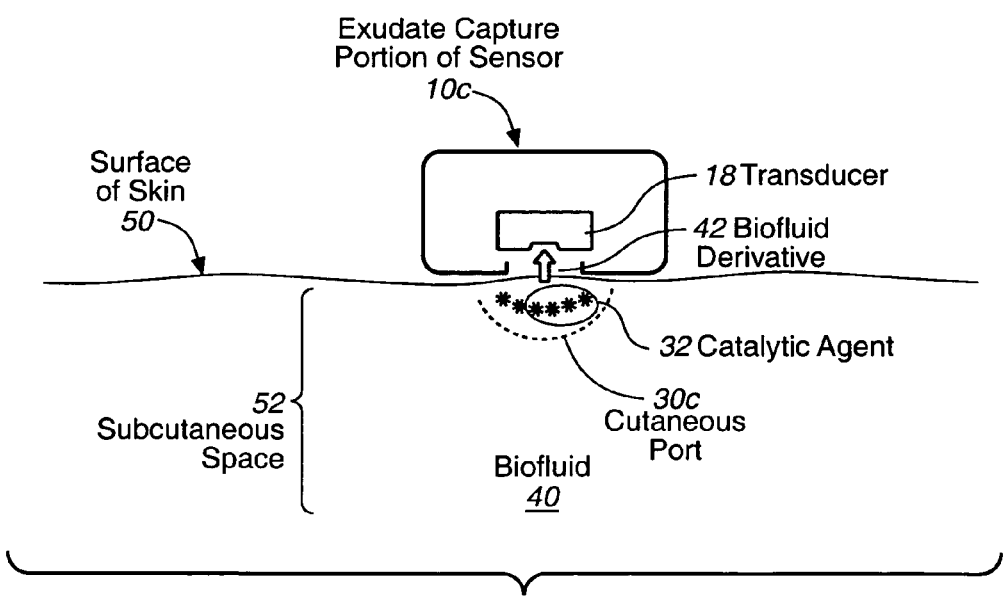
FIG._8B

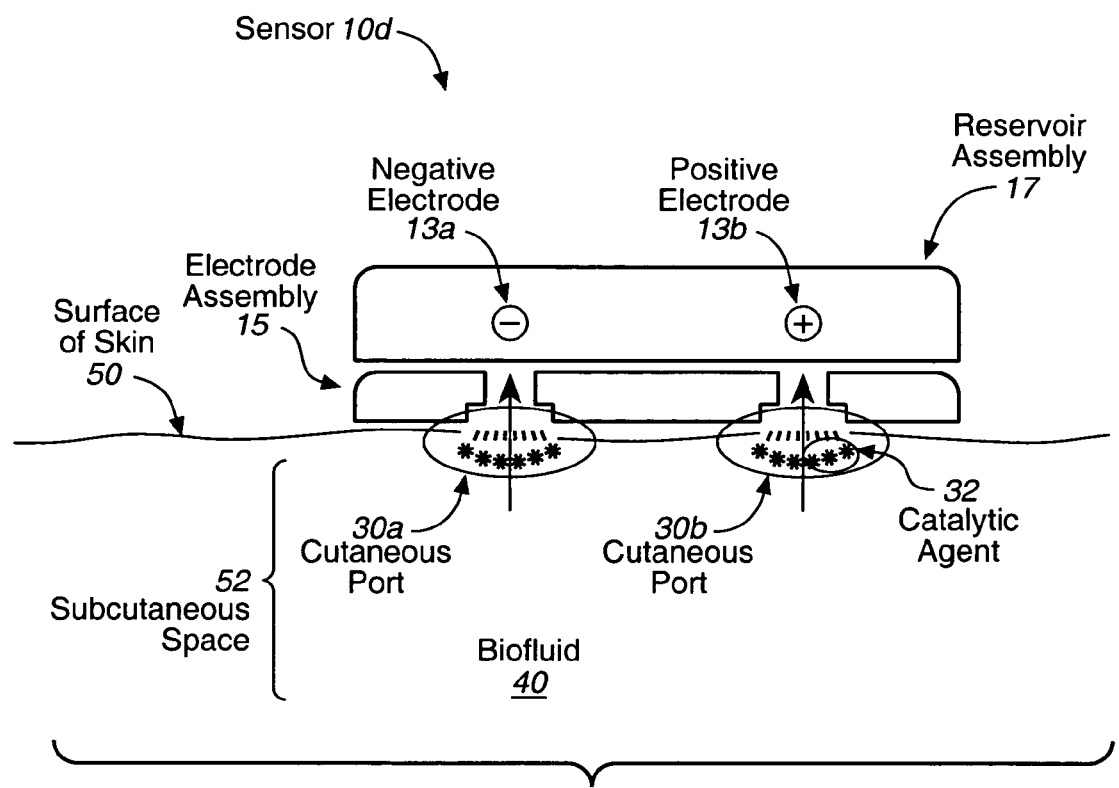
FIG._9

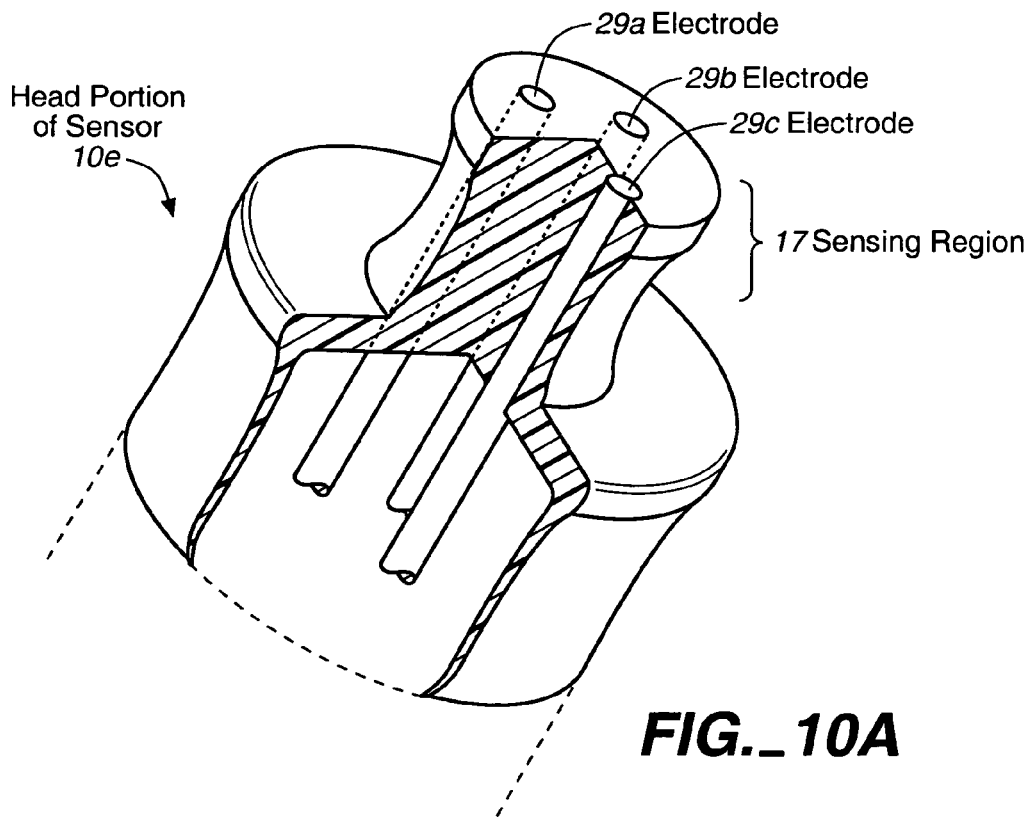
FIG. _10A
FIG. _10B
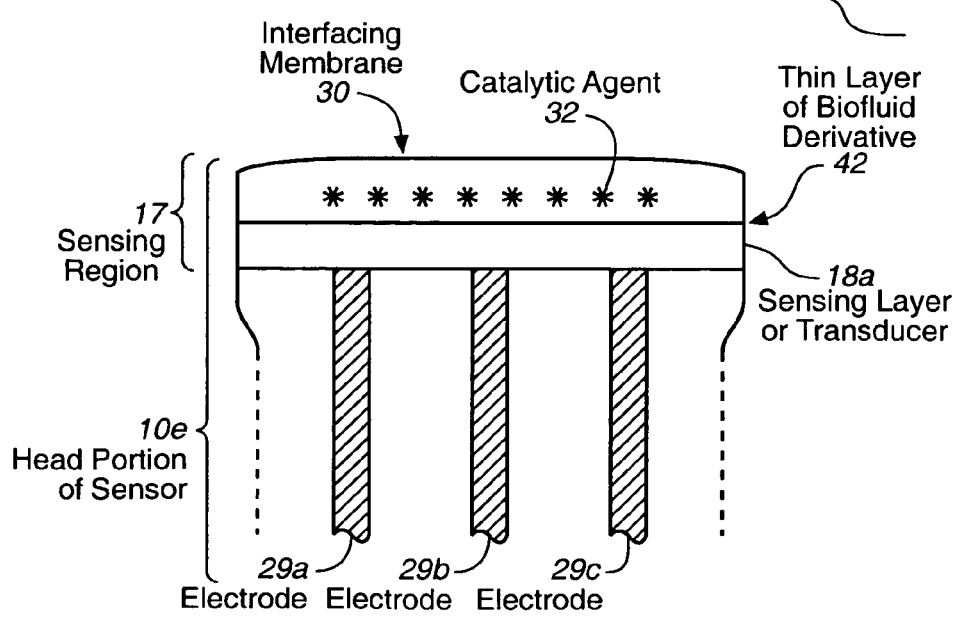

ANALYTE SENSOR, AND ASSOCIATED SYSTEM AND METHOD EMPLOYING A CATALYTIC AGENT

CROSS-REFERENCE TO RELATED APPLICATIONS

This application is a continuation-in-part of U.S. patent application Ser. No. 10/819,498 of Feldman et al., filed on Apr. 6, 2004, which is a continuation-in-part of U.S. patent application Ser. No. 10/775,604 of Feldman et al., filed on Feb. 9, 2004 now abandoned. This application is additionally related to U.S. patent application Ser. No. 10/146,518 of Mao et al., filed on May 14, 2002, the corresponding U.S. Patent Application Publication No. U.S. 2003/0042137A1 of Mao et al., published on Mar. 6, 2003, and U.S. Provisional Patent Application No. 60/291,215 of Mao, filed on May 15, 2001. Each of the aforementioned applications, publication, and provisional application, is incorporated in its entirety herein by this reference.

FIELD OF THE INVENTION

This invention generally relates to the provision of catalytic agents within the locale of an interface between a biofluid and derivatives of the biofluid, where the derivative of the biofluid contacts the sensing mechanism of an analyte sensor. The invention additionally relates to analyte sensors that make use of any of a variety of transducing mechanisms, and which may be placed internally, transcutaneously, or externally, relative to a body.

BACKGROUND OF THE INVENTION

Various analyte sensors, such as glucose biosensors, have been developed that provide continuous information from the body with regard to analyte concentrations. These sensors thus can be described as operating in vivo, i.e., partially or wholly within a living body. Such in vivo sensors are thus exposed, in varying degree, to the biological environment, and they differ fundamentally in the way in which they are used from ex vivo sensors, such as glucose strip readers, in which a biofluid sample is taken from a subject and conveyed away to an external device for a discrete sample reading. Various methodologies or mechanisms have been applied to the task of transducing the concentration of an analyte of interest into an informative signal (Pearson et al., *Analytical Aspects of Biosensors*, Ann. Clin. Biochem, 37: 119-145, 2000). Such transducing methodologies include electrochemical methods, such as amperometric, potentiometric, and coulometric methods, by way of example. Other transducing methodologies include optical methods, such as luminescence-, and fluorescence-, and refractive index-based methodologies, by way of example. There are still other methodologies, such as thermal transduction, piezoelectric transduction, and viscosimetric transduction, merely by way of example.

Clinical use of biosensors that provide continuous data has been a significant step toward helping diabetic patients achieve tight control over their blood glucose levels, a goal considered desirable ever since the report of the Diabetes Control and Complications Trial Research Group Study (N. E. J. M. 329: 977-986, 1993). Sensors designed for in vivo operation can be described variously in terms of the particular technologies they employ, the site of their placement in or on a body, and the degree of their invasiveness into the body. Some transcutaneous sensor systems, such as the Freestyle® Navigator™ Continuous Glucose Monitoring System (Abbott Diabetes Care, formerly known as TheraSense, Inc., Alameda, Calif.), are designed for the placement of a sensor portion into a subcutaneous area of the body, while a base portion remains external to the body. The sensor portion includes a membrane that covers its sensing surface, provides a level physical protection of the sensing surface, and also limits the rate of analyte flux to the sensing surface in a way that is advantageous to the electrochemical kinetics of the sensor.

Some transcutaneous continuous sensor systems include a microdialysis loop placed into a subcutaneous area of the body, while a sensor portion remains external to the body. The microdialysis loop provides for the circulation of a solution into and out of the subcutaneous space where it contacts the transducing apparatus of a sensor placed externally, on the skin. The microdialysate fluid emerging from the transit through the subcutaneous space is in equilibrium with the interstitial fluid respect to the concentration of the analyte, and thus is a useful analyte-sensing medium. Examples of microdialysis-based analyte sensing systems suitable for glucose sensing have been described in U.S. Pat. No. 5,640,954 of Pfeiffer et al., filed on May 5, 1995, U.S. Pat. No. 6,091,976 of Pfeiffer et al., filed on Oct. 28, 1998, and U.S. Pat. No. 6,591,126 of Reoper et al., filed on Jul. 20, 2001; U.S. Patent Application Publication No. 2001/0041830 A1 of Varalli et al., filed on May 7, 2001; and European Patent Application No. EP 1153571 A1 of Varalli et al., filed on May 3, 2001.

Still other sensor systems are associated with means or methods that are used to create a disruption, or a wound, or an opening in the skin, or in more functional terms, a cutaneous port out of which fluid exudes. A sensor placed externally, on the skin, is used to sense the analyte concentration in the exuded fluid. This exuded fluid can differ from the interstitial fluid from which it is derived in terms of composition, but with respect to the analyte, is reflective of, or a function of the analyte concentration in the interstitial fluid. The exuded fluid may also differ from its "parent" biofluid according to the process or injury that gave rise to the cutaneous port, which may encompass any of various technologies or methodologies, such as laser burning, ultrasonic disruption, particle propulsion, and reverse iontophoresis, merely by way of example.

An example of an in vivo continuous analyte sensing system that makes use of a cutaneous port is one in which the port is photothermally-induced by a laser technology device as described in U.S. Pat. No. 6,508,785 of Eppstein, issued on Jan. 21, 2003, U.S. Pat. No. 6,530,915 of Eppstein et al., issued on Mar. 11, 2003, U.S. Pat. No. 6,679,841 of Bojan et al., issued on Jan. 20, 2004, and U.S. Pat. No. 6,685,699 of Eppstein et al., issued on Feb. 3, 2004. Further by way of example, another way to create a cutaneous port is through the use of focused ultrasonic waves to disrupt the ordered lipid bilayer of the stratum corneum. This disruption creates pores through which an interstitial fluid-derived wound fluid exudes, whereupon the exuded fluid is used as a sample fluid for a sensor external to the skin. Patents that describe this system include U.S. Pat. No. 6,620,123 of Mitragotri et al., issued on Sep. 16, 2003, U.S. Pat. No. 6,190,315 of Kost et al., issued on Feb. 20, 2001, U.S. Pat. No. 6,234,990 of Rowe et al., issued on May 22, 2001, and U.S. Pat. No. 6,491,657 of Rowe et al., issued on Dec. 10, 2002.

A further example of an approach to continuous in vivo analyte sensing has involves reverse iontophoresis, whereby weak electrical current is applied to a site on the skin to drive compounds outwardly through the skin. Patents describing a reverse iontophoretic sensing system include U.S. Pat. No.

6,023,629 of Tamada, issued on Feb. 8, 2000, U.S. Pat. No. 6,393,318 of Conn et al., issued on May 21, 2002, U.S. Pat. No. 6,438,414 of Conn et al., issued on Aug. 20, 2002, U.S. Pat. No. 5,771,890 of Tamada, issued on Jun. 30, 1998, and U.S. Pat. No. 6,298,254 of Tamada, issued on Oct. 2, 2001. As with other cutaneous port systems, internal from the iontophoretic site or wound surface is interstitial fluid in its native form, with its native immune cell population, albeit disturbed in varying degree by local reaction to the iontophoretic process, and external to the iontophoretic site or wound surface on the skin is an exuded, iontophoretically-driven fluid that comes into contact with the sensing surface.

In vivo or continuous sensing systems have had technical challenges to overcome in order to be able to compare favorably with the high standards of accuracy and dependability established by ex vivo strip-reading glucose sensors. For example, the operation and performance of an in vivo enzyme-based biosensor may be complicated by high rates of analyte flux, such that the relationship between the concentration of glucose in a sample fluid and the response from the biosensor becomes non-linear. This kinetic problem has been solved by the interposition of an analyte-flux-limiting membrane between the sample fluid and the sensing layer of the biosensor, as described in the above-mentioned U.S. Patent Application Publication No. U.S. 2003/0042137A1 of Mao et al. Still other challenges, such as usage limitations, have become evident. For example, data from studies of the recently available, transcutaneous CGMS system of Medtronic MiniMed, indicate spurious, low-glucose-reading incidents, particularly during periods of stillness, such as when a subject is asleep. (See Metzger et al., *Reproducibility of Glucose Measurements Using the Glucose Sensor*, Diabetes Care, July 2002, Vol. 25, 1185-1191; McGowan et al., *Spurious Reporting of Nocturnal Hypoglycemia by CGMS in Patients with Tightly Controlled Type* 1 *Diabetes*, Diabetes Care, September 2002, Vol. 25, 1499-1503; authored by The Diabetic Research in Children Network (DirecNet) Study Group, *Accuracy of the Gluco Watch G2 Biographer and the Continuous Glucose Monitoring System During Hypoglycemia*, Diabetes Care vol. 27, no. 3, 722-726, March 2004; and Mauras et al., *Lack of Accuracy of Continuous Glucose Sensors in Healthy, Nondiabetic Children, Results of the Diabetes Research in Children Network* (*DirecNet*) *Accuracy Study*, J. Pediatrics 144 (6), 770-775, June 2004.) While nocturnal hypoglycemic events are indeed a clinical reality, especially in patients being aggressively treated with insulin, it has become recognized that false indications of such events are particular fallibilities of the CGMS system that complicate the interpretation of the data obtained using this system. (See Monsod et al., *Do Sensor Glucose Levels Accurately Predict Plasma Glucose Concentrations During Hypoglycemia and Hyperinsulinemia?*, Diabetes Care, May 2002; and Kaufinan et al., *Nocturnal Hypoglycemia Detected with the Continuous Glucose Monitoring System in Pediatric Patients with Type* 1 *Diabetes*, J. Pediatrics 2002; vol. 141, 625-630). Spurious low-glucose-reading incidents are very problematic in the monitoring and treatment of a diabetic subject, as such incidents wrongly indicate that a euglycemic subject is hypoglycemic. As an example, when a spurious, low-glucose reading is used as a signal to control insulin dosage, a subject may receive an improper or a reduced dose of insulin and thus be put at risk for becoming hyperglycemic. Spurious low glucose readings can be further problematic as they may lead to incorrectly calibrated sensors, resulting in subsequent false, high glucose readings, which may reduce the credibility and usefulness of the alarm function, by way of example. Further development of biosensor components and biosensors for continuous in vivo monitoring of analyte levels, such as glucose levels, is desirable.

SUMMARY OF THE INVENTION

This invention generally relates to the provision of biocompatibility-promoting catalytic agents to in vivo analyte sensors within the locale of an interface between a biofluid and a derivative of the biofluid, where the derivative of the biofluid is the fluid that contacts the transducing mechanism sensor. The locale of the interface includes locations that may be within the interface or chemically incorporated into it, immediately adjacent to or in contact with the interface, or at a distance near enough to the interface that the effect of the catalytic agents is such that it alters the composition or population of chemical species that comprise the chemical environment surrounding the interface. These catalytic agents include both organic, proteinaceous compounds, such as enzymes, as well as non-proteinaceous organic-metal compounds that degrade reactive oxygen species or reactive nitrogen species in the locale of the sensor. In this catalytic degradation process, such a reactive species moves through a metabolic pathway in which it is a reactant. In this manner, the concentration of such a reactive species in solution may be reduced. According to some aspects of the invention, catalytic agents engage reactive oxygen and nitrogen species of biological origin within the biofluid. Further, according to some aspects of the invention, that catalytic activity enhances the biocompatibility of sensors, more particularly, one or more aspects of biocompatibility that may manifest in the form of improvements in sensor performance. Improvement or enhancement of sensor performance may coincide or be associated with higher quality data, as determined by various statistical methods that evaluate internal consistency or agreement with data from other sources. Higher quality data may include, for example, data that are more accurate with respect to reference data from standard strip-reading sensors, data more reflective of actual systemic levels of analyte, or data that are more internally consistent and as such contain less noise. Enhanced sensor performance may also include a lengthening of the effective lifetime of a sensor, the effective lifetime being reflected in an extended period of the delivery of accurate data.

Embodiments of the invention include analyte sensors that may sample any of several bodily fluids or their derivatives, and may be placed in positions variously internal within the body, transcutaneously across the skin, or external to the body. The types of analyte sensor systems include transcutaneous sensing systems, microdialysis systems, cutaneous-port systems and fully implanted systems, merely by way of example. Functionally open cutaneous ports in the skin may be provided by various methods, such as propelled particles, laser photothermal burning, sonic disruption of stratum corneum, and reverse iontophoresis, merely by way of example.

Embodiments of the invention further include analyte sensors that detect the concentration of the analyte through any available transducing method, including electrochemical and viscosimetric mechanisms, merely by way of example. According to some aspects of the invention, sensing systems are generally applied to the continuous sensing of an analyte by virtue of their in vivo relation to the body, but are not limited to any particular biofluid to be sampled, by any particular position of the sensing mechanisms with respect to their position internal, transcutaneous, or external relative to the body, or by any particular transducing mechanism. A feature common to all embodiments of the invention, however, is a structural interface between a biofluid (a first fluid) being sampled, and a second fluid that actually engages or comes in contact with the transducing mechanism of the sensor. The second fluid is one that has passed through the interface, and as such is a derivative of the first fluid, whose composition, at least in part, is determined by the permeability features of the interface. All embodiments of the present invention include a biocompatibility-promoting catalytic agent in the locale of this structural interface.

This interface may be synthetic, such as a membrane or gel, or biological, as exemplified by a cutaneous site or wound, or any suitable combination thereof. In the case of a transcutaneous sensor, the interface is embodied in a synthetic membrane that covers the sensing surface. In the case of a microdialysis system, the interface is embodied in the microdialysis membrane of the system. In the case of a cutaneous port system, whether created by propelled particles, a laser, or ultrasound, or through reverse iontophoresis, the interface is the cutaneous site or wound through which fluid has moved from the interstitium to the post-biological space outside the body. In the case of an iontophoretic system, the interface is the site on the skin that is exposed to the iontophoretic current, and through which fluid and solute then pass. In some cases a combination of biological and synthetic elements may constitute the operational interface. For example, in the case of a transcutaneous sensor, the full extent of the interface between (1) the biofluid, the undisturbed interstitial fluid and (2) the biofluid derivative that actually contacts the sensing surface can be considered to include not only the synthetic protective membrane over the sensing surface, but also the wound site within the skin that develops in the immediate vicinity of tissue into which the sensor has been inserted.

The first fluid can be any definable biofluid, such as blood or interstitial fluid. The second fluid or biofluid derivative varies in composition according to specifics of the sensing technology and the interface. In the case of a transcutaneous system, the biofluid is interstitial fluid, the interface is the membrane covering the subcutaneously-located sensor surface, and biofluid derivative is the filtrate that penetrates the membrane to contact the sensing surface. In the case of a microdialysis system, the biofluid is interstitial fluid, the interface is the subcutaneously-located dialysis membrane, and the biofluid derivative is the dialysate that contacts the sensing surface of an external sensor. In the case of cutaneous port systems, the biofluid is interstitial fluid, the interface is the cutaneous surface or the cutaneous wound, and the biofluid derivative is the wound fluid exuded out of the body, which then ultimately contacts the sensing surface of a sensor placed on the skin. In the case of reverse iontophoretic systems, the biofluid is interstitial fluid, the interface is the site on the skin that is subjected to current, and across which solute-containing fluid is driven, and the biofluid derivative is the solute-containing fluid that contacts the sensing surface on a sensor attached to the skin.

The catalytic agents, or more particularly, the organic-metal catalysts of the present invention, catalyze the degradation of reactive oxygen species and reactive nitrogen species, such as superoxide, hydrogen peroxide, and peroxynitrite, by way of example. Examples of such catalysts include superoxide dismutase/catalase catalysts, including catalytic enzymes and non-proteinaceous mimics of such enzymes. One particular example of a superoxide/dismutase catalyst is manganese 5,10,15,20-tetra(4-pyridyl)-21H,23H-porphine chloride (MnTPyP). Such a catalyst may be incorporated into a membrane that covers the sensing surface of a transcutaneous electrochemical sensor, or incorporated into the dialysis membrane of microdialysis-based sensing systems. As a result of its presence in the locale of the interface between the biological fluid and the sensing mechanism, the catalyst reduces the local concentration of reactive oxygen species, such as those mentioned above. While this invention is not bound by any proposed theory, it is thought that reactive oxygen species are present in the locale of the interface by virtue of metabolic activity of cells of the immune system, such as neutrophils, which are generally engaged in the initial phases of a foreign body response to the presence of the sensor. The reactive oxygen species in the locale of sensors may have effects that are deleterious to the sensor and may also further accelerate the recruitment of immune cells to the sensor site. The reactive oxygen species may further have effects on the metabolism of other cells in the locale, which may create local areas that are depleted of glucose, which, in turn, would disconnect local glucose values from systemic glucose values. Through the action of the superoxide dismutase/catalase catalysts and the consequent reduction of local concentrations of reactive oxygen species, the sensor may be rendered more biocompatible and its performance may be improved. Examples of enhanced sensor performance include a decrease in failure rate, an increase in operating lifetime, a decrease in the level of signal-interfering noise, and the prevention or decrease in incidence of spurious hypoglycemic incident reporting, by way of example.

These and various other aspects, features and embodiments of the present invention are further described herein.

BRIEF DESCRIPTION OF THE DRAWINGS

A detailed description of various aspects, features and embodiments of the present invention is provided herein with reference to the accompanying drawings, which are briefly described below. The drawings are illustrative and are not necessarily drawn to scale. The drawings illustrate various aspects or features of the present invention and may illustrate one or more embodiment(s) or example(s) of the present invention in whole or in part. A reference numeral, letter, and/or symbol that is used in one drawing to refer to a particular element or feature may be used in another drawing to refer to a like element or feature.

FIG. 1 depicts a sensing system where an upstream biofluid, and a downstream derivative of the biofluid are separated by a porous or partially-permeable interface with a catalytic agent disposed in the locale thereof, and the biofluid derivative comes into contact with the transducing apparatus of an analyte sensor.

FIG. 2A is a schematic, side-view illustration of a portion of a two-electrode glucose sensor having a working electrode, a combined counter/reference electrode, and a dip-coated membrane that encapsulates both electrodes. FIGS. 2B and 2C are schematic top- and bottom-view illustrations, respectively, of the portion of the glucose sensor of FIG. 2A. Herein, FIGS. 2A, 2B and 2C may be collectively referred to as FIG. 2.

FIG. 3A depicts a typical structure of a section of an analyte-diffusion-limiting membrane with a catalytic agent incorporated therein. FIG. 3B is an illustration of a membrane similar to that shown in FIG. 3A, except that a specific superoxide dismutase catalyst, manganese 5,10,15,20-tetra(4-pyridyl)-21H,23H-porphine chloride, is shown covalently incorporated therein.

FIGS. 4A and 4B, together, depict a transcutaneous electrochemical sensor. FIG. 4A is a perspective view of a fully fabricated sensor as it would be seen partially implanted into the skin, and FIG. 4B is an expanded and cutaway view of a sensor insertion tip, showing a membrane, enhanced with a catalytic agent, covering a sensing layer.

FIG. 5 is a graph of electrical current versus glucose concentration for electrochemical sensors having glucose-diffusion-limiting membranes that are enhanced with a catalytic agent.

FIG. 6 is a graph of glucose concentration versus time for a human subject over three days, as reported by two continuously operating, transcutaneous sensors. One sensor has a conventional membrane; the other has a membrane containing a superoxide-dismutase/catalase catalyst, MnTPyP. Intermittent readings obtained manually from a strip reading glucose meter are also shown.

FIG. 7 depicts a microdialysis-based sensing system with a catalytic agent associated with the membrane.

FIGS. 8A and 8B, together, schematically illustrate a cutaneous port-based sampling system in which a catalytic agent is disposed between a biofluid and a biofluid derivative. FIG. 8A illustrates a method of creating a cutaneous port in the skin and an associated system. FIG. 8B schematically illustrates a method of sampling wound fluid from such a cutaneous port and an associated system.

FIG. 9 depicts a cutaneous-port-based sampling system for an external sensor, in which the port comprises an iontophoretic site, and in which a catalytic agent is disposed between the biofluid and the biofluid derivative.

FIG. 10A depicts the head of a fully implantable analyte sensing system in which a catalytic agent is disposed in the locale of an interfacing membrane between biofluid and the biofluid derivative. FIG. 10B is schematic cross sectional view of a sensing region of the head. FIGS. 10A and 10B may be collectively referred to as FIG. 10.

DESCRIPTION OF THE INVENTION

1. Various Conventions and Terms

In the description of the invention herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms shown in quotation marks below are described to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily fluids, or sensor designs or usages, unless implicitly or explicitly understood or stated otherwise, as such may vary.

A "biofluid", or biological fluid, is any bodily fluid that exists physiologically within the bounds of the living body, such as, for example, whole blood (arterial, venous, or capillary), interstitial fluid, or cerebrospinal fluid. A "derivative" of a biofluid, or a "biofluid derivative" is a fluid derived from a biofluid by, for example, passage through an interface, such as dialysis membrane to yield a dialysate, or by passage through a protective membrane to yield a filtrate. The exudation of fluid through a biological interface, such as a cutaneous port at the site of a disruption in skin, is a fluid of biofluid origin that has left the bounds of a living body, is no longer a part of the biology of the subject body, is changed in some way during and as a result of its passage out of the body, and as such is also a derivative of a biofluid.

"Biocompatibility" is a property of a material that allows it to be compatible with the host biological environment with which it is in contact. Biocompatible material does not provoke a substantial or apparent foreign body response (which involves the immune system's recognition of non-self), or a substantial or apparent wound-healing response (which may not involve the immune system), the two of which together can contribute to the full biological response to the intrusion of a foreign body. This description of biocompatibility is not absolute, as the term can serve as a comparative descriptor, or can serve as a functional descriptor, such that it describes a compatibility sufficient to allow a material or device to perform its intended function within the host, for example. To some extent biocompatibility is described in terms of the negative, i.e., by the substantial or apparent absence of biological incompatibility. "Biological incompatibility" is used commonly even without an understanding of the specifics of the physical or chemical features responsible for the incompatibility and/or an understanding of the details of the biological response to the foreign body. Accordingly, the meaning of the biocompatibility is flexible, and becomes more specific according to the specifics of the context.

"Catalase" (systematic name: hydrogen-peroxide:hydrogen-peroxide oxidoreductase) is an enzyme that catalyzes the decomposition or "dismutation" of 2 molecules of hydrogen peroxide to yield water and molecular oxygen. The hydrogen peroxide substrate of this reaction is a product of a superoxide dismutase reaction, as described below under "superoxide dismutase".

An "organic-metal catalytic agent" describes a compound that facilitates a chemical reaction or reactions. Catalytic agents increase the flux of compounds through metabolic pathways, are themselves, unchanged by the reaction they facilitate, and are thus available for further activity. A single catalytic agent may affect the flux through metabolic pathways at a single step, or at multiple steps, and it may affect flux through multiple pathways. Organic-metal catalytic agents described herein include metal-containing enzymes, which are proteinaceous catalysts, as well as non-proteinaceous, organic-metal compounds that are catalytic and mimic the action of particular enzymes. Catalytic agents that improve the biocompatibility (see above) of a device may be referred to as biocompatibility-promoting catalytic agents.

A "counter electrode" refers to (a) a counter electrode or (b) a counter electrode that also functions as a reference electrode (i.e., a counter/reference electrode).

A "crosslinker" is a molecule that contains at least two reactive groups capable of linking at least two molecules together, or linking at least two portions of the same molecule together. Linking of at least two molecules is called intermolecular crosslinking; linking of at least two portions of the same molecule is called intramolecular crosslinking. A crosslinker having more than two reactive groups may be capable of coincidental intermolecular and intramolecular crosslinkings.

An "electrochemical sensor" is a device configured to detect the presence of or measure the concentration or amount of an analyte in a sample via an electrochemical oxidation or reduction reaction. Typically, the reaction is transduced to an electrical signal that is correlated to an amount or concentration of analyte. "Electrochemical" describes a method of transducing a concentration of analyte to an informative signal. Other methods of transduction include, for example, optical and viscosimetric methods. While the description herein includes an exemplary embodiment that is electrochemical in nature, the invention is not limited in terms of the transduction method employed.

A "heterocyclic nitrogen group" refers to a generally carbon-based cyclic structure containing an sp2-hybridized nitrogen integrated within a ring of the structure.

"Iontophoresis" refers to the application of an electric current to cause the electro-osmotic transport of fluid and solutes contained therein across the skin. "Reverse iontophoresis" refers to the process when it is being operated so as to extract an analyte-containing fluid of biological origin outwardly from the skin. In the context of this invention, such iontophoretic biofluid derivative is then provided as a sample to a sensor on the surface of the skin.

An "in vivo analyte sensor" is a sensor that is designed for placement in a body or on a body, with varying degrees of invasiveness, but having in common a continuous exposure to biofluid. In vivo sensors do not require, as is the case with ex vivo sensors, a separate step or steps by which a biofluid sample is taken from the body and conveyed to an external device for a discrete sample-specific sensing event. An in vivo sensor, for example, may be fully or partially implanted in the body and exposed to a biofluid, inserted across the skin such that a subcutaneous biofluid contacts the sensor, or placed on the surface of the skin such that an exuded biofluid contacts the sensor. In vivo sensors transduce the presence of analyte into an informative signal by any of a variety of methods, including electrochemical, optical, piezoelectric, and viscosimetric methods.

"Interface" describes an intervening structure between (1) a space in a body wherein a biofluid exists in its native form, and (2) a space in which a derivative of the biofluid (derivative by virtue of having passed through the interface) comes into contact with a transducing element or mechanism of the sensor, such as a sensing surface of an electrochemical sensor. The interface may be embodied in various forms, including such forms as a membrane over the sensing surface of a sensor, a microdialysis membrane, or the surface of a cutaneous wound which functions as a transcutaneous port, allowing the egress of a wound fluid.

"Interstitial fluid," also known as "extracellular fluid," refers to the fluid in the body that occupies the space between cells. This fluid is distinct from intracellular fluid, as well as from the fluid or plasma portion of blood contained within the vessels of the circulatory system. A transcutaneously-placed glucose sensor is exposed to interstitial fluid.

A "low-glucose-reading incident" describes an occurrence of a glucose reading by a sensor that is lower than a value that would be reasonably expected by a qualified observer exercising judgment based on a view of the overall medical context. Such a glucose reading is considered spurious in that it may not accurately reflect the systemic blood glucose level.

A "membrane solution" is a solution that comprises components for crosslinking and forming the membrane, such as a modified polymer containing heterocyclic nitrogen groups, a crosslinker, and a buffer or an alcohol-buffer mixed solvent. A "catalyst-enhanced membrane solution" is a membrane solution that includes a catalytic agent, such as an enzyme or a mimic thereof.

"Microdialysis" refers to a sampling technology used in a biosensor system wherein a catheter incorporating a thin dialysis tube section is inserted subcutaneously into a body. The tube is constructed of a membrane partially permeable to solutes, through which an isotonic solution is circulated. During the circulation cycle, the concentration of glucose within the isotonic solution equilibrates with the glucose concentration within the surrounding interstitial fluid. This solution or dialysate becomes the sample fluid that is contacted to a sensor on the skin. The "micro" of microdialysis simply refers to the size of the tubing, in terms of diameter or volume/length, which is small compared to that of standard research or preparative dialysis tubing. Simply as an example of dimensions, the dialysis membrane of the CMA 60 microdialysis catheter of CMA Microdialysis AB (Solna, Sweden) has a length of 30 mm and a diameter of 0.6 mm, with a molecular weight cut-off (i.e., pore size) of approximately 20,000 Daltons.

A "mimic" or "non-proteinaceous mimic" refers to a non-proteinaceous compound that has a catalytic activity like that of a known enzyme, and thus is a "mimic" of that enzyme. The non-proteinaceous compound may comprise a metallic component and an organic component, wherein a metal ion or atom of the metallic component and a nonmetallic ion, molecule, portion, or ligand of the organic component form a union. Such a non-proteinaceous compound may be referred to as a metal-nonmetallic or nonmetallic-metal compound, a metal-organic or organic-metal compound, and/or the like, and is sometimes referred to as an organometallic compound, as that term is often loosely used or as that term is strictly used. When the union is coordinative or complexing in nature, such a non-proteinaceous compound may be referred to as a coordination compound, a complex compound, a metal-nonmetallic or nonmetallic-metal complex or coordination compound, a metal-organic or organic-metal complex or coordination compound, and/or the like. When the union is in the form of a direct metal-to-carbon attachment, whether of a coordinative, complexing, or other nature, the non-proteinaceous compound may be referred to as an organometallic compound, as that term is strictly used. The non-proteinaceous compound may comprise any suitable metal, such as any suitable metal in any of Groups 3 through 12 (new notation) or IB through VIIB and VIII (CAS notation) of the Periodic Table of the Elements or any suitable metal in the family of transition metals, such as manganese, iron, copper, or zinc, merely by way of example.

"Peroxidase" (systematic name: donor:hydrogen-peroxide reductase) is an enzyme that catalyzes the reduction of hydrogen peroxide to yield water. The reaction catalyzed by peroxidase may be expressed as follows: donor+$H_2O_2$=oxidized donor+$2H_2O$. The hydrogen peroxide substrate of the reaction is a product of a superoxide dismutase reaction, as described below under "superoxide dismutase."

"Polyvinylimidazole" refers to any of poly(1-vinylimidazole), poly(2-vinyl-imidazole), or poly(4-vinylimidazole).

"Polyvinylpyridine" refers to any of poly(4-vinylpyridine), poly(3-vinylpyridine), or poly(2-vinylpyridine), as well as any copolymer of vinylpyridine and a second or a third copolymer component.

A "reactive group" is a functional group of a molecule that is capable of reacting with another compound to couple or covalently bind at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzo-triazolyl, or aryl substituted by electron-withdrawing groups, such as sulfo, nitro, cyano, or halo groups; or carboxylic acids activated by carbodiimides.

"Reactive species" describes a free radical or other molecule that is easily converted to a free radical or is a powerful oxidizing agent. "Reactive oxygen species" (or ROS) refers to at least one of a superoxide ($O_2^-$), hydrogen peroxide ($H_2O_2$), hypochlorous acid (HOCl), and hydroxyl radical (OH.). Synonymous terms include "reactive oxygen metabolite" (ROM) and "reactive oxygen intermediate" (ROI). "Reactive nitrogen species" (or RNS) refers to nitric oxide (NO) of various redox states and related species including at least one of nitric oxide radical (NO.), nitric oxide nitrosonium cation ($NO^+$), and nitroxyl anion ($NO^-$), and peroxynitrite ($ONOO^-$). Synonymous terms include "reactive nitrogen metabolite" (RNM) and "reactive nitrogen intermediate" (RNI). For a review of these reactive oxygen and nitrogen species in the context of neutrophil biology, see J. Paul Robinson and George F. Babcock (eds), *Phagocyte Function: A Guide for Research and Clinical Evaluation*, ISBN 0471123641, John Wiley (1998).

A "redox mediator" is an electron-transfer agent for carrying electrons between an analyte, an analyte-reduced or analyte-oxidized enzyme, and an electrode, either directly, or via one or more additional electron-transfer agents. A redox mediator that includes a polymeric backbone may also be referred to as a "redox polymer."

A "reference electrode" is (a) a reference electrode or (b) a reference electrode that also functions as a counter electrode (i.e., a counter/reference electrode), unless otherwise indicated.

A "transducing mechanism", a "transducing apparatus", or a "transducer" describes at least one element of a sensor that is directly involved in identifying an analyte and its concentration, and from that information, generating a signal informative of this information. Transducing mechanisms vary according to the physical and/or chemical method and apparatus by which the analyte is recognized and by which the concentration of the analyte is determined.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —$NH_2$, alkylamino, dialkyl-amino, trialkylammonium, alkanoylamino, arylcarboxamido, hydrazino, alkylthio, alkenyl, and reactive groups.

"Superoxide dismutase" (SOD) refers to an enzyme that catalyzes the dismutation of superoxide to yield oxygen and hydrogen peroxide. The reaction catalyzed by superoxide dismutase may be expressed as follows: $2O_2.- + 2H^+ = O_2 + H_2O_2$. The hydrogen peroxide product of the reaction is a substrate for catalase and/or peroxidase.

A "superoxide-dismutase/catalase catalyst" refers to a catalyst, whether an enzyme or an enzyme mimic, that possesses the catalytic activity of either superoxide dismutase or catalase, to any degree, or the catalytic activities of both superoxide dismutase and catalase, to any degree. The term, superoxide-dismutase/catalase catalyst, encompasses a preferred embodiment in which a catalytic agent that catalyzes the dismutation of superoxide also catalyzes the decomposition of hydrogen peroxide, and vice versa. The term, super-oxide-dismutase/catalase catalyst, also encompasses embodiments in which an agent catalyzes the dismutation of superoxide, but not the decomposition of hydrogen peroxide, and embodiments in which an agent catalyzes the decomposition of hydrogen peroxide, but not the dismutation of superoxide.

A "superoxide-dismutase/catalase mimic" refers to an enzyme mimic that possesses the catalytic activity of one or more of the superoxide dismutase and catalase enzymes, to any degree, or the catalytic activities of both superoxide dismutase and catalase, to any degree. The term, superoxide-dismutase/catalase mimic, encompasses a preferred embodiment in which a catalytic agent that catalyzes the dismutation of superoxide also catalyzes the decomposition of hydrogen peroxide, and vice versa. The term, superoxide-dismutase/catalase mimic, also encompasses embodiments in which a catalytic agent catalyzes the dismutation of superoxide, but not the decomposition of hydrogen peroxide, and embodiments in which a catalytic agent catalyzes the decomposition of hydrogen peroxide, but not the dismutation of superoxide. Mimics that catalase the superoxide dismutase and catalase reactions may catalyze other reactions as well, such as peroxynitrite decomposition.

"Transcutaneous" refers to the site or location or nature of a biosensor when a portion of the biosensor is placed across the cutaneous layer, such that one portion of the biosensor remains external to the skin, and another portion of the biosensor is inserted into the subcutaneous space, and in contact with interstitial fluid. "Transcutaneous" is also a descriptive term that may be applied to sensors of this type. Transcutaneous sensors are considered to be partially implanted in the body, in contrast to sensors that are fully implanted within the body.

2. Sensing of Derivatives of Biofluid Samples from the In Vivo Environment

2a. Recognition that Aspects of the In Vivo Environment, Such as the Cellular Immune System and its Metabolism, May be Pertinent to the Operation of an Analyte Sensor Various types of biosensors have been designed to operate partially or wholly in a living body. As these biosensors are exposed to the chemistry and biology of the body, it is now theorized that various chemical and biological factors may complicate specific aspects of their operation or performance that may manifest in subtle ways. For example, an implanted biosensor is typically completely enclosed within a body and remains within the body for a period varying from weeks to many months. Such an implanted sensor may have longer-term effects in the region surrounding the implantation site, such as the effects of the immunologic reaction to the sensor as a foreign body, including the related vascular processes, biofouling, and fibrotic sequelae at the site of foreign presence. In cases where such clear and apparent biological response to the presence of a sensor occurs, the performance of the sensor might be expected to be compromised. However, as theorized above, the highly sensitive sensor processes could be compromised before such obvious manifestation of biological response, or even in its apparent absence. Similarly, a transcutaneous sensor may be subject to subtle biological or biochemical interference in ways that do not coincide with the lengthy timeline marked by vascular processes, biofouling, and fibrosis. A transcutaneous biosensor, in contrast to a fully implanted sensor, is much less invasive, as only a portion of the sensor intrudes into the subcutaneous space, and that portion resides there only for a period on the order of about three to about five days. Even within this relatively short period, however, the early phases of the immune system response to the inserted portion of the sensor are activated; as neutrophils, the main phagocytic leukocytes in the blood, are quickly recruited to the site, whereupon, it is now theorized, they may have significant effects on sensor performance.

At the site of foreign intrusion, neutrophils release destructive enzymes and oxidants to damage the intruder, while at the same time, they attempt to physically engulf and devour it.

The released oxidants are derived from hydrogen peroxide, superoxide radicals, nitric oxide and chloride, the former two of which, at least, may act to attract further neutrophils and thereby accelerate their own respective accumulation. The released oxidants include hydroxyl radicals, formed through the reaction of hydrogen peroxide with reduced transition metal cations or their complexes; peroxy-nitrous acid, formed of nitric oxide and superoxide radicals; and hypochlorite, formed of hydrogen peroxide and chloride. The resulting oxidant cocktail is strong, able to oxidize most organic chemicals and to provide a local antiseptic effect that is generally beneficial at a site of a potentially infectious intrusion. A broad review of this subject appears in eds. J. P. Robinson and G. F. Babcock, *Phagocyte Function: A Guide for Research and Clinical Evaluation*, John Wiley, ISBN 0471123641 (1998), and particularly in Chapter 9 thereof, J. P. Robinson, *Oxygen and Nitrogen Reactive Metabolites and Phagocytic Cells*, p. 217.

As noted in the background, in vivo sensors have been observed to report glucose values that are considered to be spuriously low. In view of these observations, and in view of what is known about the biology of neutrophils, it is possible to formulate theories (without being bound by such theories) that hold neutrophils at least partially responsible for affecting the performance of a glucose sensor and creating spurious results by several mechanisms. For example, newly recruited neutrophils are known to be in the midst of an "oxidative burst" that is characterized by high rates of internal metabolic activity, as well as extensive release of superoxide as part of their anti-infective effort. Metabolically active cells of the immune system, in high concentration, may deplete the local environment of the glucose they consume for energy. Another possible explanation for low glucose readings focuses on the presence of neutrophil-originating reactive oxygen species. Superoxide gives rise to hydrogen peroxide, which in addition to playing an antiseptic role, may have further effects on the internal metabolism of local tissue. Hydrogen peroxide may, for example, increase the consumption of glucose by local cells via the pentose phosphate pathway (also known as the HMP shunt), an effect mediated by intracellular glutathione levels. Briefly, according to this proposition, hydrogen peroxide oxidizes glutathione to its oxidized dimer form, oxidized glutathione oxidizes NADPH to NADP+, and finally NADP+ oxidizes glucose-6-phosphate to ribulose-5-phosphate in the first step of the pentose phosphate pathway. The result of this glutathione-mediated effect would be to accelerate the intracellular glucose metabolism, and such affected cells would then consequently draw upon and deplete the local extracellular concentration of glucose. Local glucose depletion, by either of these processes, could compromise the value of glucose sensing data, as however accurate the data may be in a very local sense, the data may not be reflective of the clinically relevant level of glucose in the bloodstream.

It is now also theorized that accumulated neutrophils, in their attempt to engulf the sensing surface, may physically cover it to the extent that the sensor no longer has effective contact with the surrounding interstitial fluid. This latter theory, particularly, is consistent with the observation that low glucose readings often occur during periods of stillness, such as sleep, and the recovery of those glucose readings to normal upon body movement that may either disturb the accumulated neutrophils, or more generally, stir the stagnant interstitial fluid surrounding the sensor. Further, in terms of the panoply of effects that neutrophils may have on glucose sensor data, it is now theorized that the oxidants released by the neutrophils in an immune system response may have direct disrupting effects on the electrochemistry of the sensor.

An immune system response, such as that described above, typically results in inflammation. One particular approach to controlling inflammation associated with the presence of long-term device implants, such as cardiac stents, replacement joints and the like, involves the use of superoxide dismutase (SOD) to consume accumulated superoxide. Superoxide, a product of neutrophil metabolism, as well as an attractor of neutrophils and other cells of the immune system, is a highly reactive species that gives rise to other oxygen metabolites. Superoxide generation often occurs under conditions which nitric oxide is also being generated. The two species can then combine to form peroxynitrite, a species that can be classified as either a reactive oxygen species or a reactive nitrogen species, which then has further inflammatory consequences. The reaction catalyzed by the SOD enzyme, known as "dismutation" of superoxide, consumes two superoxide ions and two hydrogen ions to yield molecular oxygen and hydrogen peroxide, per the following reaction: $O_2^- + O_2^- + 2H^+ \rightarrow O_2 + H_2O_2$. As such, the SOD enzyme would appear to be capable of catalyzing the removal of at least some of the superoxide that is present at a site of neutrophil metabolism.

The SOD enzyme has been shown to be effective in reducing inflammation in the context of the vascular system (J. M. McCord, *Superoxide Dismutase: Rationale for Use in Reperfusion Injury and Inflammation*, Free Radical Biol. Med. 2: 307-310, 1986; and V. R. Muzykantov, *Targeting of Superoxide Dismutase and Catalase to Vascular Endothelium*, J. Control Release, 71: 1-21, 2001), leukocyte biology (J. F. McCord, *Superoxide Production in Human Disease*, in ed. A. Jesaitis and E. Dratz, *Molecular Basis of Oxidative Damage by Leukocytes*, CRC Press 1992, ISBN: 0849363632, pp. 225-239), and in the brain (Chan et al., *Protective Effects of Liposome-Entrapped Superoxide Dismutase on Posttraumatic Brain Edema*, Ann. Neurol. 1987; 21, 540-547; Chan et al., *Free Fatty Acids, Oxygen Free Radicals, and Membrane Alterations in Brain Ischemia and Injury*, in ed. Plum et al., *Cerebrovascular Diseases*, Raven Press, New York 1985, 161-171). The ubiquity of this enzyme suggests the broad significance that controlling the local concentrations of superoxide has in regulating physiological homeostasis as well as the role superoxide plays in inflammatory processes. Various forms of the SOD enzyme are known; each includes a transitional metal component that is important in the enzyme's catalytic activity. For example, a manganese-containing form of the enzyme is found in mitochondria, a copper- or zinc-containing form of the enzyme is found in plasma and in extracellular fluid, and an iron-containing form of the enzyme is found in anaerobic prokaryotes (D. P. Riley, *Functional Mimics of Superoxide Dismutase Enzymes as Therapeutic Agents*, Chem. Rev. 1999, 99, 2573-2587).

Non-proteinaceous, mimics of superoxide dismutase (SOD mimics) have also been shown to reduce inflammation (Weiss et al., *Manganese-Based Superoxide Dismutase Mimetics Inhibit Neutrophil Infiltration In-Vivo*, J. Biol. Chem. 1996; 271, 26149-26156). For example, a class of manganese- or iron-complexes of nitrogen-containing, fifteen-membered, macrocyclic ligands has recently been shown to have the catalytic activity of SOD, and to be effective, when attached to the surface of small plastic subcutaneous implants, in reducing the inflammation caused by implantation (U.S. Pat. No. 6,525,041 of Neumann et al., filed on Mar. 14, 1996; Published PCT Application, International Publication No. WO 00/72893 A2 of Omberg et al., filed on May 26, 2000; U.S. Patent Application No. 2004/0110722A1 of Omberg et al., filed Nov. 5, 2003, and U.S. Patent Application No. 2004/0116332A1 of Omberg et al., filed Nov. 5, 2003, and Udipi et al., J. Biomed. Mater. Res. 2000, 51(4), 549-560). Articles providing an overview of SOD mimics include those of Riley, *Functional Mimics of Superoxide Dismutase Enzymes as Therapeutic Agents*, Chemical Reviews 1999, 99, 2573-2587, and Salvemini et al., *Superoxide Dismutase Mimetics*, Pulmonary Pharmacology and Therapeutics 2002, 15, 439-447, and patents disclosing such mimics include U.S. Pat. Nos. 5,610,293 and 6,084,093 of Riley et al., filed on May 16, 1995, and U.S. Pat. No. 6,214,817 of Riley et al., filed on Sep. 16, 1999.

Yet another enzyme, catalase, and non-proteinaceous mimics of catalase, may have ameliorative effects on inflammation. Like superoxide, hydrogen peroxide is a reactive oxygen species, and one that may further attract neutrophils. The reaction catalyzed by catalase, namely, the decomposition of hydrogen peroxide, consumes two molecules of hydrogen peroxide to produce two molecules of water and one molecule of oxygen gas. As such, the catalase enzyme, and mimics thereof, would appear to be capable of catalyzing the removal of at least some of the biologically-derived hydrogen peroxide at the site of the intrusion of a sensor, or a portion of a sensor. More broadly, enzymes that catalyze the decomposition of hydrogen peroxide make up a large class and come from a variety of sources, such as microbial, plant, and animal cells. For example, according to the International Union of Biochemistry, a large group of oxidoreductase enzymes includes a subgroup (EC 1.11) of peroxidases that act on hydrogen peroxide as electron acceptors. These peroxidases generate water and an activated donor molecule when acting on hydrogen peroxide. Catalase (hydrogen peroxide oxidoreductase, EC 1.11.1.6) is but one of these peroxidases that more specifically generates water and oxygen when acting on hydrogen peroxide. Further, some peroxidases (sometimes referred to as catalase-peroxidase) from various microorganisms, such as *Penicillium simplicissimum*, exhibit both peroxidase and catalase activity. Superoxide-dismutase/catalase catalysts encompass any of the foregoing peroxidases, and any non-proteinaceous mimic thereof. According to the present invention, these superoxide dismutase/catalase catalysts act to deplete concentrations of the metabolite, hydrogen peroxide, in useful ways, such as in biosensor applications, as further described herein.

Some non-proteinaceous, organic-metal compounds have been shown to catalyze both superoxide dismutation and hydrogen peroxide decomposition. These compounds may be referred to as "superoxide dismutase/catalase mimics." Eukarion, Inc. of Bedford, Mass. has developed such mimics, termed "synthetic catalytic scavengers," and has provided references to publications concerning same (such as S. R. Doctrow et al., *"Salen Manganese Complexes" Combined Superoxide Dismutase/Catalase Mimics with Broad Pharmacological Efficacy*, Advances in Pharmacology 1996, 38, 247-269) on its website (http://www.eukarion.com/). Patents and a patent application that disclose compounds having such dual catalytic activity include U.S. Pat. Nos. 5,202,317 and 5,217,966 of Bruice, filed on Sep. 13, 1990 and Jan. 17, 1992, respectively; U.S. Pat. No. 6,403,788 of Meunier et al., filed on Jul. 11, 2000, U.S. Pat. No. 6,541,490 of Campbell et al., filed on Nov. 27, 2000, and U.S. Pat. Nos. 6,573,257 and 6,589,948 of Malfroy-Camine et al., filed on Apr. 4, 2000 and Nov. 28, 2000, respectively; and U.S. Patent Application Publication No. U.S. 2003/0118577A1 of Weill et al., filed on Feb. 3, 2003.

According to the present invention, various catalytic agents are used in connection with biosensors that are used to measure analyte concentration, such as glucose concentration, in biofluid derivatives with which the biosensor is in contact. The catalytic agents catalyze the removal of at least some of the harmful reactive metabolites, such as reactive oxygen species or reactive nitrogen species, or more particularly, such as superoxide or hydrogen peroxide, that may be present in the vicinity of the biosensor. Hydrogen peroxide, in particular, could have a biological source, or be locally present through its production by the chemical processes of an electrochemical sensor. However, while not being bound by theory, in general, such reactive species are theorized to have a biological source, such as various cells of the immune system, and more particularly, phagocytic cells of myeloid lineage, such as neutrophils. As demonstrated herein, biosensors equipped with such catalytic agents are better able to handle the complex and variable biological environment that is associated with in vivo biosensing. While such biosensors are for the most part described in relation to transcutaneous, amperometric glucose sensors herein, it will be understood that the present invention encompasses the use of catalysts in connection with other analyte sensors.

2b. Recognition of the Commonality of the Presence of an Interface Between the Biofluid and the Transducing Mechanism of In Vivo Analyte Sensors that Provides a Site for the Disposition of a Biocompatibility Promoting Catalytic Agent It has been observed that various types of in vivo analyte sensors, regardless of the specifics of their placement in or on a body, and regardless of their method of transducing an analyte concentration into an informative signal, commonly have an interface that is breached by a biofluid before an analyte-containing fluid gains access to the transducing mechanism, as for example, the sensing surface of an enzyme-based electrochemical sensor. The interface, in this context, refers to a demarcating structure or set of structures between (1) a space in which a physiological fluid or biofluid exists in its native form within the living body, and (2) a space in which a second fluid, a derivative of the biofluid, comes into contact with the transducing apparatus of the sensor. Such a structural interface can either be synthetic, biological, or a combination or intermingling of the two. Regardless of its physical composition, the interface is, in its entirety, partially porous or selectively permeable, such that it bars the free flow of the native biofluid, permits a limited flow of the biofluid and a subset of its solutes, and generally excludes the passage of particulates, such as whole cells, platelets, or suspended components of the biofluid, such as lipoproteins: In the context of an in vivo sensor, benefits of the interface may include (1) an exclusion of interferents from the sensing surface that would otherwise compromise the intended specificity of the sensor to the analyte of interest, (2) a lowering of analyte concentrations to levels that can improve linearity of the sensor response, and (3) an improvement in some aspect of the biocompatibility of the sensor, as it is configured in situ.

The form of the interface varies with the type of the continuous in vivo sensor. For example, in the case of transcutaneous electrochemical sensors, the interface can be a membrane covering the sensing surface, as described in U.S. patent application Ser. No. 10/146,518 of Mao et al., filed on May 14, 2002, the corresponding U.S. Patent Application Publication No. U.S. 2003/0042137A1 of Mao et al., published on Mar. 6, 2003, and U.S. Provisional Patent Application No. 60/291,215 of Mao, filed on May 15, 2001. In the case of microdialysis-based transcutaneous sensors, the dialysis membrane, itself, is an interface between the native biofluid and the derivative fluid, the dialysate, which comes in contact with the transducing apparatus of the externally-attached sensor.

In the case of cutaneous, port-type systems, there may be one or more structures that collectively constitute the interface between the native biofluid, generally interstitial fluid, and the fluid that ultimately contacts the transducing mechanism of the sensor. The surface of the skin, whether it is, for example, a wound, or an iontophoretic site, is an interface of biological form. Additionally, there may be synthetic membranes, for example, that cover the sensing surface of an electrochemical sensor, and function as another interface. The interface may be appropriately viewed as the totality of structures (biological and synthetic) that are interposed between the native biofluid and the biofluid derivative that finally makes contact with the transducing system of the sensor. Returning to the concept of the surface of the skin functioning as an interface, a cutaneous port or wound is not simply a stable, free-flowing conduit for the escape of interstitial fluid from the body, but rather a site physiologically and structurally distinct from the surrounding tissue, that effects a selection on the fluid components that exude therefrom. The biological structures of wounds vary according to the nature and magnitude of the wound, and also are dynamic, as form and composition change over time. Wound structures may include extracellular components, such as extracellular matrix protein and clotting proteins such as fibrin, and wound structures further may contain cellular components drawn from the local population of dermal, epidermal, and cutaneous cells, and fibroblasts from local underlying connective tissue. References concerning cutaneous wound healing include *The Phases of Cutaneous Wound Healing*, Accession Information, vol. 5 (5), Mar. 21, 2003; *Cytokines in Wound Healing*, R & D Systems Catalog 2002 (Minneapolis Minn., also available at http://www.rndsystems.com/, under "Reviews and Tech Notes); A. J. Singer and R. Clark, *Cutaneous Wound Healing*, NEJM 341 (10) 738-746, Sep. 2, 1999; S. Cockbill, *Wounds: The Healing Process*, Hospital Pharmacist, vol. 9, 255-260, October 2002; Anderson, *Biological Responses to Materials*, Ann. Rev. Mater. Res. 31, 81-110, 2001; and V. Falanga, *Cutaneous Wound Healing*, ISBN 1853172049, published by Taylor & Francis Group, October 2001.

It has been recognized herein of the commonality of the presence of physical structures or sites, albeit of various form, in a disparate variety of continuously-sensing in vivo sensors that function as an interface between the sampled biofluid and the derivative fluid that actually contacts the transducing apparatus of the sensor. Further, it has been recognized herein that such an interface provides a site for the disposition of catalytic agents that may enhance the biocompatibility and consequent performance of such sensors, as described further below.

2c. Schematic Depiction of the Interface and its Utilization as a Site for the Disposition of Catalytic Agents The sensing of biological fluids by continuous in vivo sensing systems may be schematically depicted, as in FIG. 1, as involving two fluids 40 and 42 that are separated by an interface 30 that allows passage of a portion, as indicated by directional arrows, of the first fluid to create or contribute to the second fluid. Embedded within the interface 30 is an amount of catalytic agent 32 (indicated by asterisks). The first fluid or upstream fluid 40 is contiguous with a native biological fluid, whether it is arterial blood, capillary blood, venous blood, interstitial fluid, cerebrospinal fluid, or any other biological fluid within a living organism, and will be referred to simply as a biofluid. The second fluid or downstream fluid 42 is a fluid that has passed through the interface 30, and such fluid, accordingly, can be referred to as a biofluid derivative. This biofluid derivative 42 is the fluid that actually contacts the transducing apparatus 18 of an analyte sensor 10. In the case an enzyme-based electrochemical sensor, merely by way of example, the transducing apparatus comprises the sensing surface with an enzyme that recognizes and quantitatively responds to the presence of an analyte by generating an informative signal. This interface is generally porous with respect to the movement of water, and partially or selectively permeable with respect to solutes contained in the fluids, thereby creating a flow-through fluid that differs from the first fluid. Inasmuch as the fluid that passes through the interface constitutes the second fluid 42 that differs from the source biofluid, this second fluid can be referred to as a biofluid derivative. In the embodiments of the invention that follow, the volume of the second or derivative fluid may vary to considerable degree. For example, in the case of a microdialysis-based sensor, the biofluid derivative can be relatively large, comprising the microdialysate flow-through fluid admixed with the original bulk dialysis fluid. In other embodiments, as is the case with a transcutaneous electrochemical sensor with a membrane covering the sensing layer, the volume of the membrane filtrate is quite small, consisting of only of the fluid that has transited to the far side of a protective membrane, creating but a thin layer of fluid on the inner side of a protective membrane, against the sensing surface. Thus, even though the volume of the solution that penetrates through a protective membrane in the case of a transcutaneous electrochemical sensor is small, it still is a fluid, and a fluid whose solutes are derived from a native biofluid, and as such, analogous to the dialysate fluid that contacts the transducer of a microdialysis-based sensor system.

Embodiments of the present invention include a catalytic agent 32 associated with, or disposed in the locale of the interface, i.e., near enough to the interface that the catalytic agent alters the composition or population of chemical species that comprise the chemical environment surrounding the interface. A superoxide dismutase/catalase catalyst is an example of a suitable catalytic agent. Catalytic agents of this invention more generally include catalysts that degrade locally present reactive oxygen species or reactive nitrogen species, and as a result of such catalytic activity, may improve the biocompatibility and performance of the analyte sensor. The substrate of such catalytic agent or agents is the population of local reactants in the biofluid 40, and the ultimate result in terms of the changes in concentrations of reactants and products is reflected in the composition of the biofluid derivative 42, the whole of which has passed through the interface.

The interface 30, in its totality as a structure or combination of structures that separate the biofluid 40 from the biofluid derivative 42, may comprise not only the hardware of the manufactured sensor but also the biological elements or structures that serve and enable the operation of the sensor as it is implanted, or partially implanted in a living body. The operable interface that serves the implanted sensor, thus may be either synthetic and an integral part of the sensor itself, or it may be biological, or it may include both synthetic and biological elements. What follows now is a brief description of various types of analyte sensors, and how they relate in particular detail to the highly schematic representation of FIG. 1.

Sensors of a transcutaneous type are those that are inserted across the skin, with one portion penetrating into the subcutaneous space, and another portion remaining exposed on the surface of the skin, and as such are also considered to be partially implantable, or semi-invasive sensors. In the case of a transcutaneous electrochemical type of sensor, the biofluid 40 is interstitial fluid, the interface 30 may be a synthetic biocompatible membrane of at least one layer covering the transducer, in this case, the sensing surface, and the biofluid derivative 42 is a filtered subset of interstitial fluid that crosses the membrane to contact the sensing surface. In this case, the "subset" generally refers to a solute or solutes within the fluid and more specifically, can refer to a number of specific solute(s) and also to the concentrations of such specific solute(s). As shown in FIG. 1, the transducing apparatus 18 of the sensor is in contact with the biofluid derivative 42.

In the case of a microdialysis type of sensor (also a transcutaneous sensor), as it is configured in situ, the biofluid 40 is interstitial fluid, the interface 30 is the microdialysis membrane, and the biofluid derivative 42 is the microdialysate fluid, which ultimately contacts the transducing apparatus 18 of an external sensor.

In the case of a cutaneous port type of sensor, as it is configured in situ, the biofluid 40 is interstitial fluid, the surface of the cutaneous wound that defines the port functions as an interface 30, and biofluid derivative 42 is the wound fluid that exudes from the wound and is available to contact the sensing surface, or more generally the transducing apparatus 12. The sensing surface, or more generally the transducing apparatus 18 of the externally-placed sensor is in contact with the biofluid derivative 42.

In the case of an iontophoretic type of sensor, as it is configured in situ, the biofluid 40 is interstitial fluid, the operable interface 30 may be the surface of the cutaneous site that is defined by area through which weak current passes, and the biofluid derivative 42 is that subset of interstitial fluid and solute that crosses the skin and is available to contact the transducing apparatus 18 of a sensor configured on the surface of the skin. In this case, the "subset" generally refers to a solute or solutes within the fluid, and further can refer to a number of specific solute(s) and also to the concentration of such specific solute(s). The transducing apparatus 18 of the skin surface-placed sensor is in contact with the biofluid derivative 42.

In the case of a fully implanted in vivo sensor, the biofluid 40 may either be interstitial fluid, whole blood depending on the site of implantation, the interface 30 may be a biocompatible membrane covering the sensing surface, and the biofluid derivative 42 is a filtrate of the interstitial fluid or blood that crosses the membrane to contact the transducing apparatus 18 of the sensor.

The foregoing discussion of various examples of types of sensors, as they are configured, in situ, examples of their respective relevant fluids 40 and 42, and examples of their respective fluid-separating interfaces 30, as depicted in FIG. 1, are set forth in Table 1, below. In the embodiments described in sections to follow, and in the associated figures, parts are numbered in a manner that is generic and consistent with analogous parts having the same numeral, but with variations or component sections being denoted by a letter following the numeral. Sensors, for example, are identified by numeral 10, with a letter following the numeral to identify distinct sensors, or some major portion of a sensor, such as a head or a body. Similarly, all electrodes, regardless of their type (working, reference, or counter), polarity, or chemical composition are identified by numeral 29, transducers of any type are identified by numeral 18, and a transducing sensing layer of an electrochemical sensor is identified by numeral 18a. Similarly, interfaces are identified by the numeral 30, whether the interface is a synthetic membrane overlaying a sensing surface, a dialysis membrane, or a biological structure that is functioning as an interface. The catalytic agent associated with an interface is identified by number 32, and is generally depicted by x's within the interface or in the locale of the interface.

TABLE 1

Sensing systems and associated biofluid, interface, and biofluid derivative

| Sensing System | Biofluid | Interface | Biofluid Derivative |
|---|---|---|---|
| Transcutaneous electrochemical | interstitial fluid | membrane(s) | post-membrane filtrate |
| Microdialysis | interstitial fluid | dialysis membrane | dialysate |
| Cutaneous Port | interstitial fluid | wound surface | wound fluid |
| Iontophoretic type of cutaneous port | interstitial fluid | iontophoretic site | iontophoretically driven fluid |
| Fully Implanted | interstitial fluid or whole blood | membrane(s) | post-membrane filtrate |

3. Provision of Biocompatibility-Promoting Catalytic Agents Relative to an Interfacing Membrane in a Transcutaneous Electrochemical Analyte Sensor 3a. Utility of Catalytic Agents Active in the Degradation of Biologically-Originating Reactive Oxygen Species and Reactive Nitrogen Species The functioning and performance of a transcutaneous type of analyte sensor may be complicated by the biological response to the intrusion of a foreign body, which generally is associated with the biological generation of reactive oxygen and nitrogen species, and manifests as inflammation. It may be possible to intervene in such a biological response in a variety of ways, such as, for example, by providing a bioactive agent or biological response modifier (BRM), such as a drug, a steroid, a protein hormone, an antibody, a cytokine, or any suitable combination thereof, that has a direct effect on cells of the immune system which may ultimately reduce inflammation at the site of a sensor insertion or implantation. (See, for example, U.S. Pat. No. 6,497,729 B1, filed on Nov. 19, 1999, and U.S. Patent Application Publication No. 2003/0099682A1, filed on Jan. 31, 2002, each of Moussy et al., and U.S. Patent Application Publication No. 2003/0199837A1 of Vachon, filed on Apr. 22, 2002, and U.S. Pat. No. 6,770,729B2 of Van Antwerp, filed on Sep. 30, 2002.) It may also be possible to approach the problem of the presence of oxidants and inflammation by providing stoichiometrically oxidant scavenging agents such as vitamins C and E. It may be further possible to provide a metal that can affect the concentration of a metabolite in the extracellular fluid surrounding such a site and thereby mediate the immune response and its effect. For example, it is theorized that certain metals such as titanium; zirconium, palladium, gold, and platinum, or certain metal oxides, such as titanium dioxide and zirconium oxide, may inhibit the production or net accumulation of reactive oxygen species that are associated with inflammation at an implant site. (See, for example, Published PCT Application, International Publication No. WO 03/063925A1 of Bjursten et al., filed on Jan. 31, 2003.)

Embodiments of the present invention make use of proteinaceous and non-proteinaceous organic-metal catalytic agents in order to ameliorate aspects of a biological response to the intrusion of a foreign body, which can ultimately degrade the performance of an implanted or partially-implanted device such as an analyte sensor. Such catalytic agents include proteinaceous catalysts such as enzymes, and catalytic organic-metal compounds, further described below, which are termed enzyme mimics. By way of example, superoxide-dismutase/catalase catalysts, can metabolically inactivate biologically originating reactive oxygen species, while remaining unchanged by the reaction and thus available for further catalytic activity. The effect of catalytic agents in the body is one that relies not on directly modifying cellular behavior, but rather their effect is mediated by the changes they create in the composition of chemical species in solution.

Yet further catalytic agents that act on local concentrations of one or more metabolite(s), such as reactive nitrogen species, may be usefully employed according to the present invention. Merely by way of example, catalysts that act to decompose peroxynitrite may be so employed. (See, for example, U.S. Pat. No. 6,245,758 of Stern et al., filed on Sep. 9, 1996, and U.S. Pat. No. 6,448,239 of Groves et al., filed on Jun. 1, 2000; U.S. Patent Application Publication No. U.S. 2003/0055032 A1 of Groves et al., filed on Jul. 29, 2002; and Published PCT Applications, International Publication Nos. WO 95/31197 A1 of Stern et al., filed on May 9, 1995, WO 98/43637 A1 of Riley et al., filed on Mar. 26, 1998, and WO 00/75144 A2 of Groves et al., filed on Jun. 2, 2000.) Such catalysts include metalloporphyrin peroxynitrite catalysts, for example. (See Szabo et al., *Part I: Pathogenetic Role of Peroxynitrite in the Development of Diabetes and Diabetic Vascular Complications: Studies with FP15, a Novel Potent Peroxynitrite Decomposition Catalyst*, Mol. Med. 2002, 8(10), 571-580; Mabley et al., *Part II: Beneficial Effects of the Peroxynitrite Decomposition Catalyst FP15 in Murine Models of Arthritis and Colitis*, Mol. Med. 2002, 8(10), 581-590; and Pacher et al., *Potent Metalloporphyrin Peroxynitrite Decomposition Catalyst Protects Against the Development of Doxorubicin-Induced Cardiac Dysfunction*, Circulation, Feb. 18, 2003; 107(6), 896-904.)

Thus, according to an embodiment of the present invention, at least one catalytic agent is provided in proximity to a sensor such that the catalytic agent changes the concentration of at least one biologically-derived reactive oxygen species or reactive nitrogen species in the biofluid environment surrounding and in contact with the sensor. The provision of such a catalytic agent in this manner may be used to influence various families of oxygen and nitrogen metabolite and associated biological pathways, such as oxygen radicals, superoxide, hydrogen peroxide, and any associated oxidant or metabolic pathway; nitric acid, peroxynitrite, and any associated nitric acid or metabolic pathway; nitric oxide, nitric chloride, and any associated metabolic pathway; and any catabolic pathway of intermediary metabolism. The provision of superoxide-dismutase/catalase catalysts is further described herein, in detail and by way of example, in the context of various continuously-sensing sensor systems.

3b. A Transcutaneous Electrochemical Sensor and its Fabrication

Synthesis of inventive membranes suitable for covering the sensing surface of a transcutaneous glucose sensor have been detailed in the related applications (U.S. patent application Ser. No. 10/819,498 of Feldman et al., filed on Apr. 6, 2004, U.S. patent application Ser. No. 10/775,604 of Feldman et al., filed on Feb. 9, 2004, U.S. patent application Ser. No. 10/146,518 of Mao et al., filed on May 14, 2002, the corresponding U.S. Patent Application Publication No. U.S. 2003/0042137 A1 of Mao et al., published on Mar. 6, 2003, and U.S. Provisional Patent Application No. 60/291,215 of Mao, filed on May 15, 2001) all of which have been incorporated by reference. An example of fabricating a sensor with such a membrane that demonstrates the effects on sensor performance of such a membrane, and of such a membrane with a superoxide dismutase/catalase catalyst incorporated therein, is now provided. Sensor fabrication typically consists of depositing an enzyme-containing sensing layer laid over a working electrode, and casting the diffusion-limiting membrane layer over the sensing layer, as well as (optionally and preferably) over the counter and reference electrodes. The procedure below concerns the fabrication of a two-electrode sensor, such as that depicted in FIGS. 2A-2C, described in detail below. Sensors having other configurations such as a three-electrode design can be prepared using similar methods.

A particular example of sensor fabrication, wherein all numerical designations are approximate, is now provided. A sensing layer solution was prepared from a 7.5 mM HEPES solution (0.5 μL, pH 8), containing 1.7 μg of the polymeric osmium mediator compound L, as disclosed in the Published Patent Cooperation Treaty (PCT) Application, International Publication No. WO 01/36660 A2 of Mao et al., filed on Nov. 14, 2000; 2.1 μg of glucose oxidase (Toyobo); and 13 μg of poly(ethylene glycol)diglycidyl ether (molecular weight 400). Compound L is shown below.

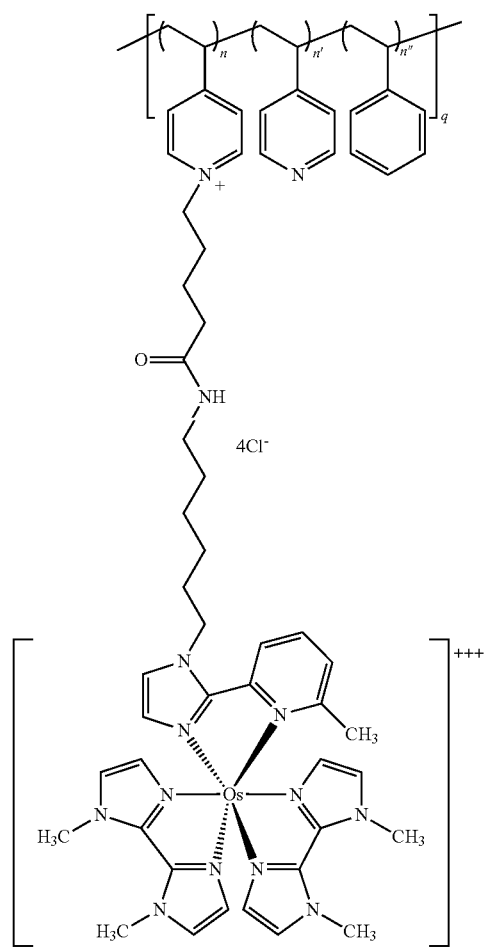

Compound L

The sensing layer solution was deposited over carbon-ink working electrodes and cured at room temperature for two days to produce a number of sensors. A membrane solution was prepared by mixing 4 volumes of a polymer of Formula 1 below, dissolved at 64 mg/mL in 80% EtOH/20% HEPES buffer (10 mM, pH 8), and one volume of poly(ethylene glycol) diglycidyl ether (molecular weight 200), dissolved at 4 mg/mL in 80% EtOH/20% HEPES buffer (10 mM, pH 8). The above-described sensors were dipped three times into the membrane solution: about 5 seconds per dipping, with intervals of about 10 minutes between dips. The sensors were then cured at room temperature and normal humidity for 24 hours.

Formula 1

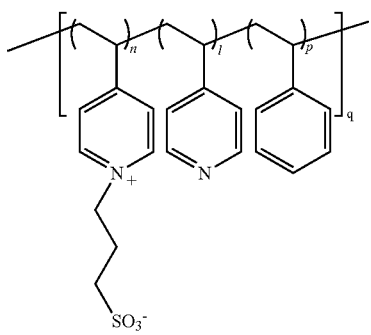

Such a membrane may be employed in a variety of sensors, such as the two- or three-electrode sensors described previously in detail in U.S. Patent Application Publication No. U.S. 2003/0042137A1 of Mao et al., published on Mar. 6, 2003, which is incorporated in its entirety herein by this reference. By way of example, the membrane may be used in a two-electrode amperometric glucose sensor, as shown in FIGS. 2A-2C (collectively FIG. 2). The amperometric glucose sensor 10a of FIG. 2 comprises a substrate 13 disposed between a working electrode 29a that is typically carbon-based, and an Ag/AgCl counter/reference electrode 29b. A sensor or sensing layer 18a is disposed on the working electrode. A membrane or membrane layer 30a encapsulates the entire glucose sensor 10a, including the Ag/AgCl counter/reference electrode. The sensing layer 18a of the glucose sensor 10a consists of crosslinked glucose oxidase and a low potential polymeric osmium complex mediator, as disclosed in the above-mentioned Published PCT Application, International Publication No. WO 01/36660 A2. The enzyme- and mediator-containing formulation that can be used in the sensing layer, and methods for applying them to an electrode system, are known in the art, for example, from the above-mentioned U.S. Pat. No. 6,134,461 of Say et al. According to the present invention, the membrane overcoat was formed by thrice dipping the sensor into a membrane solution comprising 4 mg/mL poly(ethylene glycol)diglycidyl ether (molecular weight of about 200) and 64 mg/mL of a polymer of Formula 1 above, wherein $[n/(n+l+p)] \times 100\% \approx 10\%$; $[1/(n+l+p)] \times 100\% \approx 80\%$; and $[p/(n+l+p)] \times 100\% \approx 10\%$, and curing the thrice-dipped sensor at ambient temperature and normal humidity for at least 24 hours, such as for about one to about two days. The q value for such a membrane overcoat may be greater than or equal to about 950, where n is 1, l is 8, and p is 1.

3c. The Incorporation of Compounds with Superoxide Dismutase and/or Catalase Activity into the Protective Membrane of a Transcutaneous Electrochemical Sensor According to the present invention, polymers utilized in the synthesis of a membrane that may be disposed over the sensing surface of an analyte sensor have a large number of heterocyclic nitrogen groups, such as pyridine groups, only a few percent of which are used in crosslinking during membrane formation. The membrane thus has an excess of these groups present both within the membrane matrix and on the membrane surface. More specifically, incorporation of superoxide-dismutase/catalase catalysts, such as an enzyme or an enzyme mimic, is accomplished by using the biosensor membrane chemistry. In the case of a glucose biosensor membrane, the membrane chemistry relies on crosslinks formed between glycidyl ethers (as supplied by a bifunctional crosslinker such as poly(ethylene glycol)diglycidyl ether (as described above, in connection with the description of polymer of Formula 1) or by a trifunctional crosslinker such as triglycidyl glycerol (as described below, in the context of Example 1), and either amino groups (from enzymes, such as glucose oxidase) or pyridyl groups (from the poly(vinylpyridine)-based membrane polymer)). FIG. 3A depicts a typical structure of a section of an analyte-diffusion-limiting membrane with a catalytic agent incorporated therein with a bi-functional cross-linker. FIG. 3B depicts a membrane structure similar to that in the FIG. 3A, except that it shows a specific a SOD/catalase mimic, MnTPyP, covalently incorporated in the membrane, and in this case, with a tri-functional cross-linker. Since SOD contains amino groups and SOD mimics can be prepared that contain amino or pyridyl groups, the SOD enzyme or mimic thereof can be incorporated throughout the bulk of the membrane material. The bulk loading procedure of the present invention can readily yield membranes with at least about a 10 weight percent loading of an SOD mimic, and possibly higher levels are also achievable. A higher loading efficiency offers the potential for greater anti-inflammatory activity, greater robustness, and/or an increased shelf life. Superoxide-dismutase/catalase catalysts can be incorporated into a glucose-flux-reducing membrane in a variety of ways, some of which can result in the catalyst being irreversibly bound to the membrane, by covalent bonds. Weaker types of chemical association between the polymers and the catalyst include ion-exchange interactions. Finally, functionality of the superoxide-dismutase/catalase catalysts could be supported as well by highly constraining polymer structures that effect a containment or adsorption of the catalyst, and allow it to leach out over the lifetime of the sensor.

The appropriate weight percent level of the SOD catalyst or mimic may be determined by empirical observation of the performance and the effectiveness of membrane-covered sensors in human subjects. For example, as described relation to Example 3 in the following section, sensors covered with membranes having a weight loading of about 5% of a mimic (manganese 5,10,15,20-tetra(4-pyridyl)-21H,23H-porphine chloride (hereafter MnTPyP) showed a lower incidence of, or complete absence of, low-glucose-reading incidents, such that this weight loading of mimic was considered appropriate for these sensors. The effective weight percent loading may vary with the effectiveness of the catalyst. In separate assays, the catalytic effectiveness ($k_{cat}$) of various superoxide dismutase mimics has been shown to vary over several orders of magnitude (see FIG. 1 of Batinic-Haberle, *Manganese Porphyrins and Related Compounds as Mimics of Superoxide Dismutase*, Methods Enzymol. 2002, 349, 223-33). Further, the effective weight percent loading may vary somewhat as a function of the relative weights of the specific mimic(s) and specific polymer(s) that are used as membrane components. Lower limits of weight % loading are contemplated herein, as may be evident from empirical measures of sensor performance and/or the defining of a useful threshold level of performance, such as performance in human subjects, particularly upon the accumulation of a sufficient amount of data. Upper limits of weight % loading are also contemplated herein, and may be founded on constraints in the synthetic process and/or on evidence of negative consequences of an excess amount of mimic on the physical characteristics or the performance of the membrane. These considerations notwithstanding, it is contemplated that the weight percent of a mimic (MnTPyP) relative to the membrane is preferably from about 0.0001 to about 30 weight %, more preferably from about 0.001 to about 20 weight %, and most preferably from about 0.01 to about 10 weight %. Further, it is contemplated that these weight percent ranges are applicable to other catalysts and mimics, particularly when such amounts are expressed in terms of comparable weight relative to a sensor, or comparable weight relative to a sensing surface area, as described below.

As described above, some embodiments of the present invention include a superoxide-dismutase/catalase catalyst that is not covalently incorporated into a polymeric membrane, but is otherwise associated with a polymeric membrane. By way of example, a superoxide-dismutase/catalase catalyst or mimic may be held within the membrane by ionic interactions. In such cases, the catalyst or mimic may be allowed to leach out from the polymer. In other embodiments, the catalyst or mimic can be adsorbed onto the membrane, or held within it by the polymeric matrix. In still other embodiments, the superoxide-dismutase/catalase catalyst or mimic may not be strictly associated with a polymeric membrane covering a sensor surface per se, but rather may be disposed in proximity with respect to a polymeric membrane that is sufficient to have a beneficial effect on membrane or sensor performance. In these various embodiments, it may be more appropriate to express the amount of catalyst or mimic present in terms other than weight % relative to the membrane, such as weight relative to the sensing surface area of the sensor. For example, as described in Examples 1 and 2 of the following section, MnTPyP in an amount of about 5 weight % relative to a membrane has a clear beneficial effect on sensor performance. For a sensor having a sensing surface area of about 7 $mm^2$, this value may be expressed as a total mimic amount of about 20 micrograms/sensor, or about 3 micrograms/$mm^2$ of the sensing surface area. Such a value may be used as an initial benchmark for estimating an effective amount of a superoxide-dismutase/catalase catalyst or mimic when such is disposed within the locale of the sensor, but not necessarily on the flux-limiting membrane per se, as is the case in some embodiments described below.

According to the present invention, a catalytic agent, such as a superoxide-dismutase/catalase mimic, may be associated with a polymeric matrix of a sensor. For example, a catalyst or a mimic may be closely held in association with a flux-limiting membrane of a sensor by way of covalent bonds, as previously described. As metabolites diffuse in the extracellular fluid environment surrounding a sensor, even a closely-held catalyst or mimic that affects the local concentration of metabolites, such as superoxide and hydrogen peroxide, affects not only the environment in immediate contact with the sensor, but also a more extended environment that surrounds the sensor. Thus, according to the present invention, the catalyst or mimic need not be associated or closely associated with a flux-limiting membrane, per se, but need only be sufficiently local relative to the sensor to affect the concentration of one or more metabolite(s), such as superoxide and/or hydrogen peroxide, in the environment surrounding the sensor. Thus, in some embodiments of the invention, a catalytic agent is not associated with a flux-limiting membrane, per se, but is instead associated with any membrane, surface or reservoir that is present in a location sufficiently near the sensing surface, such that composition of the fluid surrounding the membrane is altered by the presence of the catalytic agent in terms of metabolites and their respective concentrations. For example, according to an embodiment of the invention, a catalyst or mimic may be disposed on an inner surface of a protective covering of a transcutaneous sensor.

Superoxide-dismutase/catalase catalysts may be incorporated into the existing membrane formulation in various ways. For example, a preparation of one or more enzyme(s), such as superoxide dismutase and/or catalase, may be incorporated into a membrane covering a sensing surface, or into a matrix or matrices, or a reservoir or reservoirs, in a vicinity or locale of the sensing surface. Such enzymes can be derived from various natural sources (including plant, animal, bacteria, or yeast), or through genetic engineering and production of improved versions of the proteins by known methods. These enzymes may contain suitable metal elements or transition metal elements, such as manganese, iron, copper, zinc, or any combination thereof, merely by way of example. For example, superoxide dismutase may comprise a metal such as manganese, iron, copper, or zinc; catalase may comprise iron, and thus, be referred to as a "heme" enzyme; and a superoxide-dismutase/catalase catalyst may comprise any suitable metal.

According to embodiments of the invention, one or more compound(s) from a broad class of non-proteinaceous compounds that mimic the catalytic action of superoxide dismutase and/or catalase may be used in place of, or in addition to, superoxide dismutase and/or catalase. Examples of such compounds, include, but are not limited to the following: (1) manganese 5,10,15,20-tetra(4-pyridyl)-21H,23H-porphine chloride (MnTPyP); (2) MnTPyP quaternized at one to three of the pyridyl sites; (3) MnTPyP quaternized at all four pyridyl sites; (4) MnTPyP quaternized at at least one pyridyl site by a quaternizing moiety and having a free pyridyl or an amino functional group attached to at least one quaternizing moiety; (5) a compound comprising manganese coordinated in a macrocyclic, penta-amine ring, and also comprising a reactive amino or pyridyl moiety, such as M40403 or M40470, from Metaphore Pharmaceuticals, Inc. (St. Louis, Mo.); (6) a compound, other than that of item (5) above, having SOD activity, such as any such compound described by Metaphore Pharmaceuticals, Inc. or in the above-mentioned Published PCT Application, International Publication No. WO 00/72983 A2, or in U.S. Pat. No. 5,696,109 to Malfroy-Camine et al., filed on Jun. 7, 1995, such as a transition metal chelate of pentaaza-cyclopentadecane compound or a salen compound (for example, a manganese or an iron chelate of any such compound), derivatized with a reactive amino or pyridyl group; (7) a bipyridine manganese complex or a cyclic salen-transition-metal complex, such as any disclosed by Eukarion, Inc. (Bedford, Mass.) or in above-referenced U.S. Pat. Nos. 6,403,788, 6,541,490, 6,573,257 and 6,589,948; (8) any suitable manganese porphyrin, iron porphyrin, manganese polyamine, iron polyamine, manganese salen, and iron salen complex, such as those described by Batinic-Haberle (*Manganese Porphyrins and Related Compounds as Mimics of Superoxide Dismutase*, Methods Enzymol. 2002, 349, 223-33), and in published patents or patent applications (U.S. Pat. No. 5,227,405 of Fridovich et al., filed on Sep. 28, 1988, U.S. Pat. No. 5,994,339 of Crapo et al., filed on Jun. 7, 1995,U.S. Pat. No. 6,103,714 of Fridovich et al., filed on Jul. 24, 1996, U.S. Pat. No. 6,127,356 of Crapo et al., filed on Jun. 7, 1996, U.S. Pat. No. 6,479,477 of Crapo et al., filed on Apr. 23, 1999, and U.S. Pat. No. 6,544,975 of Crapo et al., filed on Jan. 25, 2000, and U.S. Patent Application Publication Nos. 2002/0082490 A1 of Roeper et al., filed on Jul. 20, 2001, and 2003/0069281 A1 of Fridovich et al., filed on Jun. 14, 2001); (9) any of the biporphyrin superoxide-dismutase/catalase mimics of Bruice (above-mentioned U.S. Pat. Nos. 5,202,317 and 5,217,966); and (10) the compound manganese (III) tetrakis(4-benzoic acid) porphyrin (MnTBAP), marketed by Alexis Biochemicals (Paris, France), whose use as a superoxide dismutase mimic is described by Weill et al., in the above-mentioned U.S. Patent Application Publication No. U.S. 2003/0118577 A1.

FIGS. 4A and 4B, together, illustrate a fully fabricated sensor, with a catalytic agent incorporated into a protective membrane, as the sensor would be seen placed on the skin, with a portion of the sensor transcutaneously inserted into the subcutaneous space. FIG. 4A provides a perspective view of a sensor 10a, the major portion of which is above the surface of the skin 50, with an insertion tip 11 penetrating through the skin and into the subcutaneous space 52, where it is bathed in biofluid 40. Contact portions of a working electrode 29aa, a reference electrode 29bb, and a counter electrode 29cc can be seen on the portion of the sensor 10a situated above the skin surface. Working electrode 29a, a reference electrode 29b, and a counter electrode 29c can be seen at the end of the insertion tip 11. FIG. 4B provides an expanded and cutaway view of sensor insertion tip 11. The working electrode 29a is shown resting on top of a plastic substrate 13, a wired enzyme sensing layer 18a rests on top of a portion of the working electrode 29a. Overlaying the sensing layer and a portion of the electrode, depicted transparently, is an interfacing membrane 30a, and associated with and dispersed throughout the membrane is a catalytic agent 32, the membrane covering the sensing layer 18a of the enzyme-based electrochemical sensor. The tip 11 is in the subcutaneous space 52 (as seen in FIG. 4A) and is consequently bathed in the surrounding biofluid 40. The catalytic agent is dispersed in the membrane by admixing into the membrane solution used in the synthesis of the membrane, a bulk loading procedure, as described in U.S. patent application Ser. No. 10/819,498 of Feldman et al., filed on Apr. 6, 2004, which is a continuation-in-part of U.S. patent application Ser. No. 10/775,604 of Feldman et al., filed on Feb. 9, 2004. This procedure is a modification of a membrane synthesis procedure described earlier in the U.S. Patent Application Publication No. U.S. 2003/0042137A1 of Mao et al., published on Mar. 6, 2003.

4. Examples of the Performance of Transcutaneously-Placed Electrochemical Sensors with a Membrane that Includes a Biocompatibility-Promoting Catalytic Agent Example 1

Performance of Sensors with Catalyst-Enhanced Membranes in In Vitro Tests

A catalytic membrane solution that included a buffer solution and a membrane polymer preparation was prepared. The buffer solution comprised 4 parts of ethanol to 1 part of 10 mM HEPES, for a final concentration of 2 mM HEPES. The membrane polymer preparation comprised 116 mg/ml of a formulation called 10Q5, as depicted below (wherein x=0.85, y=0.1, z=0.05, n=9, m=1, and p=about 10), 8 mg/ml triglycidyl glycerol (the crosslinker), and 7.5 mg/ml manganese 5,10,15,20-tetra(4-pyridyl)-21H,23H-porphine chloride (MnTPyP), a compound possessing both superoxide dismutase and catalase activity.

Formulation 10Q5

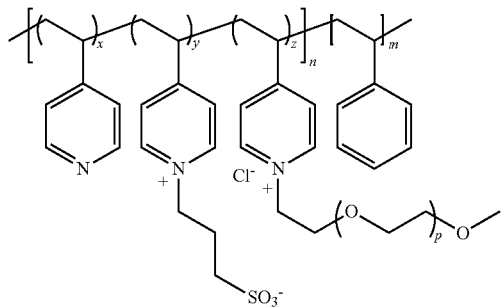

A batch of sensors was prepared by dipping membrane-less sensors (which contained previously deposited, wired-enzyme sensing layers) three times, in succession, into the catalytic membrane solution. Each resulting sensor membrane contained approximately 13 micrograms of the catalyst, MnTPyP, or a load with respect to the membrane of about 5.7 weight %. Incorporation of the catalyst was broadly verified by the visual observation of an intense dark color imparted to the membrane.

FIG. 5 depicts the in vitro performance of a group of individually fabricated sensors in terms of the current output in nanoAmps (nA) as a function of the glucose concentration (from 0 to 30 mM) to which the sensors were exposed in a bench-top experiment. Two features of the graphed results are of interest. First, the slopes of the performance of each of these separately prepared sensors are very close to each other, indicating substantial consistency in the fabrication process. Second, the graph is substantially identical to the results observed for a control sensors, i.e., those fabricated with conventional membranes, containing no MnTPyP (data are shown in U.S. patent application Ser. No. 10/819,498 of Feldman et al., filed on Apr. 6, 2004, which is a continuation-in-part of U.S. patent application Ser. No. 10/775,604 of Feldman et al., filed on Feb. 9, 2004.) For example a concentration of 30 mM glucose elicits a current output of approximately 30 nA in sensors regardless of the presence or absence of the catalytic agent MnTPyP. These data, collectively, taken from tests run with separate preparations, and at different times, offer strong support for the robustness of the method of preparing membrane-covered sensors, for the consistency of performance, and for the absence of any negative effects of an incorporated superoxide-dismutase/catalase mimic on the linearity of sensor performance in this bench-top context.

Example 2

Comparison of Performance of Sensors with a Conventional Membrane and Sensors with a Catalyst-Enhanced Membrane in Human Subjects The performance of sensors with catalyst-enhanced membranes was tested in 22 volunteer, non-diabetic human subjects, and compared to the simultaneous performance of sensors with conventional membranes that have no catalyst enhancement. The human-subject study was approved by the Institutional Review Board of TheraSense, Inc. (now Abbott Diabetes Care, Alameda, Calif.). Subjects were informed of risks and consented to participate in view of possible risks, such as bruising, edema, erythema, and excessive bleeding. Subjects were free to discontinue the study at any time, and were limited to three sensor-attachment attempts over the course of the three-day study. Following the study and sensor removal, subjects were examined for any manifestation of the identified risks.

In this experiment, each volunteer subject was fitted simultaneously with two transcutaneous glucose sensors, a control sensor and an experimental sensor. The control sensor and the experimental sensor were prototypes of a Freestyle® Navigator™ continuous glucose-monitoring system manufactured by Abbot Diabetes Care. Each of the sensors had a protective membrane as described previously, but the membrane of the control sensor was not catalytically enhanced, while the experimental sensor was enhanced with a MnTPyP catalyst in an amount of about 5% by weight with respect to the weight of the polymer membrane. Each of the sensors transmitted its data by radio frequency transmission to an external hand-held display unit that stored and processed the data.

For each human subject, glucose values were automatically and continuously collected from the control sensor and the experimental sensor over a three-day period to obtain a stream of control sensor data and a stream of experimental sensor data, respectively. Additionally, each human subject manually collected glucose values from his or her capillary blood using a Freestyle® glucose strip-reading meter manufactured by Abbott Diabetes Care at irregular intervals, but at a rate of about 10 to about 15 samples per day. The human-subject data and associated statistical data, shown in Table 2 below, were then compared to evaluate the effect of the super-oxide-dismutase/catalase catalyst associated with the experimental sensor.

TABLE 2

Comparison of Performance for Control and Experimental (Inventive) Sensors

| Sensor Type | (not enhanced) | Experimental (enhanced with catalytic agent) | Comment |
| --- | --- | --- | --- |
| Number of Subjects | 22 | 22 | Identical, by design |
| Number of Data Points | 1046 | 1037 | Comparable, by design |
| Clarke Statistics | | | |
| % A (accurate zone) | 71.6% | 82.8% | 16% improvement |
| % B (indifferent zone) | 27.9% | 16.8% | 66% improvement |
| % D (inaccurate zone) | 0.5% | 0.4% | 25% improvement |
| Average Error | 14.7% | 11.4% | 29% improvement |
| Noise Parameter | 0.050 | 0.037 | 26% improvement |
| Total % of time reporting glucose <40 mg/dL | 1.78% | 0.43% | 76% improvement |

In a first comparison, the accuracy of data from the control sensors (control sensor data) and data from the experimental sensors (experimental sensor data), relative to the reference data from coincidentally obtained, manual capillary blood measurements, were compared. This involved analyzing the control sensor data and the experimental sensor data using Clarke statistics (Clarke et al., *Evaluating Clinical Accuracy of Systems for Self-Monitoring of Blood Glucose*, Diabetes Care, vol. 10, issue 5, 622-628, 1987) to characterize the error relative to the reference data and to determine an average error for each of the two data streams.

In the characterization and determination of error associated with the experimental sensors, the percentage of the data associated with the accurate zone was about 82.8%; the percentage of the data associated with the inaccurate zone (D) was about 0.4% and with the indifferent zone (B) was about 16.8%; and the overall error was about 11.4%. These values compare favorably with those associated with the control sensor (Table 2). More particularly, the accuracy of experimental sensors was about 16% higher than that of the control sensors; the inaccuracy of the experimental sensors was about 25% less than that of the control sensors; and the overall average error of the experimental sensors was about 29% less than that of the control sensors. These data demonstrate that the experimental sensors are capable of providing data of greater accuracy than the data provided by the control sensors.

In a second comparison, data from the control sensors and the experimental sensors with respect to noise within the data stream were compared. This involved calculating a "noise parameter" for the control sensors and a noise parameter for the experimental sensors to compare the level of noise associated with each of the two data streams. Each noise parameter was calculated by determining the percentage difference between (a) the average rate of change in glucose concentration (in mg/dL per minute) for a complete stream of continuous data from each sensor and (b) the average rate of change of glucose concentration (in mg/dL per minute) for the same data stream, after it has been smoothed by the application of a 10-minute boxcar filter. As data-smoothing inherently reduces the mean rate of change, the value associated with the latter, smoothed average rate (b, above) is at least some degree less than the value for the former, raw average rate (a, above). If the raw data are relatively smooth to begin with, these two average rates will be very similar, such that the noise parameter will be relatively small. If the raw data are noisy, the two average rates will differ more greatly, such that the noise parameter will be relatively large. Thus, the noise parameter is relatively small for smooth data and relatively large for noisy data.

In this noise comparison, the noise parameter associated with the experimental sensors was about 0.037, while that associated with the control sensors was about 0.050, as shown in Table 2. The experimental sensors thus outperformed the control sensors by reducing noise by about 26%. These data demonstrate that experimental sensors are capable of providing glucose readings with much less noise than are control sensors. The foregoing comparisons demonstrate that a superoxide-dismutase/catalase catalyst can be used according to the present invention to enhance or improve sensor performance.

In the course of this experiment, the experimental sensors and the control sensors were also evaluated as to the total fraction of data-reporting time in which values of less than 40 mg/dL were reported (bottom line, Table 2), and of the occurrence or non-occurrence of low-glucose-reading incidents. The significance of glucose values of less than 40 mg/dL is that experienced health care professionals tend to regard them as spurious in apparently normal controls. Thus, the 76% decrease in the reporting of these values by sensors in the "experimental" group is regarded as an improvement in performance. In this evaluation it was further determined that no low-glucose-reading incidents occurred when catalyst-enhanced, experimental sensors were used. By contrast, it was determined that several low-glucose-reading incidents occurred when non-enhanced, control sensors were used. One such incident is described below in relation to FIG. 6, after the following general discussion of such incidents.

When a transcutaneous sensor is used by either a diabetic or a non-diabetic subject, it may provide, on occasion, a glucose reading that a health care professional or an experienced observer would judge to be spurious, i.e., as not being reflective of the subject's systemic glucose level. These low-glucose-reading incidents generally occur in the first 24 hours following transcutaneous placement of the sensor, especially when the subject is sleeping. A non-diabetic human subject is an appropriate model for the study of these incidents, as even though diabetic and non-diabetic human subjects have different glucose values in absolute terms, both groups exhibit low-glucose-reading incidents that are broadly similar. A low-glucose-reading incident may be recognized in a healthy, non-diabetic human subject when a glucose reading is below about 60 mg/dL for a period of time longer than but a few minutes, as such a person rarely has a blood glucose value that is actually that low. Such an incident may also be inferred as spurious when the subject's physical movement causes the glucose reading to quickly return to a normal level. A low-glucose-reading incident might also be more directly shown to be spurious by comparing the glucose reading from the transcutaneous sensor with a glucose reading obtained simultaneously from a conventional blood sample, and noting a significant discrepancy. This latter comparison method, however, is generally impractical in an experiment of the design described herein, as these low-glucose-reading incidents generally occur when a person is sleeping and thus not able to obtain a conventional blood sample (i.e., a capillary blood sample obtained via a blood-lancing device), manipulate the sample (i.e., apply it to a conventional test-strip), and obtain a reading from a glucose meter (i.e., a conventional glucose meter that is used in connection with a conventional test-strip).

By any of the approaches or scenarios described above, experienced or informed observers may recognize low-glucose-reading incidents as being spurious. Nevertheless, these incidents remain highly problematic, as falsely indicating hypoglycemia. Further, if such an incident occurs soon after the sensor is inserted, calibration of the sensor may be compromised such that the problem is amplified. The problem of low-glucose-reading incidents has been observed to result from variability inherent in human subjects rather than from variable quality in transcutaneous sensors. That is, data from a known group of human subjects suggests that these incidents occur more often with some subjects than with others. Thus, it appears that these incidents might be better understood in terms of the variability of the biology and biochemistry of the subcutaneous space in human subjects, as well as other subjects. In this regard, it is contemplated that the presence of cells, such as neutrophils, from the immune system, and/or the metabolic activity of those cells, such as the consumption of glucose and the generation of highly reactive oxidative species, such as superoxide ion and hydrogen peroxide, may play a role in these incidents.

In this evaluation of low-glucose-reading incidents, experimental data obtained from one non-diabetic human subject in the manner described above was charted over a three-day period, as shown in FIG. 6. These data included the continuous readings of glucose concentration (mg/dL) from the control sensor, as represented by the darkly shaded "curve;" the continuous readings of glucose concentration (mg/dL) from the experimental sensor, as represented by the lightly shaded "curve;" and the intermittent glucose readings that were manually obtained from capillary blood, as represented by shaded triangles. It should be noted that, for reasons mentioned above, capillary blood reference data were not obtained during typical periods of sleep. As low-glucose-reading incidents typically occur during sleep, the capillary reference data, while shown for certain times, were not relevant to this evaluation.

A portion of the curve associated with the control sensor (i.e., the sensor having a membrane, but no catalyst enhancement) is circled in FIG. 6 to highlight a particular low-glucose-reading incident. This incident appears to be typical of those associated with conventional sensors in that it occurred within the first 24 hours of the transcutaneous use of the control sensor; it occurred from late in the night to early in the morning, a typical sleep period; and it was associated with apparent glucose concentrations that are below 60 mg/dL and fell as low as about 22 mg/dL. If true, a glucose concentration as low as 22 mg/dL would indicate a threateningly dangerous level of hypoglycemia. In contrast, a corresponding portion of the curve associated with the experimental sensor (i.e., the sensor having a membrane, as well as MnTPyP enhancement) that lies directly above the circle in FIG. 6, shows no such low-glucose-reading incident. That is, this portion of the curve corresponds to normal glucose readings from about 65 mg/dL to about 85 mg/dL that were obtained from the same person during the same period. The data from this experiment support the conclusion that during the period associated with the low-glucose-reading incident, the control sensor data were false and the experimental sensor data were accurate with respect to systemic blood glucose levels.

The foregoing results demonstrate that under conditions in which a conventional sensor produces a low-glucose-reading incident, a catalyst-enhanced experimental sensor according to the present invention produces no such incident. These results suggest that the catalyst acts to reduce, mitigate, or prevent low-glucose-reading incidents. The results of the experiment described above also demonstrate that relative to a non-enhanced sensor, a catalyst-enhanced sensor according to the present invention provides data of higher accuracy and less noise. It is believed, without being so bound, that the catalyst reduces the local concentration of metabolites, such as superoxide and hydrogen peroxide, in the area surrounding the sensor, and thereby enhances the performance of the transcutaneous sensor. Inasmuch as these improvements in performance are rectifying problems associated with the in vivo environment and various biological reactions to the presence of the sensor, it may be concluded that the enhancement of the sensor with a catalyst, as described herein, significantly improves the biocompatibility of such an enhanced sensor. It may further be concluded that the improved biocompatibility of the sensor is coincident with or associated with the delivery of higher quality signal, and consequently higher quality data from the sensor, as exemplified by the decreased level of noise, described earlier, the improvement in the Clarke statistics, and the diminished or eliminated number of spurious low-glucose incidents. From these observations, a catalytic agent provided in connection with an analyte sensor may be described variously as having the activity of an agent of biocompatibility or an agent of signal quality, preferably both. Further, as the effect of the catalytic agent is to mitigate the effect that neutrophils have in increasing local concentrations of such reactive species as superoxide and hydrogen peroxide, as well as to mitigate or diminish the rate of recruitment of neutrophils to the sensor site, such a catalytic agent may be described as an anti-neutrophilic agent.

According to the invention, a membrane may be applied to a sensor or a portion of a sensor in any useful way. That is, a membrane need not be applied directly on the sensing surface and need not fully cover the sensing surface, but may be applied less immediately and less completely relative to the sensor. Any such membrane may host one or more catalytic agents, such a superoxide-dismutase/catalase catalyst, either in the form of an enzyme or a non-proteinaceous mimic, or any combination thereof. Further, a surface other than a membrane surface, or a reservoir, such as any of plastic or metallic composition, may host an enzyme or a mimic or any combination of such catalytic agents. The present discussion makes use of electrochemical sensors, with a membrane overlaying the sensing layer by way of example. In other embodiments described in this application, the membrane can be understood as an example of an interface that may include other forms, and the sensing layer can be understood as one example of a transducer, of which there may be other types. Returning to the electrochemical sensor with a sensing layer as an example, a transcutaneous sensor may have a protective medium that covers its sensing surface, but at some distance therefrom rather than immediately thereon. A surface of such a medium may host a superoxide-dismutase/catalase catalyst or mimic or any combination of such catalytic agents. Thus, various embodiments of the invention include those in which a superoxide-dismutase/catalase catalyst or mimic or any combination of same is incorporated into a membrane, such as an analyte-flux-limiting membrane, immediately overlaying the surface of a sensor, as well as those in which such a catalyst or a mimic or any combination of same is in the general locale of the surface of a sensor, though at a distance therefrom and in an amount that is sufficient to enhance the performance of the sensor. A catalyst or mimic or a combination of same, however incorporated or hosted, may act to reduce a local concentration of one or more metabolite(s), such as superoxide and hydrogen peroxide. Any such reduced local concentration of metabolite may act to slow the influx of cells from the immune system that might otherwise be recruited by any such metabolite.

5. Biocompatibility-Promoting Catalytic Agents Incorporated into Sensors that Analyze a Microdialysate of Interstitial Fluid 5a. A Microdialysis Probe and Microdialysis Membranes as an Interface According to an embodiment of the invention, a superoxide-dismutase/catalase catalyst or mimic may be incorporated into a microdialysis membrane and thence into an analyte sensing system, such as a glucose sensing system, that employs such a microdialysis membrane. This type of sensing system is of a partially-implantable type, inserted transcutaneously. The implantation is partial in that a portion of the system (a microdialysis probe) is inserted through the skin, penetrating in to the subcutaneous space, while another portion, including the transducer, remains above the surface of the skin. Examples of microdialysis-based analyte sensing systems, such as those suitable for glucose sensing, include those developed by companies such as Roche (Basel, Switzerland), Disetronic Medical Systems (Bergdorf, Switzerland) and Menarini Diagnostics (Florence, Italy). Such systems are also described in various patents and patent applications, including U.S. Pat. No. 5,640,954 of Pfeiffer et al., filed on May 5, 1995, U.S. Pat. No. 6,091,976 of Pfeiffer et al., filed on Oct. 28, 1998, and U.S. Pat. No. 6,591,126 of Reoper et al., filed on Jul. 20, 2001; U.S. Patent Application Publication No. 2001/0041830 A1 of Varalli et al., filed on May 7, 2001; and European Patent Application No. EP 1153571 A1 of Varalli et al., filed on May 3, 2001. In brief, such a microdialysis-based glucose-sensing system and its functioning can be described as follows: an analyte sensor is located on the surface of the skin of a subject being monitored, and the analyte sample to be sensed comprises a volume of buffer that has been pumped into and out of a subcutaneous space via a tube that is made of a semi-permeable, microdialysis membrane. During its transit through the subcutaneous space, the buffered fluid within the microdialysis tube and the interstitial fluid outside the tube equilibrate in terms of glucose concentration, such that the buffer fluid or dialysate exiting the body is representative of the body's interstitial fluid glucose concentration. A useful reading of glucose concentration is then obtained from the exiting buffer fluid via the external sensor.

In the embodiments of the presently described invention in which a microdialysis process is included with the sensing system, as well as in other embodiments described below, in which a biofluid derivative is obtained from a transcutaneous pore, exemplary sensor systems described in other patents are referenced merely by way of illustration of extant systems. According to the present invention, a catalytic agent is disposed or applied in the locale of an interface between a native analyte-containing biofluid and an analyte-containing derivative of the biofluid that contacts the transducing apparatus of the sensor. In a microdialysis system, such as that described in further detail below, this interface is the dialysis membrane itself. The benefit offered by such a catalytic agent to these sensing systems is generally one of improved biocompatibility and/or improved sensor performance. Schemes that detail the synthesis of dialysis membranes that incorporate a catalytic agent on to their surface are described in the sections that immediately follow this one.

An exemplary microdialysis probe shown in FIG. 7, where it is inserted through the surface of the skin 50, and extends into the subcutaneous space 52, where it is surrounded by interstitial biofluid 40. As will be discussed further below, in this embodiment of the invention, the dialysis tubes embody an interface between the interstitial fluid and the derivative dialysate, and accordingly they are labeled with a variant of part number 30. The probe includes a supply dialysis membrane tube 30s, for supplying a fresh dialyzing fluid, and a discharge dialysis membrane tube 30d for removing post-dialysis fluid, each tube comprising a dialysis membrane, the microdialysis membrane as a whole functioning as an interface between the biofluid and a derivative of the biofluid, the dialysate. The dialysis membrane inventively has a catalytic agent 32 incorporated onto its surface, which promotes the biocompatibility of the membrane. In this microdialysis probe, fresh dialysis fluid flows in the membrane tubes 30s and 30d in the direction indicated respectively by the arrows shown within the tubes. The fluid flow is diverted at its lower end directly from tube 30s into tube 30d, the tubes being contiguous or connected to each other. While flowing through these tubes, the dialysis fluid picks up dissolved constituents, such as glucose or other analytes, from the surrounding interstitial biofluid 40, as shown by the directional arrows.

The head portion of microdialysis probe, indicated as a whole by the reference numeral 16 lies outside the body; at its base is a support plate 15, which provides conduits for two tubes 30a and 30b that pass through into the interior of the body. Plate 15 rests on the cutaneous surface of the body 50, generally held thereon by an adhesive. The inlet 27 for the dialysis probe, which is formed as a hose or a pipe and feeds into the supply tube 25, and the outlet 28, which can likewise be a hose or a tube and into which the discharge tube 26 feeds from the interior of the body, are situated above the supporting plate 15. Dialysis thus takes place in such a way that fresh dialysis fluid is introduced into the supply tube 30s in the interior of the body via the inlet 27, as indicated by directional arrows. While flowing through the tubes 30s and 30d, which comprise a dialysis membrane, the dialysis fluid draws in solute(s) such as an analyte from the surrounding tissue, and the thus-modified fluid then leaves the dialysis probe through the outlet 28. Osmotic equilibration of solute concentrations between the fluids internal and external to the dialysis tube as a whole (30s and 30d) occurs across all exposed portions of the tube. Dialysate from the outlet is then brought into contact with the transducing apparatus 18 of an analyte sensor (not shown). The transducing apparatus 18 may be either of an electrochemical type or a viscosimetric type, as described further below.

It can be understood by reference to the FIG. 1 that the dialysis membrane is an interface between a biofluid and a derivative of that fluid, the dialysate. The biofluid specifically referenced here is the interstitial fluid, which occupies the subcutaneous space. The dialysate, once it concludes its circuit through the dialysis membrane tubes can be understood as a derivative of the biofluid that actually contacts the transducing mechanism of the sensor. The biocompatibility-promoting catalytic agent 32 that is associated with the dialysis membrane is in a location such that it is in contact with the biofluid, and can thereby catalytically engage appropriate reactants in the biofluid. More specifically, a catalytic agent that catalyzes the degradation of reactive oxygen species (ROS) or reactive nitrogen species (RNS) may decrease the concentration of such species in the local biofluid surrounding the dialysis membrane.

Once an analyte-containing microdialysate sample has exited from its course through the subcutaneous space, it is available for engagement by any of various types of transduction mechanisms within an external sensor attached to the skin. Viscosimetry is one method, where the interaction of an analyte with another compound creates a measurable increase in the viscosity of the solution that reflects the analyte concentration. This transduction method, known more specifically as affinity viscosimetry relies on sensitive liquids with analyte-dependent viscosity which are localized within a perfusable dialysis chamber and contain colloidal constituents that are cross-linked by affinity bonds. A viscosimetric affinity sensor includes a spatial or temporal separation of analyte diffusion within the body from the measurement of the flow resistance for such sensitive liquid flowing through a narrow tube outside the body. A feature of this approach is the small volume-displacement and thus minimal structural change within the subcutaneous site where the dialysis is taking place. Affinity viscosimetry is described in detail in U.S. Pat. No. 6,267,002 of Ehwald, filed Oct. 12, 1999, and U.S. Pat. No. 6,477,891 of Ehwald, filed Jul. 2, 2001). Another method is that of enzyme-based electrochemical transduction, as described in U.S. Pat. No. 6,434,409 of Pfeiffer and Hoss, filed Jun. 6, 2000.

Various modifications of the arrangement and configuration of the above-described embodiment of a microdialysis-based sensor system will be readily apparent to those of ordinary skill in the art to which the present invention is directed, upon review of the specification. The above-described embodiment, as depicted in FIG. 7, is a simply an example of a system that relies on movement of a dialyzing fluid through a subcutaneous space, the bulk fluid being contained within a tube that comprises a partially permeable dialysis membrane that allows ingress of solute(s), including analyte(s), from the interstitial fluid. The rate of movement of the dialysis fluid and the amount of exposure to the dialysis membrane surface is such that by the time the bulk dialysate emerges from its transit through the tube, the concentration of the analyte is in equilibrium with the concentration of the analyte in the interstitial fluid. The analyte-containing dialysate drawn from the internal subcutaneous dialyzing space is then contacted to an analyte sensor placed on the skin, and the sensor reading is thus reflective of the in vivo analyte concentration.

Dialysis membranes are used in various types of medical and research devices. An example is that of clinical hemodialysis units that allow osmotic exchange of solutes between blood and standard physiological solutions for the purpose of clearing blood of waste products. Another example is that of microdialysis probes, as described above, that allow osmotic exchange of solutes between interstitial fluid and balanced salt solutions for the purpose of extracting physiological solutes for analysis, such as for research and clinical purposes. In both of these examples of the application of dialysis membranes, the membrane acts as an interface between a fluid within a biological space and a fluid within a post-biological space. This membranous interface is a place where either biocompatibility or biological incompatibility is manifested.

Based on hemodialysis experience primarily, the materials used to make dialysis membranes are understood to have varying properties that relate to dialysis performance and to biocompatibility, however broadly defined. Cellulose-based materials, such as cellulose acetate, cellulose diacetate, and a Cuprophane® cellulose material, a so-called "regenerated" cellulose, were the first materials used for dialysis membranes and are still widely used. More recently, synthetic materials, such as polysulfone, polymethylmethacrylate, polyamide, polyacrylonitrile, ethylenevinylalcohol, and various derivatives thereof, have been used for dialysis membranes. These synthetic membranes have been commonly called "biocompatible," thus encouraging the perception of the cellulose-based membranes as being biologically "incompatible" or in some way less biologically compatible than the synthetic membranes. This characterization of cellulose-based materials as being more or less "biologically incompatible" and of synthetic materials as being "biocompatible" may well be a marketing language-based oversimplification, as the evaluation of biocompatibility is rather more involved.

By way of example, a determination of biocompatibility typically rests on the evaluation of a variety of parameters, such as complement activation, expression of surface and adhesion molecules, leukocyte adhesion to dialysis membranes, neutrophil degranulation, etc. (See Unattributed editor, *Biochemical Reactions Subsequent to Complement and Leukocyte Activation*, Nephrol Dial. Transplant 2002, vol. 17 [Supp. 7]: 32-34; Gasparovic et al., *Do Biocompatible Membranes Make a Difference in the Treatment of Acute Renal Failure?*, Dialysis & Transplantation (1998), vol. 27, no. 10: 621-627; Hoffmann et al., *Induction of Cytokines and Adhesion Molecules in Stable Hemodialysis Patients: Is There an Effect of Membrane Material?*, Am J. Nephrol. (2003, vol. 23 (6): 442-447); Gorbet and Sefton, *Biomaterial-Associated Thrombosis: Roles of Coagulation Factors, Complement, Platelets and Leukocytes*, Biomaterials (2004) vol. 25 (26): 5681-5703; and Gorbet et al., *Flow Cytometric Study of In Vitro Neutrophil Activation by Biomaterials*, J. Biomed. Mater Res, vol 44: 289-297.)

While such parameters, listed above, may reflect on biological compatibility, the caution included in the general description of the term "biocompatibility" (see "Various Conventions and Terms" section above) is apt in that the term is highly dependent on specifics of circumstance. Further, although the labeling of commercial materials in this area is broadly accurate, there are also examples of inaccuracy and confusion. For example, in practice, membrane materials can be subject to considerable batch-to-batch variation in terms of their apparent properties (Heineman, *Continuous Glucose Monitoring by Means of the Microdialysis Technique: Underlying Fundamental Aspects*, Diabetes Technology & Therapeutics, 2003, vol 5: 545-561). Further by way of example, membrane materials may be confusingly described, labeled, or named, such as in a case detailed by Gores et al. (*Verification of the Chemical Composition and Specifications of Haemodialysis Membranes by NMR and GPC-FTIR-Coupled Spectroscopy*, Biomaterials 23 (2002) 3131-3140), in which a commercial Polyamide S™ product of Gambro Medizintechnik (Hechingen, Germany) contains no polyamide at all and comprises solely polyarylethersulfone, also known as polyethersulfone. Finally, it is should be noted that, according to the manufacturer, the CMA/Microdialysis Co. (Solna, Sweden), the "CMA 60" dialysis membranes of the microdialysis probes that are used in clinical and research markets are composed of polyamide. Roche Diagnostics GMBH (Mannheim, Germany) reports that this CMA 60 material is the material that is used in its microdialysis probes that are currently in clinical testing (U.S. Pat. No. 6,591,126 of Reoper, filed Jul. 20, 2001; and Shoemaker et al., *The SCGM1 System: Subcutaneous Continuous Glucose Monitoring Based on Microdialysis Technique*, Diabetes Technology & Therapeutics 2003, vol. 5 no. 4: 599-608).

It is contemplated herein that the enhancement of a microdialysis membrane with a catalytic agent may improve the biocompatibility or performance of the membrane within a subcutaneous space in much the same way that catalytic enhancement of a polymeric membrane covering the sensing surface of a transcutaneous sensor (described above) enhances the biocompatibility and performance of such a membrane. It is contemplated, more specifically, that a microdialysis membrane enhanced with a catalytic agent may demonstrate more accurate and less noisy data relative to a non-enhanced microdialysis membrane. A catalytic agent, such as superoxide-dismutase/catalase catalyst, may be used, in any suitable manner, such as any previously described herein, in pursuit of any such enhancement, improvement, or benefit. Further, as previously described with regard to a sensor-covering membrane, a superoxide-dismutase/catalase catalytic agent may be associated with a microdialysis membrane in various ways, such as via covalent bonds, ionic interactions, and/or adsorption. In some embodiments, the catalytic agent may diffuse away from the polymer; in some embodiments, the catalytic agent may remain closely bound to the polymer; and in some embodiments, some portion of the catalytic agent may remain bound to the polymer while another portion may diffuse away from the polymer. In any case, regardless of the degree of binding and/or diffusion, the anticipated effect of the association of the catalytic agent with the membrane is a reduction in the concentration of one or more reactive metabolite(s), such as reactive oxygen species or reactive nitrogen species, in the locale of the dialysis membrane. The following two sections provide examples of the synthesis of various membranes that comprise MnTPyP as an exemplary catalytic agent, such membranes being appropriate for use as microdialysis membranes in transcutaneous analyte sensing systems.

5b. Dialysis Membrane Example 1: Immobilization of MnTPyP onto the Surface of a Polyamide or a Polyacrylonitrile Dialysis Membrane Described now is an example of a chemical method for associating an exemplary catalytic agent, such as a superoxide dismutase/catalase catalyst, with a surface of a dialysis or microdialysis membrane. The method comprises a covalent immobilization procedure that leaves the pore size and other functional properties of the dialysis membrane substantially unchanged.

In this example, the dialysis membrane may be either polyamide (PA)-based or polyacrylonitride (PAN)-based and the catalyst is MnTPyP. The method of associating the MnTPyP with the membrane is described below in terms of two converging pathways, as shown separated by the dotted line in Scheme I, which may be followed in any order or contemporaneously. In a first pathway, shown in Scheme I to the left and below the dotted line, a carboxyl group is introduced at the surface of a membrane via hydrolysis. In the case of a PA-based membrane (a single amide group is shown), the amide bond is hydrolyzed, while in the case of a PAN-based membrane (a single acrylonitride group is shown), the —CN group is hydrolyzed. The carboxyl group is then activated with TSTU (O—(N-succininidyl)-N,N, N',N'-tetramethyluronium tetrafluoroborate)) in the presence of DIPEA (N,N-diisopropylethylamine) to form a N-hydroxysuccinimide (NHS) ester. The NHS ester is then coupled with one of the two amino groups of propylenediamine, which is present in excess. In a second pathway, depicted above and to the right side of the dotted line in Scheme I, the starting compound, meso-tetrapyridyl porphyrin, is quaternized at its pyridyl nitrogen(s) to introduce one carboxylic acid group (as shown) or two carboxylic acid groups (not shown). This is followed by acidification and metallation, via $Mn^{2+}$ in the presence of tetrafluoracetic acid (TFA), resulting in MnTPyP with one carboxylic acid group (as shown) or two carboxylic groups (not shown). This is further followed by activation of the carboxylic acid group(s) to form a NHS ester of the MnTPyP. Finally, as the first and second pathways converge, the amino groups associated with the membrane obtained via the first pathway are coupled with the NHS ester of MnTPyP obtained via the second pathway to provide the desired dialysis membrane associated with a catalytic agent.

Scheme I

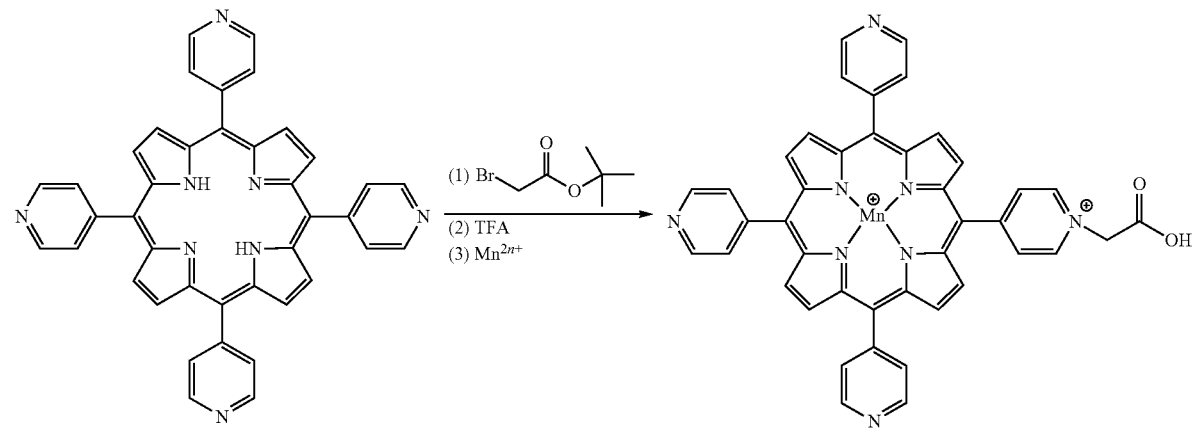

39
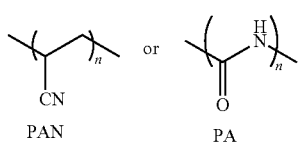
PAN  PA
OH⁻
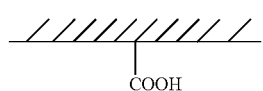
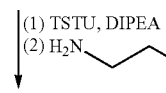
(1) TSTU, DIPEA
(2) H₂N⟶NH₂
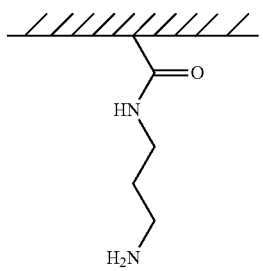
40
-continued
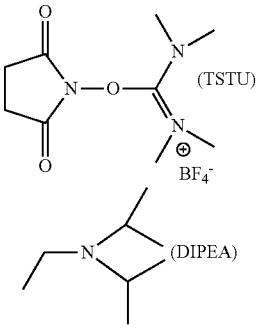
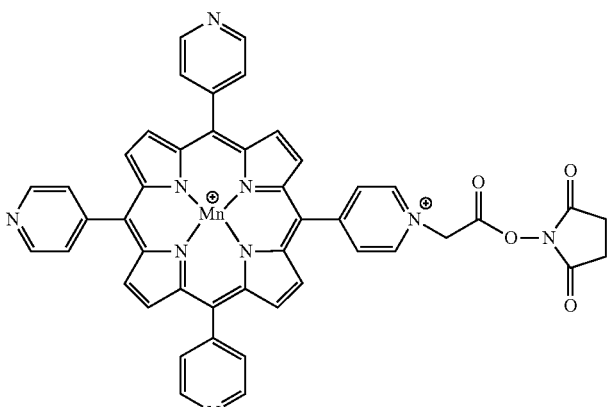
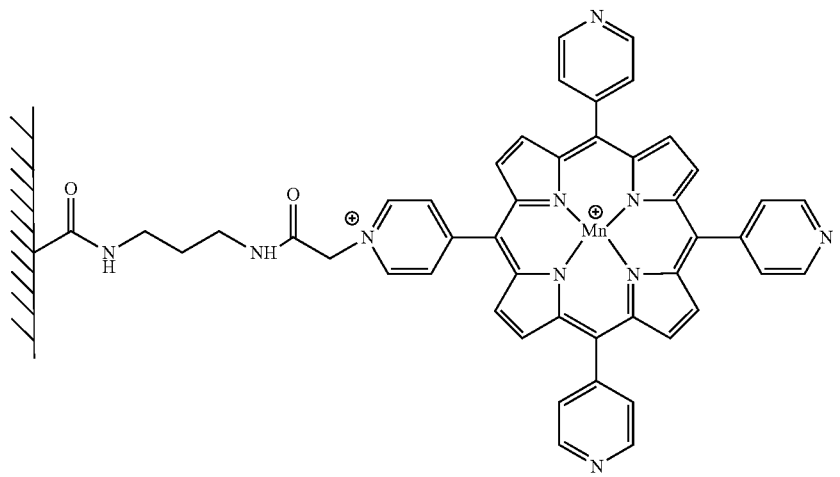

5c. Dialysis Membrane Example 2: Immobilization of MnT-PyP onto the Surface of Polysulfone Dialysis Membranes Described now is a second example of a method for associating an exemplary catalytic agent, such superoxide dismutase/catalase catalyst, with a surface of a dialysis or microdialysis membrane. Here, the dialysis membrane is a polysulfone (PS)-based dialysis membrane and the catalyst is MnTPyP. The method of associating the MnTPyP with the membrane is described below in terms of two converging pathways, as shown separated by the dotted line in Scheme II, which may be followed in any order or contemporaneously. In the first pathway, as shown in Scheme II below and to the left of the dotted line, an amino group is introduced at the surface of a membrane via a Lewis acid (AlCl$_3$)-catalyzed Friedel-Crafts reaction, which may be described as an electrophilic substitution of aromatic rings in the polysulfone molecule(s). The second pathway, as shown in Scheme II above and to the right side of the dotted line, results in an NHS ester of MnT-PyP, as described in the immediately preceding example. Finally, as the first and second pathways converge, the amino groups associated with the membrane obtained via the first pathway are coupled with the NHS ester of MnTPyP obtained via the second pathway to provide the desired dialysis membrane associated with a catalyst.

Scheme II

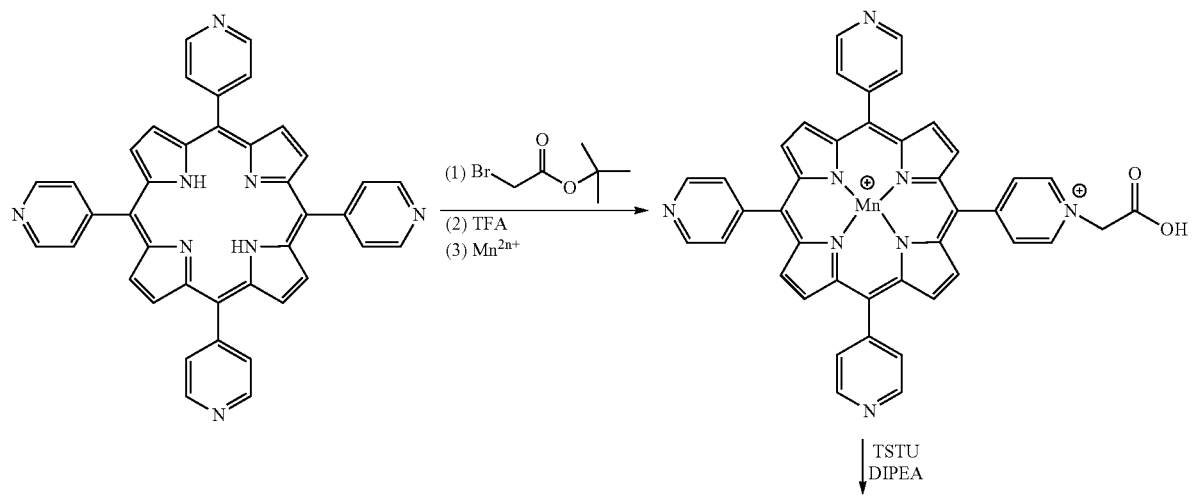

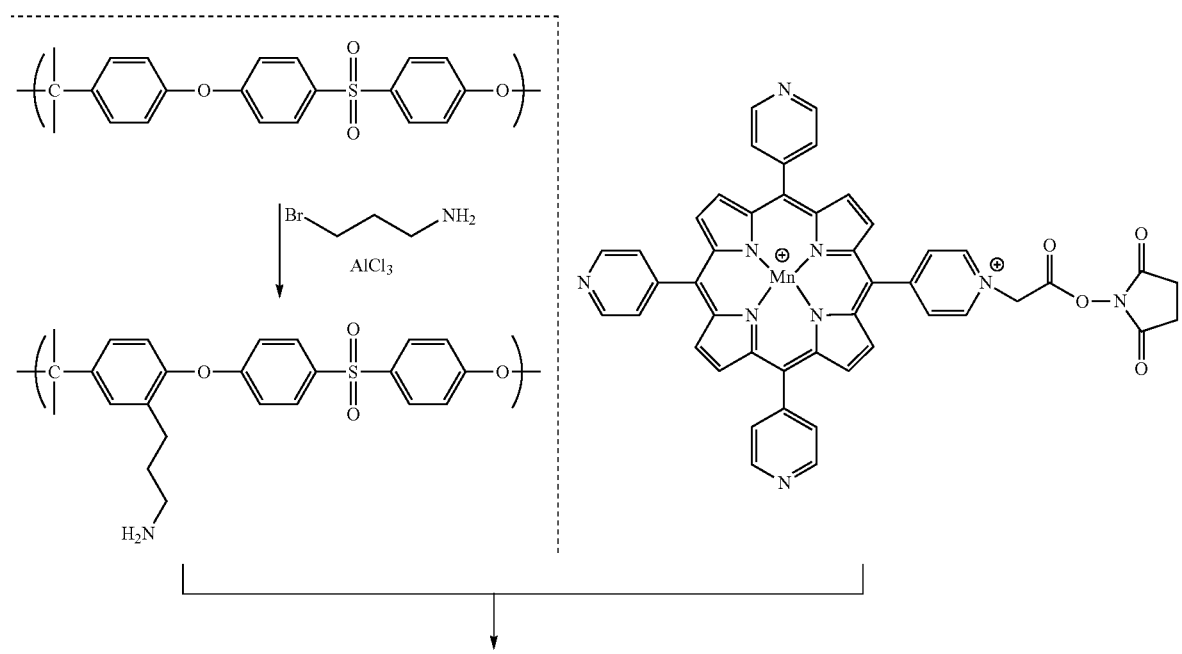

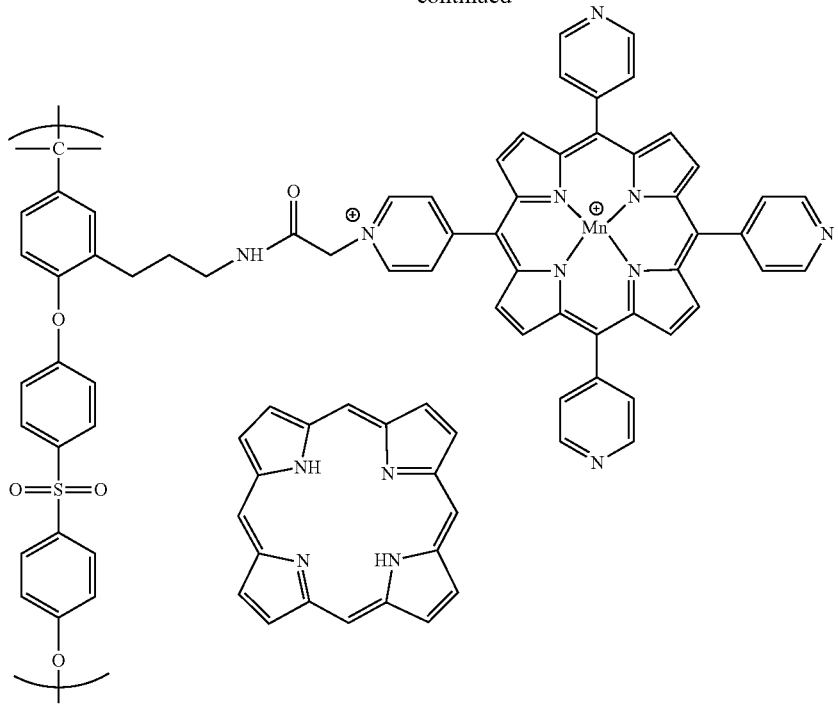

5d. Dialysis System Example 3: Performance of Sensors In Situ: Operation with a Conventional Dialysis Membrane Vs. Operation with a Dialysis Membrane Comprising Superoxide Dismutase/Catalase Catalytic Activity As has been described in the two immediately preceding examples, a superoxide dismutase/catalase catalyst may be associated with, or incorporated onto, dialysis or microdialysis membranes of various composition, such as polyamide-, polyacrylonitride-, or polysulfone-based membranes. In an analyte sensor that utilizes a catalyst-associated membrane, the membrane is a structural interface that separates the native interstitial fluid from the dialysate, which having crossed the membrane is in a post-biological space and constitutes the fluid to which the sensor has access. There is an approximate order of magnitude difference in total area between a microdialysis membrane and a membrane covering the surface of an electrochemical sensing surface; as an example, a microdialysis tube of 0.6 mm diameter×30 mm in length has a total area of about 56 mm$^2$, while a membrane covering the surface of the transcutaneous electrochemical sensor described above has a total area of about 7 mm$^2$. However, aside from such difference in dimension, a microdialysis membrane is highly analogous to a protective membrane that covers a sensing layer of a transcutaneous sensor, both in terms of physical location, within the subcutaneous space, and in terms of function, as an interface between native interstitial fluid and a derivative fluid that engages a transducing apparatus of the sensor.

Just as the catalyst-enhanced membrane of the transcutaneous sensor may improve sensor performance, as described above, it is contemplated that a superoxide dismutase/catalase-associated microdialysis membrane may improve the performance of a microdialysis-based analyte sensor. For example, it is anticipated that a comparison of microdialysis-based analyte sensors with superoxide dismutase/catalase catalyst-associated membranes and such sensors with conventional membranes, would show the former to be better or superior in terms of performance. An indication of better performance may be an increase in the correlation coefficient between the data delivered by the sensor and the data delivered by an in vitro sensor, merely by way of example, where in vitro sensors include conventional glucose strip readers, such as those marketed by Abbott Diabetes Care (Alameda, Calif.), MediSense Products (Bedford, Mass.), or Medtronic MiniMed (Northridge, Calif.), and bench-top clinical glucose analyzers, such as those marketed by YSI (Yellow Springs, Ohio), merely by way of example.

Another indication of better performance may be found by way of a Clarke grid analysis of glucose data from an experimental microdialysis-based sensor system (i.e., with a superoxide dismutase/catalase-associated microdialysis membrane) and such data from a reference microdialysis-based sensor system (i.e., with a conventional microdialysis membrane) (see the data from the transcutaneous electrochemical system, detailed above in Table 2). The Clarke system classifies the relationship of experimental data points to reference data points into five zones. Zone A includes experimental data points that are within 20% of reference values, and are considered to be in agreement with the reference values. Zone B includes experimental data points that are greater than reference data by more than 20%, but are considered benign errors. Zone C includes experimental data that deviate from reference values by more than 20%, and if reacted to by insulin treatment, would cause an overcorrecting blood glucose response. Zone D includes experimental data that deviate from reference values by more than 20% and would lead to a potentially dangerous failure to detect, and correct via insulin treatment, glucose levels that are outside of the normal range. Finally, Zone E errors would result in insulin treatment errors that would move the glucose concentration in the direction opposite that which would be appropriate. It is anticipated that a comparison of glucose data from an experimental microdialysis-based sensor system and from a reference microdialysis-based sensor system via a Clarke grid analysis, would associate the former with a greater percentage of data points falling into Zone A (the accurate zone), and a lesser percentage of data points falling into Zone B (benign error), Zone C (error leading to an overcorrecting error), Zone D (error leading to a dangerous failure to detect and correct), and/or Zone E (error leading to a dangerous error in the direction of correction).

Still another indication of better performance may be found by way of noise-related metrics, such as the noise parameter described above in the example of the performance of a superoxide dismutase/catalase mimic-enhanced electrochemical sensor embodiment. That is, it is anticipated that a level of noise in a signal coming from a superoxide dismutase/catalase-associated microdialysis sensor system would be less than that coming from a convention microdialysis sensor system.

Yet another indication of better performance may be found by way of determining the operating lifetime of a superoxide dismutase/catalase-associated, microdialysis-based sensor system. In general, microdialysis-based sensors have a limited time during which they reliably deliver signals that accurately report glucose concentration in bodily fluid. It is anticipated that various statistical measures of operating lifetime, such as a median effective operating lifetime, of a superoxide dismutase/catalase-associated, microdialysis-based sensor system and a conventional microdialysis-based sensor system, would show the operating lifetime of the former to be greater, perhaps considerably so, than to the latter.

A further indication of better performance may be found by observing failure rates. A certain percentage of microdialysis-based sensors fail after insertion in that they do not begin generating reliable signals within a few hours of subcutaneous implantation. It is anticipated that a comparison of failure rates associated with superoxide dismutase/catalase-associated, microdialysis-based sensor systems and those associated with a conventional microdialysis-based sensor systems, would show the former to be less, perhaps considerably so, than the latter.

6. Use of Biocompatibility-Promoting Catalytic Agents in Connection with Sensors Placed on the Skin that Sample Transcutaneously-Drawn Fluid 6a. Wound Fluid Sampling from a Cutaneous Port An approach to obtaining an analyte-sample-containing fluid is to create a disruption in the skin or a cutaneous wound that then serves as a port from which a wound fluid exudes, the exudate or wound fluid being derived from interstitial fluid, and thus a derivative portion of a biofluid. The exuded or extracted fluid is then provided to an external analyte sensor. In a system that makes use of a cutaneous port, the port itself is a biological, structural interface that separates the native interstitial fluid from the post-biological exudate. A small cutaneous wound can be created by any of several methods, including photothermally disrupting or burning via laser, disrupting via ultrasonic waves, and wounding via propelled particles (as noted below, with regard to needle-less injection technology), merely by way of example. Each of these methods provides wounds, or cutaneous ports that vary in their specifics, but, for the purpose of understanding this invention, may be appreciated as providing the biological structure that comprises a cutaneous port, and as a whole constitutes an interface of biological composition that separates the native interstitial fluid from the wound exudate. Such exudate, having crossed through the biological interface is in an external post-biological space, is different from and derived from the interstitial fluid, and is a biofluid derivative that may be provided to the sensor placed on the skin. The present invention provides a biocompatibility-promoting catalytic agent or agents disposed in the locale of such an interface.

Thus, embodiments of the present invention provide an analyte-sensing kit that comprises a sensor, for example, one that is placed on the skin over a cutaneous port, and a catalytic agent in a form or formulation, or in appropriate vehicle, that is capable of being applied to the locale of an interface between a biofluid and the transducing apparatus of the sensor, such interface being exemplified by a cutaneous port. The kit may further comprise an applicator with which to apply the catalytic agent to the locale of the interface. The sensor can be any of the types of analyte sensors described herein, which are applied to continuous or near-continuous analyte sensing such that the sensor, or a portion of the sensor, is in contact with a bodily fluid. Such a sensor, as described elsewhere herein, may make use of any form of transduction, whereby the presence of an analyte and its concentration are transduced into an informative signal generated by the sensor. The catalytic agent, as described elsewhere herein, may promote the biocompatibility of the sensor, and in so doing, may improve the performance of the sensor. Appropriate formulations for the catalytic agent, and applicators are described further below. Embodiments of the analyte-sensing kit are appropriate for any type of sensor where the provision of the catalytic agent to the locale of the described interface is not feasible or easily accomplished by incorporation into the sensor itself. A sensor placed on the body that is contacted by fluid from a cutaneous port is an example of such an embodiment. A sensor placed over a cutaneous port may also have an interface other than that represented by the cutaneous port itself, such as a synthetic membrane that intervenes between the wound exudate, itself a biofluid derivative, and the sensing surface or transducing mechanism of the sensor. Any such intervening structure is also an interface, and embodiments of the present invention include a catalytic agent disposed in the locale of any such interface.

An exemplary cutaneous port-based sensing system is depicted in FIGS. 8A and 8B. In this exemplary type of cutaneous port-based sensing, a cutaneous port 30c is created by a laser beam, however this embodiment of the invention serves more generally as a representative of a variety of cutaneous port-based analyte sensing systems. By way of further explanation, in the context of the present invention, the cutaneous port 30c serves as an interface between native interstitial fluid and a derivative fluid that actually contacts the transducing apparatus of the sensor, and accordingly it is labeled with a variant of part number 30, as is the case with all types of interface as are present in the various embodiments of the invention described herein. As depicted in FIG. 8A, a cutaneous port is created by a laser beam 23 supplied by a laser device 24, and as depicted in FIG. 8B the exuded fluid is captured by a sampling patch portion 10c of a sensor that is then applied to the skin, over the site of the transcutaneous port 30c. The mechanical and operational details of appropriate laser devices are known (U.S. Pat. No. 6,679,841 to Bojan) and include the use of electromagnetic radiation preferably from the infrared range (wavelengths of about 380 nm to about 780 nm) and visible range (wavelengths of about 780 nm to about 300,000 nm); photosensitizing materials may include dyes and pigments; and the period of exposure time required to burn an operable cutaneous port is between about 10 millisecond to about 1 second. According to the present invention, a catalytic agent 32 is applied in the locale of the interface, or cutaneous port, 30c. Behind the transcutaneous port, or interface 30c, lies the biofluid 40, in this case the interstitial fluid that occupies the subcutaneous space broadly beneath the surface of the skin 50. As depicted in FIG. 8B, following the initial step that involves creation of the transcutaneous port, for continuous sensing, an exudate capturing portion 10c of a sensor (not further shown) is then attached for a period of time to the surface of the skin 50. The exudate capturing device 10c collects fluid that exudes outwardly (as shown by a directional arrow) through the transcutaneous port, conveys such fluid to the transducing apparatus 18 for generation of an informative signal, which signal is then further conveyed to a data storage system.

Topically applied to the skin 50, and more specifically in the locale of the cutaneous port or interface 30c is a catalytic agent 32, which is sufficient to catalyze the degradation of local biologically generated reactive oxygen species or reactive nitrogen species. Such a catalyst, MnTPyP, for example, can be provided to the cutaneous port site, or the surface of the wound associated with the port, in any suitable formulation or vehicle or topical form, such as a liquid or dispersion, a gel, a lotion, an ointment, or a dry powder, by way of example. Liquid formulations may be dispensed by spraying with a manual pump, or by pressurizing into an aerosol form and releasing as a spray. The appropriately formulated catalyst may be applied to the surface of the skin prior to creating the cutaneous wound, or immediately after wound creation, or any combination of applications such that the catalytic agent is effective in its capacity of degrading local reactive metabolites. The catalyst formulation may comprise one or more excipient cutaneous penetration enhancer(s), such as water, an alcohol, such as methanol, ethanol, and 2-propanol, an alkyl methyl sulfoxide, a pyrrolidone, laurocapram, a solvent, such as acetone, dimethyl acetamide, dimethyl formamide, and tetrahydroftiryl alcohol, an amphiphile, such as an L-amino acid, an anionic surfactant, a cationic surfactant, an amphoteric surfactant, a nonionic surfactant, and a fatty acid, and any suitable combination thereof. Other penetration enhancers may be used, alone or in any suitable combination, such as those disclosed in Remington, *The Science and Practice of Pharmacy*, 19$^{th}$ Ed., p. 1583 (1995). Applicators appropriate to the formulation or vehicle that carries the catalytic agent are well known in the art, and are included within the kit that are suitable for embodiments of the invention that make use of a cutaneous port. In the case of aerosol embodiments, for example, an aerosol sprayer is included. In the case of liquid, cream, or ointment kit embodiments, the applicator is generally an appropriately designed opening of the container holding the catalytic agent-containing vehicle. In still other embodiments, the agent in an appropriate vehicle is embedded or otherwise included on a portion of the sensor that makes contact with the skin, when the sensor is positioned correctly on the skin. The disposing of a catalytic agent(s) 32 in such topical form means that the catalytic agents would have a broad locale of catalytic action. The site of catalytic action would include reactants in fluid on the outer surface of the skin, as for example between the skin and a sensor mounted on the skin, as well as below the surface of the skin, where the catalytic agent would engage reactants within a native biofluid such as interstitial fluid.

Another example of a potential continuous, in vivo, analyte sensing system based on drawing fluid from a cutaneous port takes advantage of a so-called needle-less injection technology, which in addition to effecting a needle-less injection, also creates a transcutaneous port. Needle-less injection involves high-pressure blasting fine particles into the skin to create a wound from which small volumes of fluid exude. Various patents describe this technology, including U.S. Pat. No. 6,372,045 to McCabe (filed May 12, 1999), U.S. Pat. No. 6,475,181 to Potter (filed May 22, 2000). U.S. Pat. No. 6,602, 678 to Kwon (filed Dec. 17, 2001) describes the application of the technology to non-invasive or minimally invasive analyte monitoring methods.

As discussed above, in the context of the laser-based system for creating a cutaneous port (as depicted in FIG. 8), a catalytic agent can be topically disposed onto the skin, where it is thus localized at the interface between native biofluid (interstitial fluid) and the biofluid derivative or wound fluid, that exudes and actually contacts the transducing system of an analyte sensor. Further, and more particularly in the case where the cutaneous wound is created by the driving force of propelled particles, as in the needle-less injection approach to cutaneous port creation, embodiments of the present invention provide for the inclusion of a catalytic agent, such as a superoxide dismutase/catalase catalyst, in the particulate material that is propelled into the skin. The catalytic agent may be associated with particles of appropriate composition; it may, for example be incorporated within particles, coated onto the surface of particles. The catalytic agent may also be configured into a particulate form itself, where the catalytic agent comprises a substantially major fraction of the particle. Finally, propellant, port-creating particles may comprise a heterogeneous population that includes a catalytic agent in at least one of these particulate forms. Such a method of application of a catalytic agent consolidates wound creation and provision of a biocompatibility-promoting catalytic agent into a single methodology.

It is anticipated that performance of cutaneous-port based sensors in which a catalytic agent, such as a superoxide dismutase/catalase catalyst, is disposed in the locale of the wound, will improve compared to the performance of sensors without such a catalyst disposed in the locale of the wound. Superior performance will manifest as higher quality data. Sensor data can be improved in a variety of ways, as has been detailed above in the examples of enhanced performance described above, in the context of experimental data coming from a transcutaneous electrochemical glucose sensor, as well as in the prophetic example of the performance of a catalyst-associated, microdialysis-based sensor system.

6b. Iontophoretically-Driven Fluid Sampling

As previously described, another type of cutaneous port that can be utilized in connection with an in vivo analyte sensing system can be provided via reverse iontophoresis, such as that the devices and methods described in various U.S. patents, including U.S. Pat. No. 5,771,890 of Tamada, issued on Jun. 30, 1998; U.S. Pat. No. 6,023,629 of Tamada, issued on Feb. 8, 2000; U.S. Pat. No. 6,144,869 of Berner et al., issued on Nov. 7, 2000; U.S. Pat. No. 6,298,254 of Tamada, issued on Oct. 2, 2001; U.S. Pat. No. 6,393,318 of Conn et al., issued on May 21, 2002; and U.S. Pat. No. 6,438,414 of Conn et al., issued on Aug. 20, 2002. The application of reverse iontophoresis toward the creation of a cutaneous port involves a weak current being applied to a cutaneous site, such that charged compounds move outwardly from the subcutaneous space through the iontophoretic site on the skin. As an example of reverse iontophoretic conditions, the applied current density may be in the range of about 0.01 to 0.5 mA/cm$^2$. Two electrodes are involved, each corresponding to a cutaneous port through which iontophoretically driven fluid is driven. The polarity of the two electrodes involved is alternated at a rate of that can vary at a rate of about one switch per 10 seconds to one switch per hour. The movement of charged solutes is accompanied by the movement of water through the skin, the osmotic force of this process, in turn, brings uncharged solutes from the subcutaneous space through the iontophoretic site as well. In the context of a glucose sensor, for example, glucose is thus moved out of the body, the concentration of glucose in the iontophoretic fluid being a function of the concentration in the interstitial fluid. When the iontophoretic fluid contacts a sensor on the skin, such as an electrochemical glucose sensor, the sensor transduces the concentration of an analyte of interest, such as glucose, into an informative signal.

A schematic illustration of such an iontophoretic system is provided in FIG. 9. The sensor 10d rests on the surface of the skin 50, and comprises an electrode assembly 15, which itself, includes a negative electrode 29n and a positive electrode 29p. The electrodes overlay iontophoretic sites or cutaneous ports 30a and 30b on the surface of the skin 50. Biofluid 40 moves (indicated by arrows) from within the subcutaneous space 52 outwardly across the surface of the skin 50, specifically through the interface sites 30a and 30b, where it emerges onto the skin as a biofluid derivative 42, or iontophoretic fluid, which is then drawn into the reservoir assembly 17 of the sensor 10d, where it is conveyed further to the transducing apparatus of the (sensor not shown). A catalytic agent 32 is disposed generally on the skin beneath the sensor, but more specifically at the interfacing cutaneous ports 30a and 30b.

In the context of the iontophoretic embodiments of the presently described invention, a sufficient amount of a superoxide dismutase/catalase catalyst, such as MnTPyP, is disposed in the locale of the interface, the iontophoretic site on the skin. In that locale, the catalyst affects the local concentrations of reactive oxygen species, for example, reduces these local concentrations, and affects the biology of the site, for example, by slowing the recruitment of neutrophils to the site. A superoxide dismutase/catalase catalyst, such as MnTPyP, may be provided to the iontophoretic site in any suitable formulation or vehicle, such as an aerosol, a liquid or dispersion, a powder, and any combination thereof. An aerosol preparation with minimal ingredients, including primarily propellant and alcohol is the preferred mode of application over ointments and creams, as the latter tend to interfere with adhesion of the sensor to the skin. The appropriately formulated catalytic agent may be applied to the surface of the skin prior to placing the iontophoretic sensor on the surface of the skin.

It is anticipated that data from iontophoretic-port based sensors in which a catalytic agent, such as a superoxide dismutase/catalase catalyst, is provided to the iontophoretic site will provide superior quality data compared to the data coming from such sensors without such a catalytic agent disposed in the locale of the iontophoretic site. Sensor data may be improved in a variety of ways, as has been detailed above in the examples of enhanced performance described above, in the context of experimental data coming from a transcutaneous electrochemical sensor, or in the prophetic example of the performance of a microdialysis-based sensor system with a catalytic agent incorporated into the membrane.

7. Biocompatibility-Promoting Catalytic Agents Incorporated into Long-Term Implanted Sensors Some analyte sensors are designed to be fully implanted within the body, in contrast to the sensors in previous sections, all of which are designed for partial implantation, or transcutaneous insertion. Fully implantable sensors are more invasive in nature, and their insertion is more medically intensive than the various methods described above, but the advantage offered by fully implanted sensors is that of a longer-term solution, with stable sensor operation and minimal maintenance over a period of months. Communication of sensor data to external devices is accomplished through wire leads that exit the body for external connections, or by radio frequency transmission of data to external receivers. Implanted analyte sensors can be located in many sites in the body, so long as they are exposed to a biofluid that is in osmotic communication with the vascular circulatory system. Accordingly, sensors can be implanted subcutaneously, intramuscularly, intraperitoneally, neurally (e.g., within the brain or spinal cord), or vascularly (e.g., in veins or arteries), merely by way of example. The biofluid to which such sensors are exposed, thus includes subcutaneous fluid, interstitial fluid, cerebral fluid, such as cerebrovascular fluid, cerebrospinal fluid, and the like, and vascular fluid, such as arterial fluid, venous fluid, capillary fluid, blood, and the like, merely by way of example. In general, long-term implantable sensors make use of enzyme-based electrochemical transduction, but other transduction methods have been utilized, such as the optical transduction approach described in U.S. Pat. No. 6,122,536 to Sun (filed Jun. 23, 1998) and U.S. Pat. No. 6,049,727 to Crothall, filed Apr. 3, 1998, and U.S. Patent Application No. U.S. 2004028612A1 to Bakthan and Wessling, filed Jun. 5, 2003.

Just as a transcutaneous electrochemical sensor includes a membrane that serves various purposes, including slowing the rate of exposure to high analyte concentrations and protecting against interfering species, so too, does a fully implanted electrochemical sensor generally have a protective interface between the native biofluid and the fluid that actually engages the sensing mechanism. See, for example, U.S. Pat. No. 6,466,810 of Ward, filed Nov. 2, 2000, U.S. Pat. No. 6,702,857 of Brauker et al., filed Jul. 27, 2001, U.S. Pat. No. 6,741,877 of Shults et al., filed Jan. 21, 2000, U.S. Patent Application Publication 2003/0217966 A1 of Tapsak, filed May 22, 2002, and U.S. Pat. No. 6,400,974 of Lesho, filed Jun. 29, 2000. These various fully implantable sensors within the prior art all have a structural interface, such as a protective membrane, between the original biofluid that provides an analyte sample, and the actual and final fluid that engages the transducing mechanism of the sensor, even though they differ significantly in some their features, for example, in the type of transducing system they use to recognize an analyte and quantify its concentration. Such protective membranes in fully implanted sensors are, in the context of the presently described invention, an interface between a native biofluid and a second fluid, a filtrate of the native biofluid, which actually engages the sensing surface of an electrochemical sensor. According to the present invention, a catalytic agent is disposed in the locale of such an interface or protective membrane. The catalytic agent may be one capable of catalyzing the degradation of reactive species of oxygen and/or nitrogen, capable of being located to engage such species within the biofluid to which the sensor is exposed, and present in sufficient quantity to decrease local concentrations of such reactive species in the biofluid. The presence and activity of such a catalytic agent may promote, enhance, or improve the biocompatibility of the sensor and thereby, the performance of the sensor.

FIGS. 10A and 10B provide an illustration of a portion of an implantable sensor, with a protective membrane between the biofluid and the transducing apparatus, and with a catalytic agent associated with the membrane. FIG. 10A is a cutaway perspective view of a portion of an electrochemical sensor 10e; in particular a head portion which is attached to a body portion (not shown) that includes a housing that encloses other parts that contribute to the sensor function, such as a circuit board and microprocessor for processing electrochemical input into an informative signal, a battery for power, and an antenna for sending signal to an external device. Three electrodes, a working electrode 29a, a reference electrode 29b, and a counter electrode 29c are partially exposed in the figure, and can be seen each to be surrounded for part of their length within the ceramic head portion of the sensor 10e, with one end of each penetrating the surface of the head portion, and the other end of each extending into the interior of the body of the sensor. The most distal portion of the head portion of the sensor 10e, beginning where the electrodes terminate is the sensing region 17, and is shown in an enlarged side view in FIG. 10B. There, the end portions of electrodes 29a, 29b, and 29c can be seen terminating in such a way as to be contiguous with the surface of the head of sensor 10e. Covering the sensing region 17 is a transducer, including a sensing membrane 18a that includes glucose oxidase, which recognizes glucose and initiates the first step in transduction of the glucose concentration into an informative signal. The external portion of the sensing region 17 is exposed to the surrounding biofluid 50. The sensing membrane 18a and its function is analogous to the sensing membrane 18a of the transcutaneous sensor shown in FIG. 4B. Covering this sensing layer 18a is a second layer, an interfacing membrane 30, which includes a catalytic agent 32, such as a superoxide dismutase/catalase catalyst, or other organic or organic-metal compound that catalyzes the degradation of reactive species of oxygen or nitrogen. In other embodiments (not shown), the catalytic agent 32 may be incorporated directly into the sensing layer 18a.

In fully implantable sensors, such as those described above, and as in the example illustrated in FIG. 10, it can be appreciated that the sensing surface represents but a small fraction of the total surface of the implanted sensor. A biological response to the sensor, such as foreign body response that would be mounted by the immune system, could thus be directed to the sensor as a whole, and such response to the entirety or a portion of the surface could contribute to diminishing biocompatibility or performance of the sensor through its sensing surface. Accordingly, biocompatibility-promoting catalytic agents could be disposed over or associated with portions of the sensor other than immediately over the sensing region, such as the outer surface of the head or body portions of a sensor, in its entirety. The surface of the sensor may comprise metallic or polymeric compounds, for example, with which a catalytic agent may be associated, by covalent linkage for example. Such association of biocompatibility agents with portions of a fully implantable sensor other than those immediately in the locale of an interface between the biofluid and the transducing mechanism may improve the biocompatibility of the complete sensor.

It is anticipated that data from fully implanted sensors in which a superoxide dismutase/catalase catalyst is provided in the locale of such an interface will provide superior quality data compared to the data coming from such sensors without such a catalyst disposed in the locale of the interface. Analyte sensor data can be improved in a variety of ways, as has been detailed above in the examples of enhanced performance of transcutaneous electrochemical sensors, and in the prophetic example of the performance of a catalyst-enhanced microdialysis-based sensor system. Finally, fully implanted sensors stay in the body for periods of many months, in contrast to the periods of several days that transcutaneous sensors are applied to body surfaces. Accordingly, the fully implanted sensors are more subject to the longer-term processes of immune rejection or the foreign body response, and the attendant biofouling and fibrous encapsulation. It is anticipated that the inventive sensors, with catalytic agents disposed at the interface between the biofluid and the transducing surface of the sensor will experience a lower rate of the occurrence of such long-term complications.

The foregoing description of this invention, including the examples and embodiments therein, demonstrates various advantages of the inclusion of superoxide-dismutase/catalase catalysts in sensors that sample analytes in bodily fluids or their derivatives. Various embodiments of these inventive sensors include systems that make use of transcutaneously-placed sensors, cutaneous-port systems with sensors placed on the skin, transcutaneous microdialysis systems with sensors placed on the skin, and sensors fully implanted in the body. Embodiments of this invention include examples of various forms of transduction by which analyte concentrations generate informative signals, including electrochemical and viscosimetric technologies. In each system, an interface has been described between the native physiological fluid and the sample fluid that actually contacts or otherwise engages the sensor. The invention provides for the disposition of superoxide-dismutase/catalase catalyst(s) in the locale of such interface. Various modifications of the inventive sensors and methods of using them will be readily apparent to those of skill in the art to which the present invention is directed upon review of the specification.

Various references, publications, provisional and/or non-provisional U.S. patent applications, U.S. patents, non-U.S. patent applications, and/or non-U.S. patents, have been identified herein, each of which is incorporated herein in its entirety by this reference. Various aspects and features of the present invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the present invention may have been described largely with respect to applications, or more specifically, medical applications, involving diabetic humans, it will be understood that such aspects and features also relate to any of a variety of applications involving non-diabetic humans and any and all other animals. Further, although various aspects and features of the present invention may have been described largely with respect to applications involving transcutaneous sensors, it will be understood that such aspects and features also relate to any of a variety of sensors that are suitable for use in connection with the body of an animal or a human, such as those suitable for implantation within the body of an animal or a human. Finally, although the various aspects and features of the present invention have been described with respect to various embodiments and specific examples herein, all of which may be made or carried out conventionally, it will be understood that the invention is entitled to protection within the full scope of the appended claims.

The invention claimed is:

1. An analyte sensor for use in connection with a biofluid, comprising:
    a transducer sufficient for generating a signal that corresponds to a concentration of an analyte in a derivative portion of the biofluid when the derivative portion of the biofluid contacts the transducer, wherein the transducer comprises an analyte responsive enzyme and wherein the analyte responsive enzyme oxidizes the analyte;
    an interface sufficient for passage of the derivative portion of the biofluid toward the transducer when the biofluid contacts the interface; and
    an organic-metal catalytic agent disposed only in the interface and sufficient to catalyze the degradation of reactive oxygen species and/or reactive nitrogen species of biological origin in the biofluid and/or the derivative portion of the biofluid, the agent selected from a proteinaceous catalytic agent, a non-proteinaceous catalytic agent, or any combination thereof.

2. The sensor of claim 1, wherein the sensor is partially implantable in a body.

3. The sensor of claim 1, wherein the sensor is a transcutaneous sensor.

4. The sensor of claim 1, wherein the sensor is fully implantable in a body.

5. The sensor of claim 1, wherein the transducer is an electrochemical transducer.

6. The sensor of claim 1, wherein the interface comprises a membrane that at least partially covers the transducer.

7. The sensor of claim 1, wherein the metal of the organic-metal catalytic agent is manganese.

8. The sensor of claim 1, wherein the catalytic agent is MnTPyP.

9. The sensor of claim 1, wherein the catalytic agent is associated with an outer surface of the sensor.

10. The sensor of claim 1, wherein the catalytic agent is an agent of sensor biocompatibility.

11. The sensor of claim 1, wherein the catalytic agent is an agent of sensor signal quality.

12. The sensor of claim 1, wherein the catalytic agent is an anti-neutrophilic agent.

13. The sensor of claim 1, wherein the analyte responsive enzyme is glucose oxidase.

14. An analyte sensor for use in connection with a biofluid, comprising:
   a transducer sufficient for generating a signal that corresponds to a concentration of an analyte in a derivative portion of the biofluid when the derivative portion of the biofluid contacts the transducer, wherein the transducer comprises an analyte responsive enzyme and wherein the analyte responsive enzyme oxidizes the analyte;
   an interface sufficient for passage of the derivative portion of the biofluid toward the transducer when the biofluid contacts the interface; and
   an organic-metal catalytic agent disposed only in the interface, the agent selected from a proteinaceous catalytic agent, a non-proteinaceous, organic-metal catalytic agent, or any combination thereof, the agent sufficient to mitigate the recruitment of neutrophils to the locale.

15. The sensor of claim 14, wherein the analyte responsive enzyme is glucose oxidase.

16. The sensor of claim 14, wherein the sensor is partially implantable in a body.

17. The sensor of claim 14, wherein the sensor is a transcutaneous sensor.

18. The sensor of claim 14, wherein the sensor is fully implantable in a body.

19. The sensor of claim 14, wherein the transducer is an electrochemical transducer.

20. The sensor of claim 14, wherein the interface comprises a membrane that at least partially covers the transducer.

21. The sensor of claim 14, wherein the metal of the organic-metal catalytic agent is manganese.

22. The sensor of claim 14, wherein the catalytic agent is MnTPyP.

23. The sensor of claim 14, wherein the catalytic agent is associated with an outer surface of the sensor.

24. The sensor of claim 14, wherein the catalytic agent is an agent of sensor biocompatibility.

25. The sensor of claim 14, wherein the catalytic agent is an agent of sensor signal quality.

* * * * *